US006258937B1

(12) United States Patent
Tong et al.

(10) Patent No.: US 6,258,937 B1
(45) Date of Patent: Jul. 10, 2001

(54) HEPADNAVIRUS RECEPTOR

(75) Inventors: Shuping Tong; Jisu Li, both of Charlestown; Jack R. Wands, Waban, all of MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/361,707

(22) Filed: Jul. 27, 1999

Related U.S. Application Data

(62) Division of application No. 08/683,262, filed on Jul. 18, 1996, now Pat. No. 5,929,220.

(60) Provisional application No. 60/001,371, filed on Jul. 21, 1995.

(51) Int. Cl.$^7$ .................... C07K 14/00
(52) U.S. Cl. .................... 530/350
(58) Field of Search .................... 530/350, 412

(56) References Cited

PUBLICATIONS

Kume et al., The Journal of Biological Chemistry, 266(5):3323–3329, 1991.*
Database GenEmbl on Gencore, accession numbers M64402 J05742 and D90266, Mar. 2000.*
Database Pir51 on MPSRCH, accession number A39521, Sep. 1997.*
Grgacic et al., J.Virol. 68:7344–7350, 1994; "The Large Protein of Duck Hepatitis B Virus Is Phosphorylated in the Pre–S Domain".
Macrae et al., Virology 181:359–363, 1991; "Myristylation of a Duck Hepatitis B Virus Envelope Protein Is Essential for Infectivity but Not for Virus Assembly".
Persing et al., J. Virol. 61:1672–1677, 1987; "The preS1 Protein of Hepatitis B Virus Is Acylated at Its Amino Terminus with Myristic Acid".
Fernholz et al., Virology 197:64–73, 1993; "Minor Envelope Proteins of Duck Hepatitis B Virus Are Initiated at Internal Pre–S AUG Codons but Are Not Essential for Infectivity".
Summers et al., J. Virol. 65:1310–1317, 1991; "Morphogenetic and Regulatory Effects of Mutations in the Envelope Proteins of an Avian Hepadnavirus".
Sureau et al., J. Virol. 67:366–372, 1993; "Role of the Large Hepatitis B Virus Envelope Protein in Infectivity of the Hepatitis Delta Virion".
Budkowska et al., 67:4316–4322, 1993; "Hepatitis B Virus (HBV) Binding Factor in Human Serum: Candidate for a Soluble Form of Hepatocyte HBV Receptor".
Budkowska et al., J. Virol. 69:840–848, 1995; "Fibronectin of Human Liver Sinusoids Binds Hepatitis B Virus: Identification by an Anti–Idiotypic Antibody Bearing the Internal Image of the Pre–S2 Domain".
Hertogs et al., Virology 197:549–557, 1993; "Endonexin II, Present on Human Liver Plasma Membranes, Is a Specific Binding Protein of Small Hepatitis B Virus (HBV) Envelope Protein".
Mehdi et al., J. Virol. 68:2415–2424, 1994; "Hepatitis B Virus Surface Antigen Binds to Apolipoprotein H".
Neurath et al., J. Exp. Med. 176:1561–1569, 1992; "Cells Transfected with Human Interleukin 6 cDNA Acquire Binding Sites for the Hepatitis B Virus Envelope Protein".
Pontisso et al., J. Gen. Virol. 73:2041–2045, 1992; "the preS1 domain of hepatitis B virus and IgA cross–react in their binding to the hepatocyte surface".
Pugh et al., Virology 172:564–572, 1989; "Infection and Uptake of Duck Hepatitis B Virus by Duck Hepatocytes Maintained in the Presence of Dimethyl Sulfoxide".
Tuttleman et al., J. Virol. 58:17–25, 1986; "In Vitro Experimental Infection of Primary Duck Hepatocyte Cultures with Duck Hepatitis B Virus".
Mandart et al., J. Virol., 49:782–792, 1984; "Nucleotide Sequence of a Cloned Duck Hepatitis B Virus Genome: Comparison with Woodchuck and Human Hepatitis B Virus Sequences".
Norder et al., Virology, 198:489–503, 1994; "Complete Genomes, Phylogenetic Relatedness, and Structural Proteins of Six Strains of the Hepatitis B Virus, Four of Which Represent Two New Genotypes".
Wang et al., Nature, 323:508–13, 1986; "Structure, sequence and expression of the hepatitis delta (δ) viral genome".
Mason et al., J. Virol. 36:829–36, 1978; "Virus of Pekin Ducks with Structural and Biological Relatedness to Human Hepatitis B Virus".
Sprengel et al., J. Virol., 62:3832–39, 1988; "Isolation and Characterization of a Hepatitis B Virus Endemic in Herons".
Summers et al., Proc. Natl. Acad. Sci. USA, 75:4533–37, 1978; "A virus similar to human hepatitis B virus associated with hepatitis and hepatoma in woodchucks".
Marion et al., Proc. Natl. Acad. Sci. USA, 77:2941–45, 1980; "A virus in Beechey ground squirrels that is related to hepatitis B virus of humans".
Mason et al., Hepatology, 9:635–645, 1989; "Experimental Systems for the Study of Hepadnavirus and Hepatitis Delta Virus Infections".
Yuasa et al., Virology 181:14–21, 1991; "Peptide Mapping of Neutralizing and Nonneutralizing Epitopes of Duck Hepatitis B Virus Pre–S Polypeptide".
Chassot et al., Virology 192:217–223, 1993; "Fine Mapping of Neutralization Epitopes on Duck Hepatitis B Virus (DHBV) pre–S Protein Using Monoclonal Antibodies and Overlapping Peptides".
Lu et al., J. Virol. 70:2277–2285, 1996; Protease–Induced Infectivity of Hepatitis B Virus for a Human Hepatoblastoma Cell Line.

* cited by examiner

*Primary Examiner*—Donna C. Wortman
*Assistant Examiner*—Brenda G. Brumback
(74) *Attorney, Agent, or Firm*—Fish & Richardson P.C.

(57) ABSTRACT

The invention features an hepadnavirus cellular receptor and a nucleic acid sequence that encodes the receptor. The receptor is a 170 kD surface glycoprotein, and is referred to as the p170 receptor.

2 Claims, 31 Drawing Sheets

A pre-S polypeptide containing p170 binding site blocks DHBV infectivity

| | 87 | | | 90 | | | 93 | | | 96 | | | 99 | | | 102 |
|---|---|---|---|---|---|---|---|---|---|---|---|---|---|---|---|---|
| wild-type | Q | **W** | **T** | P | **E** | **E** | **D** | Q | **K** | **A** | R | **E** | A | **F** | R | R |
| W88S | | S | | | | | | | | | | | | | | |
| P90L | | | | L | | | | | | | | | | | | |
| E91G | | | | | G | | | | | | | | | | | |
| E92V | | | | | | V | | | | | | | | | | |
| D93F | | | | | | | F | | | | | | | | | |
| K95S | | | | | | | | | S | | | | | | | |
| R97L | | | | | | | | | | | L | | | | | |
| R97C | | | | | | | | | | | C | | | | | |
| E98A | | | | | | | | | | | | A | | | | |
| E98V | | | | | | | | | | | | V | | | | |
| R102G | | | | | | | | | | | | | | | | G |
| E91G/K95S | | | | | G | | | | S | | | | | | | |
| E91G/R97C | | | | | G | | | | | | C | | | | | |
| K95S/A96T | | | | | | | | | S | T | | | | | | |
| K95S/R97C | | | | | | | | | S | | C | | | | | |
| K95S/R97L/E98A | | | | | | | | | S | | L | A | | | | |

FIG. 12

```
peptide 1     SVELRELYVMEISDNPGVHEAGEPEFK (SEQ ID NO:19)
peptide 2     LIDRTRIVIVPSLNPDGR-IA  (SEQ ID NO:20)
peptide 3     SLLSHEFQDETDTEEETLYSAK (SEQ ID NO:21)
peptide 4     VEEGKVPVLNTPD  (SEQ ID NO:22)
```

FIG. 14A

```
peptide 1     SVELRELYVMEISDNPGVHEAGEPEFK (SEQ ID NO:19)
bovine CPH    .F.G...L.L.L........P......
human CPH     .F.G...L.I.L........P......
AEBP1 gene        KI.A........D..L.....R
human CPN     ...G.H...L.F..H..I..PL...V.
human CPM     ..KG.N.W.LVVGRF.KE.RI.I....

peptide 2     LIDRTRIVIVPSLNPDGR-IA  (SEQ ID NO:20)
AEBP1 gene    .VQD...HL........YEV.
bovine CPH    ..HN...H.M.......
human CPN     ..QD...H.L..M....YEV.
human CPM     ..NS...H.M..M....
human CPH     ..HS...H.M.......
```

| | | | | | | | | | | | | | | | | | | | | | | |
|---|---|---|---|---|---|---|---|---|---|---|---|---|---|---|---|---|---|---|---|---|---|---|
| | | | | | | | | | | | | | | | | | | | | | | (SEQ ID NO:) |
| aa number | 6 | 7 | 8 | 9 | 10 | 11 | 12 | 13 | 14 | 15 | 16 | 17 | 18 | 19 | 20 | 21 | 22 | 23 | 24 | 25 | 26 | 27 | |
| aa | E | L | Y | V | M | E | I | S | D | N | P | G | V | H | E | A | G | E | P | E | F | K | (23) |
| possible nt | GAX | CTN | TAY | GTN | ATG | GAX | ATW | AGY | GAY | AAY | CCN | GGN | GTN | CAY | GAX | GCN | GGN | GAX | CCN | GAX | TTY | AAX | (24) |
| | | TTX | | | | | | TCN | | | | | | | | | | | | | | | (25) |
| degenerate primer & product | gax | ytn | tay | gtn | atg | gag | atC | TCG | GAC | AAC | CCC | GGY | GTY | cay | gax | gcn | ggn | gax | ccn | gax | tt | | (26) |
| specific primer & product | | | | | atg | gag | atc | tcg | gac | aac | ccC | GGC | GTC | CAT | GAA | GCA | GGT | GAG | CCA | GAG | TTC | AAG | (27) |

PK-69

| | | | | | | | | | | | | | | | | | | | | | | |
|---|---|---|---|---|---|---|---|---|---|---|---|---|---|---|---|---|---|---|---|---|---|---|
| aa number | 1 | 2 | 3 | 4 | 5 | 6 | 7 | 8 | 9 | 10 | 11 | 12 | 13 | 14 | 15 | 16 | 17 | 18 | 19 | 20 | 21 | 22 | |
| aa | S | L | L | S | H | E | F | Q | D | E | T | D | T | E | E | E | T | L | Y | S | A | K | (28) |
| possible nt | AGY | CTN | CTN | AGY | CAY | GAX | TTY | CAX | GAY | GAX | ACN | GAY | ACN | GAX | GAX | GAX | ACN | CTN | TAY | AGY | GCN | AAX | (29) |
| | TCN | TTX | TTX | TCN | | | | | | | | | | | | | | TTX | | TCN | | | (30) |
| degenerate primer & product | | tz | ytn | agy | cay | gax | tty | cax | gAT | GAA | ACA | GAC | ACT | GAA | GAA | gax | acn | ytn | tay | tcn | gcv | aa | (31) |
| specific primer | | | | | | | | | | | | | | | | | | | | | | | |
| & product | TCC | CTT | TTG | AGC | CAC | GAA | TTC | CAG | Gat | gaa | aca | gac | act | gaa | gaa | | | | | | | | (32) |

Primer sequences are written in small letters. For convenience antisense primers are written in the sense orientation.

```
1/1                                     31/11
ATG GGG CAA CAT CCA GCA AAA TCA ATG GAC GTC AGA CGG ATA GAA GGA GGA GAA ATA CTG (SEQ ID NO:33)
M   G   Q   H   P   A   K   S   M   D   V   R   R   I   E   G   G   E   I   L   (SEQ ID NO:34)
61/21                                   91/31
TTA AAC CAA CTT GCC GGA AGG ATG ATC CCA AAA GGG ACT TTG ACA TGG TCA GGC AAG TTT
L   N   Q   L   A   G   R   M   I   P   K   G   T   L   T   W   S   G   K   F
121/41                                  151/51
CCA ACA CTA GAT CAC GTG TTA GAC CAT GTG CAA ACA ATG GAG GAG ATA AAC ACC CTC CAG
P   T   L   D   H   V   L   D   H   V   Q   T   M   E   E   I   N   T   L   Q
181/61                                  211/71
AAT CAG GGA GCT TGG CCT GCT GGG GCG GGA AGG AGA GTA GGA TTA TCA AAT CCG ACT CCT
N   Q   G   A   W   P   A   G   A   G   R   R   V   G   L   S   N   P   T   P
241/81                                  271/91
CAA GAG ATT CCT CAG CCC CAG TGG ACT CCC GAG GAA GAC CAA AAA GCA CGC GAA GCT TTT
Q   E   I   P   Q   P   Q   W   T   P   E   E   D   Q   K   A   R   E   A   F
301/101                                 331/111
CGC CGT TAT CAA GAA GAA AGA CCA CCG GAA ACC ACC ACC ATT CCT CCG TCT TCC CCT CCT
R   R   Y   Q   E   E   R   P   P   E   T   T   T   I   P   P   S   S   P   P
361/121                                 391/131
CAG TGG AAG CTA CAA CCC GGG GAC GAT CCA CTC CTG GGA AAT CAG TCT CTC CTC GAG ACT
Q   W   K   L   Q   P   G   D   D   P   L   L   G   N   Q   S   L   L   E   T
421/141                                 451/151
CAT CCG CTA TAC CAG TCA GAA CCA GCG GTG CCA GTG ATA AAA ACT CCC CCC TTG AAG AAG
H   P   L   Y   Q   S   E   P   A   V   P   V   I   K   T   P   P   L   K   K
481/161
AAA
K
```

FIG. 16

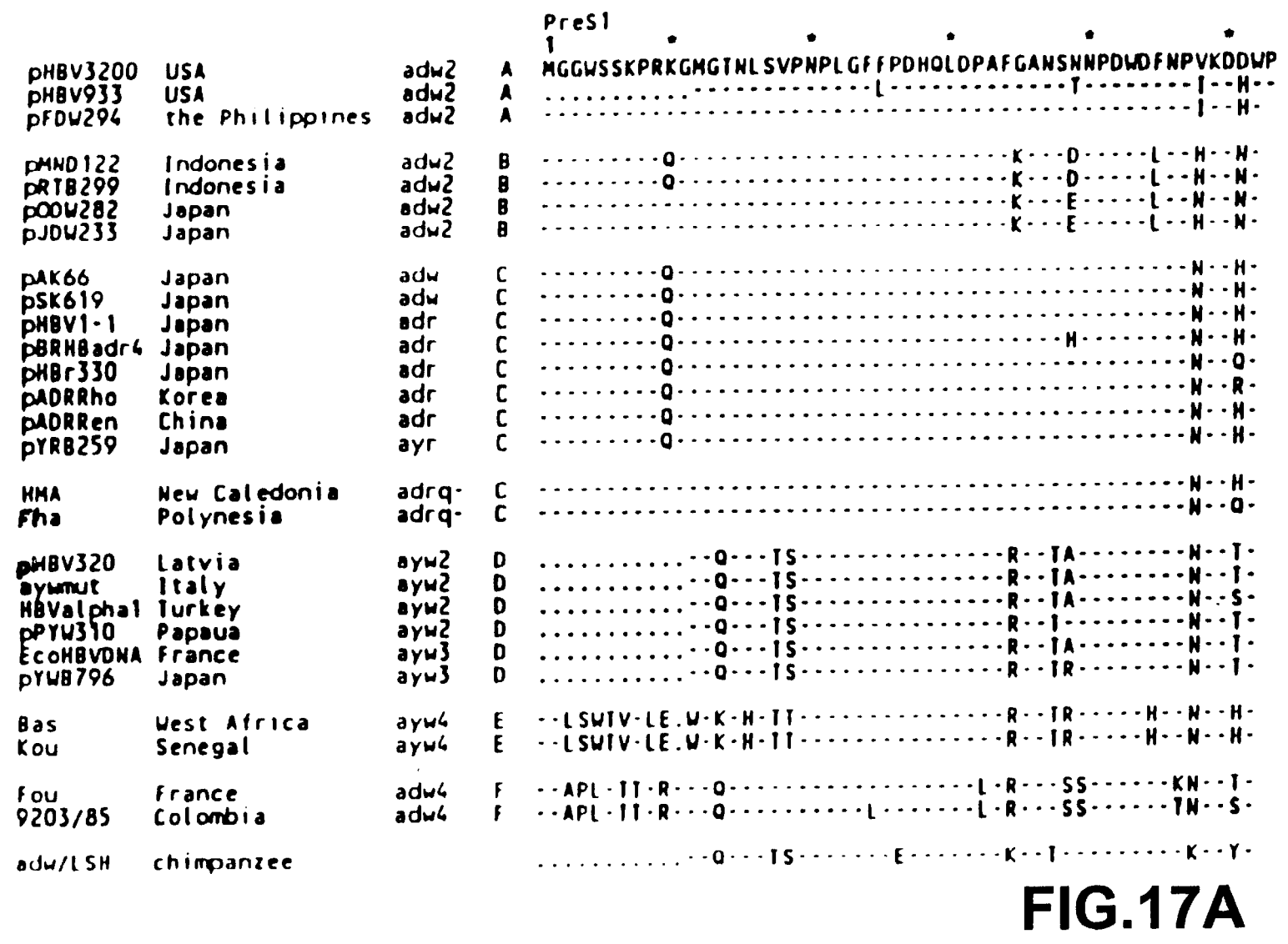

```
                                              PreS1
                                              1
pHBV3200     USA                 adw2   A     MGGWSSKPRKGMGTNLSVPNPLGFFPDHQLDPAFGANSNNPDWDFNPVKDDWP
pHBV933      USA                 adw2   A     ------------------------L-------------T--------I--H--
pFDW294      the Philippines     adw2   A     -----------------------------------------------I--H--

pMND122      Indonesia           adw2   B     ---------Q------------------------K---D-----L--H--N--
pRTB299      Indonesia           adw2   B     ---------Q------------------------K---D-----L--H--N--
pOOW282      Japan               adw2   B     ----------------------------------K---E-----L--N--N--
pJDW233      Japan               adw2   B     ----------------------------------K---E-----L--H--N--

pAK66        Japan               adw    C     ---------Q-------------------------------------N--H--
pSK619       Japan               adw    C     ---------Q-------------------------------------N--H--
pHBV1-1      Japan               adr    C     ---------Q-------------------------------------N--H--
pBRHBadr4    Japan               adr    C     ---------Q----------------------------H--------N--H--
pHBr330      Japan               adr    C     ---------Q-------------------------------------N--Q--
pADRRho      Korea               adr    C     ---------Q-------------------------------------N--R--
pADRRen      China               adr    C     ---------Q-------------------------------------N--H--
pYRB259      Japan               ayr    C     ---------Q-------------------------------------N--H--

HMA          New Caledonia       adrq-  C     -----------------------------------------------N--H--
Fha          Polynesia           adrq-  C     -----------------------------------------------N--Q--

pHBV320      Latvia              ayw2   D     ------------Q---TS----------------R--TA--------N--T--
aywmut       Italy               ayw2   D     ------------Q---TS----------------R--TA--------N--T--
HBValphal    Turkey              ayw2   D     ------------Q---TS----------------R--TA--------N--S--
pPYW310      Papaua              ayw2   D     ------------Q---TS----------------R--T---------N--T--
EcoHBVDNA    France              ayw3   D     ------------Q---TS----------------R--TA--------N--T--
pYWB796      Japan               ayw3   D     ------------Q---TS----------------R--TR--------N--T--

Bas          West Africa         ayw4   E     -LSWIV-LE.W-K-H-TT----------------R--TR-----H--N--H--
Kou          Senegal             ayw4   E     -LSWIV-LE.W-K-H-TT----------------R--TR-----H--N--H--

Fou          France              adw4   F     -APL-TT-R---Q-------------------L-R---SS------KN--T--
9203/85      Colombia            adw4   F     -APL-TT-R---Q----------L--------L-R---SS------TN--S--

adw/LSH      chimpanzee                       ------------Q---TS-------E--------K--I---------K--Y--
```

FIG.17A

PreS2 120–174

| | | | | |
|---|---|---|---|---|
| pHBV3200 | USA | adw2 | A | MQWNSTAFHQTLQDPRVRGLYLPAGGSSSGTVNPAPNIASHISSISARTGDPVTN |
| pHBV933 | USA | adw2 | A | -------L--A-------------------------------------------T |
| pFDW294 | the Philippines | adw2 | A | ----------A----------F---------L--V-T----------S-I--AP- |
| pMNO122 | Indonesia | adw2 | B | ------T-----------A--F------------VQ-IV-S----LSK-----P- |
| pRTB299 | Indonesia | adw2 | B | ------T-----------A--F------------VQ-I--S----LST-----P- |
| pOOW282 | Japan | adw2 | B | ------T--------G--A--F----------S--Q-IV-A----LSK-----P- |
| pJDW233 | Japan | adw2 | B | ------T-----------A--F----------S--Q-IV-A----LSK-----P- |
| pAK66 | Japan | adw | C | ------T---A-L--------F------------V-TT--P---TFS-----AP- |
| K619 | Japan | adw | C | ------T---A-L--------F------------V-TT--P----FS-----AP- |
| BV1-1 | Japan | adr | C | ------T---A-L--------F------------V-TTV-P----FS-----AP- |
| pBRHBadr4 | Japan | adr | C | ------T---A-L--------F------------V-TT--P-----S-----AP- |
| pHBr330 | Japan | adr | C | ------T---A-L--------F------------V-TT--P----FS-----AP- |
| pADRRho | Korea | adr | C | ------T---V-L--------F-P----------V-TT--P-----S-----AP- |
| ADRRen | China | adr | C | ------T---A-L--------F------------V-TT--P-----S-----AP- |
| pYRB259 | Japan | ayr | C | ------T---A-L--------F------------V-TT--P----FS-----AP- |
| HMA | New Caledonia | adrq- | C | ------T-Q-A-------V--F------------V-TT--L----FS-I------ |
| Cha | Polynesia | adrq- | C | ------T-Q-A-L--------F------------V-TT--L----FS-------- |
| pHBV320 | Latvia | ayw2 | D | ------T--------------F------------V-TTV-P----FS-I---AL- |
| aywmut | Italy | ayw2 | D | ------T--------------P------------V-TTV------FT-I---AL- |
| HBValpha1 | Turkey | ayw2 | D | ------T---------------------------V-TTV-P----FS-I---AL- |
| pPYW310 | Papaua | ayw2 | D | ------T--------------F------------V-TT--P----FS-I---AL- |
| EcoHBVDNA | France | ayw3 | D | ------T--------------F------------VLTT--PL---FS-I---AL- |
| pYWB796 | Japan | ayw3 | D | ---T--T---A----------F------------V-TT--P-L--FSKI--LAP- |
| Bas | West Africa | ayw4 | E | ------T---A----------F------------V-TT--L----FS-I---AP- |
| Kou | Senegal | ayw4 | E | ------T---A----------F------------V-TT--L----FS-I---AP- |
| Fou | France | adw4 | F | ------H---A-L-----A--F---------Q----T---LT----SK--G-AH- |
| 9203/85 | Colombia | adw4 | F | ------H---A-L-----A--F---------Q----T---LT----SK--G-AH- |
| adw/LSH | chimpanzee | | | ------T---A----------F---------L--V-T-------VFSI----AP- |

FIG. 17C

```
1/1                                     31/11
ATG GAG ATC TCG GAC AAC CCC GGT GTT CAT GAA GCA GGT GAG CCA GAG TTC AAG TAT ATT
M   E   I   S   D   N   P   G   V   H   E   A   G   E   P   E   F   K   Y   I
61/21                                   91/31
GGT AAC ATG CAT GGG AAT GAA GTT GTG GGG CGA GAG CTG CTC CTG AAC CTC ATC GAG TAC
G   N   M   H   G   N   E   V   V   G   R   E   L   L   L   N   L   I   E   Y
121/41                                  151/51
CTC TGC AAG AAC TTC GGC ACA GAT CCC GAA GTG ACT GAC TTG GTC CAG AGC ACG CGG ATC
L   C   K   N   F   G   T   D   P   E   V   T   D   L   V   Q   S   T   R   I
181/61                                  211/71
CAC ATC ATG CCG TCC ATG AAC CCA GAT GGC TAC GAG AAG TCC CAG GAA GGA GAC AGA GGA
H   I   M   P   S   M   N   P   D   G   Y   E   K   S   Q   E   G   D   R   G
241/81                                  271/91
GGC ACC GTT GGC AGA AAT AAC AGC AAC AAC TAC GAC CTG AAC CGG AAC TTC CCA GAT CAG
G   T   V   G   R   N   N   S   N   N   Y   D   L   N   R   N   F   P   D   Q
301/101                                 331/111
TTC TTC CAG GTG ACA GAC CCT CCG CAG CCA GAA ACT CTT GCT GTC ATG AGC TGG TTG AAA
F   F   Q   V   T   D   P   P   Q   P   E   T   L   A   V   M   S   W   L   K
361/121                                 391/131
ACT TAC CCG TTC GTG CTT TCA GCA AAC CTG CAT GGA GGT TCT CTG GTG GTT AAT TAC CCT
T   Y   P   F   V   L   S   A   N   L   H   G   G   S   L   V   V   N   Y   P
421/141                                 451/151
TTT GAT GAC GAT GAA CAA GGA ATA GCC ATA TAC AGT AAA TCC CCA GAC GAT GCT GTG TTT
F   D   D   D   E   Q   G   I   A   I   Y   S   K   S   P   D   D   A   V   F
481/161                                 511/171
CAG CAG CTG GCA CTT TCC TAC TCC AAG GAA AAC AAA AAG ATG TAT CAG GGA AGC CCT TGT
Q   Q   L   A   L   S   Y   S   K   E   N   K   K   M   Y   Q   G   S   P   C
541/181                                 571/191
AAG GAT TTG TAC CCC ACA GAG TAC TTT CCA CAT GGC ATC ACG AAC GGG GCC CAG TGG TAC
K   D   L   Y   P   T   E   Y   F   P   H   G   I   T   N   G   A   Q   W   Y
601/201                                 631/211
AAC GTT CCA GGT GGG ATG CAG GAC TGG AAT TAC TTA AAT ACC AAC CTG TTT GAA GTG ACC
N   V   P   G   G   M   Q   D   W   N   Y   L   N   T   N   L   F   E   V   T
661/221                                 691/231
ATT GAG CTG GGC TGT GTG AAA TAC CCA AAA GCA GAG GAG CTG CCG AAG TAC TGG GAG CAG
I   E   L   G   C   V   K   Y   P   K   A   E   E   L   P   K   Y   W   E   Q
721/241                                 751/251
AAC CGT AGA TCT CTC CTC CAG TTC ATT AAA CAG GTT CAC CGC GGC ATC TGG GGA TTT GTG
N   R   R   S   L   L   Q   F   I   K   Q   V   H   R   G   I   W   G   F   V
781/261                                 811/271
CTG GAT GCC ACG GAC GGA AGG GGC ATT CTC AAC GCC ACC ATC AGC GTC GCC GAC ATC AAC
L   D   A   T   D   G   R   G   I   L   N   A   T   I   S   V   A   D   I   N
841/281                                 871/291
CAC CCC GTG ACC ACC TAC AAA GAT GGG GAC TAC TGG CGC CTC TTG GTC CAG GGG ACG TAC
H   P   V   T   T   Y   K   D   G   D   Y   W   R   L   L   V   Q   G   T   Y
901/301                                 931/311
AAA GTC ACA GCA TCT GCC CGA GGG TAT GAT CCA GTC ACT AAA ACG GTG GAA GTC GAC AGC
K   V   T   A   S   A   R   G   Y   D   P   V   T   K   T   V   E   V   D   S
961/321                                 991/331
AAA GGT GGG GTG CAG GTC AAC TTC ACT CTT TCA CGG ACA GAC GCC AAA GTG GAG GAG GGG
K   G   G   V   Q   V   N   F   T   L   S   R   T   D   A   K   V   E   E   G
1021/341                                1051/351
AAG GTG CCA GTC CTG AAC ACC CCA GAC ACC AGC GAC CCC AAC GAG AAG GAG TTT GAG ACT
K   V   P   V   L   N   T   P   D   T   S   D   P   N   E   K   E   F   E   T
1081/361                                1111/371
CTG ATC AAA GAT CTA TCT GCT GAA AAC GGC CTG GAG (SEQ ID NO:63)
L   I   K   D   L   S   A   E   N   G   L   E   (SEQ ID NO:64)
```

FIG. 18

```
1/1                                     31/11
TTT GTC CAG GAC AAG AGT GGC AAG GCA ATT TCT AAA GCT ACC ATT GTC CTT AAT GAA GGC
F   V   Q   D   K   S   G   K   A   I   S   K   A   T   I   V   L   N   E   G
61/21                                   91/31
TTG AGG GTC TAC ACT AAA GAA GGT GGC TAT TTC CAT GTG CTG TTG GCT CCT GGT TTG CAT
L   R   V   Y   T   K   E   G   G   Y   F   H   V   L   L   A   P   G   L   H
121/41                                  151/51
AAC ATC AAT GCG ATA GCG GAT GGG TAC CAA CAA AAG CAT ATG AAG GTC TTG GTA CGC CAC
N   I   N   A   I   A   D   G   Y   Q   Q   K   H   M   K   V   L   V   R   H
181/61                                  211/71
GAT GCA CCC AGC TCT GTG TTC ATG GTA TTT GAC ATG GAA AAC AGG ATA TTT GGT CTG CCT
D   A   P   S   S   V   F   M   V   F   D   M   E   N   R   I   F   G   L   P
241/81                                  271/91
CGA GAG CTG GTT GTA ACT GTT GCA GGT GCA ATT ATG TCT GCT TTG GTC CTC ACT GCC TGT
R   E   L   V   V   T   V   A   G   A   I   M   S   A   L   V   L   T   A   C
301/101                                 331/111
ATC ATC TGG TGT GTC TGC TCA ATC AAG GCC AAC AGA CAC AAA GAT GGC TTC CAC TGC CGG
I   I   W   C   V   C   S   I   K   A   N   R   H   K   D   G   F   H   C   R
361/121                                 391/131
CAG CAC CAC GAC GAT TAC GAG GAC GAA ATC CGC ATG ATG TCC ACT GGC TCA AAG AAA TCC
Q   H   H   D   D   Y   E   D   E   I   R   M   M   S   T   G   S   K   K   S
421/141                                 451/151
CTT TTG AGC CAC GAA TTC CAG GAT GAA ACA GAC ACT GAA GAA (SEQ ID NO:65)
L   L   S   H   E   F   Q   D   E   T   D   T   E   E   (SEQ ID NO:66)
```

FIG. 19

```
      71                                                                                         118
HBV   H G G I L G W S P Q A Q G I L T T V S T I P P P A S T N R Q S G R Q P T P I S P P L R D S H P Q
DHBV  A G R R V G L S N P T P Q E I P Q P Q W T P E E D Q K A R E A F R R Y Q E E R P P E T T T I P P
      69                                                                                         116
        *       *   *             *             *             *       *             * *       *   *

            HBV  (SEQ ID NO:67)                ------------------------------
            DHBV (SEQ ID NO:68)                    p170 binding site
```

FIG. 20

| | | | 97 | 98 | 99 | 100 | 101 | 102 | p120-binding |
|---|---|---|---|---|---|---|---|---|---|
| WT | Lys | Ala | Arg | Glu | Ala (Tyr) | Phe | Arg | Arg | + |
| R97C | | | Cys | | | | | | + |
| E98V | | | | Val | | | | | + |
| E98A | | | | Ala | | | | | + |
| A99D | | | | | Asp | | | | + |
| F100V | | | | | | Val | | | - |
| F100L | | | | | | Leu | | | - |
| F100W | | | | | | Trp | | | + |
| R101L | | | | | | | Leu | | − |
| R101H | | | | | | | His | | − |
| R101K | | | | | | | Lys | | + weak |
| R102G | | | | | | | | Gly | − |
| R102H | | | | | | | | His | - |
| R102K | | | | | | | | Lys | − |

FIG. 25A peptide 1: DVSGVLFQYPDTEGK (SEQ ID NO:70)

peptide 2: EVYRLALQTREQHIRRD (SEQ ID NO:71)

peptide 3: SGAQGEYAGLAAIK (SEQ ID NO:72)

peptide 4: IQPIEVDK (SEQ ID NO:73)

Peptide sequences of p120.

FIG. 30

```
1/1                                     31/11
GAG GCG GCG CGG TGC ATC GAG CAG CTG CTG CCG CGG CAC GAT GAC TTC TCC CGG CGG CAC
E   A   A   R   C   I   E   Q   L   L   P   R   H   D   D   F   S   R   R   H
61/21                                   91/31
ATC GGC CCC CGG GAG GGG GAG AAG AGG GAG ATG CTG CGA GCC CTC GGG GTG CAG AGC GTC
I   G   P   R   E   G   E   K   R   E   M   L   R   A   L   G   V   Q   S   V
121/41                                  151/51
GAG GAG CTG ATG GAT AAA GCC ATC CCG GGC AGC ATC CGG CTG CGC AGG CCG CTG AGG ATG
E   E   L   M   D   K   A   I   P   G   S   I   R   L   R   R   P   L   R   M
181/61                                  211/71
GAG GAC CCC GTG GGT GAA AAT GAA ATC CTT GAA ACT TTA TAC AAT ATT GCA AGC AAG AAC
E   D   P   V   G   E   N   E   I   L   E   T   L   Y   N   I   A   S   K   N
241/81                                  271/91
AAG ATA TGG AGG TCC TAT ATA GGC ATG GGT TAT TAC AAC TGC TCA GTG CCT CAA CCC ATT
K   I   W   R   S   Y   I   G   M   G   Y   Y   N   C   S   V   P   Q   P   I
301/101                                 331/111
GCA CGG AAT TTG TTG GAG AAT GCA GGA TGG GTT ACC CAG TAT ACT CCC TAC CAA CCT GAG
A   R   N   L   L   E   N   A   G   W   V   T   Q   Y   T   P   Y   Q   P   E
361/121                                 391/131
GTC TCA CAG GGC AGG CTG GAG AGC CTG CTA AAT TAC CAG ACT ATG GTG TGT GAT ATC ACA
V   S   Q   G   R   L   E   S   L   L   N   Y   Q   T   M   V   C   D   I   T
421/141                                 451/151
GGA ATG GAT GTG GCT AAT GCA TCA TTG CTG GAT GAG GGG ACA GCT GCT GCA GAA GCT ATG
G   M   D   V   A   N   A   S   L   L   D   E   G   T   A   A   A   E   A   M
481/161                                 511/171
CAA TTA TGT CAC AGG CAC AAC AAA AGG AGG AAG TTT TAT GTA GAT TCC CGA TGC CAC CCT
Q   L   C   H   R   H   N   K   R   R   K   F   Y   V   D   S   R   C   H   P
```

FIG. 31A

```
541/181                                 571/191
CAG ACT ATA GCA GTG GTC CAA ACT AGA GCC AAT TAT ACA GGT GTT ATT ACT GAG CTC AAA
Q   T   I   A   V   V   Q   T   R   A   N   Y   T   G   V   I   T   E   L   K
601/201                                 631/211
TTA CCC CAT GAG ATG GAT TTC AGT GGA AAG GAT GTC AGT GGA GTA TTA TTT CAG TAT CCA
L   P   H   E   M   D   F   S   G   K   D   V   S   G   V   L   F   Q   Y   P
661/221                                 691/231
GAC ACT GAG GGG AAG GTG GAA GAC TTC TCT GAA CTT GTT GAA AGA GCT CAT CAG AAC GGG
D   T   E   G   K   V   E   D   F   S   E   L   V   E   R   A   H   Q   N   G
721/241                                 751/251
ACT CTT GCC TGC TGT GCT ACT GAT CTT CTG GCT CTC TGT ATT CTG AAG CCT CCT GGA GAG
T   L   A   C   C   A   T   D   L   L   A   L   C   I   L   K   P   P   G   E
781/261                                 811/271
TTT GGG GTA GAT GTT GTC CTG GGT AGC TCC CAG AGA TTT GGT GTG CCA CTC TGC TAT GGG
F   G   V   D   V   V   L   G   S   S   Q   R   F   G   V   P   L   C   Y   G
841/281                                 871/291
GGA CCC CAC GCA GCA TTC TTC GCT GTC AAG GAA AAC CTA GTG AGA ATG ATG CCA GGC AGG
G   P   H   A   A   F   F   A   V   K   E   N   L   V   R   M   M   P   G   R
901/301                                 931/311
ATG GTG GGT GTC ACA AGA GAT GCA AAT GGA AAA GAA GTT TAC CGA CTG GCT TTA CAA ACA
M   V   G   V   T   R   D   A   N   G   K   E   V   Y   R   L   A   L   Q   T
```

FIG. 31B

```
961/321                                 991/331
CGA GAG CAG CAT ATC AGG AGG GAC AAA GCT ACA AGC AAC ATC TGC ACA GCA CAG GCT CTT
R   E   Q   H   I   R   R   D   K   A   T   S   N   I   C   T   A   Q   A   L
1021/341                                1051/351
CTG GCT AAT ATG GCA GCC ATG TTT GGT GTC TAC CAT GGG TCT GAT GGA TTA AGG GAT ATT
L   A   N   M   A   A   M   F   G   V   Y   H   G   S   D   G   L   R   D   I
1081/361                                1111/371
GCA AGA CGG GTA CAC AAT GCT ACT TTA ATC CTG GCT GAA GGT CTC AGG AGA GCT GGT CAT
A   R   R   V   H   N   A   T   L   I   L   A   E   G   L   R   R   A   G   H
1141/381                                1171/391
AAA CTG CAC CAT GAT CTG TTC TTT GAT ACC TTG ACA GTC ACG TGT GGA TGC TCA GTC AAA
K   L   H   H   D   L   F   F   D   T   L   T   V   T   C   G   C   S   V   K
1201/401                                1231/411
GAA GTT TTG GAC AGG GCA GCT CTT AGA AAG ATA AAT TTT CGC ATT TAT AGT GAT GGC AGA
E   V   L   D   R   A   A   L   R   K   I   N   F   R   I   Y   S   D   G   R

1261/421                                1291/431
CTT GGA GTA TCA CTT GAT GAA ACT GTA AGT GAG AAA GAC CTA GAT GAC ATA TTA TGG ATT
L   G   V   S   L   D   E   T   V   S   E   K   D   L   D   D   I   L   W   I
1321/441                                1351/451
TTT GGT TGC GAG TCT TCA GCT GAA CTA ATT GCT GAA GGT ATG GGC GAG GAA ACC AAA GGT
F   G   C   E   S   S   A   E   L   I   A   E   G   M   G   E   E   T   K   G
1381/461                                1411/471
ATC CTT AGC ACC CCA TTT AAG AGA ACT TCC AAA TTC TTG ACC CAT CAG GTT TTC AAC AGC
I   L   S   T   P   F   K   R   T   S   K   F   L   T   H   Q   V   F   N   S
```

FIG. 31C

```
1441/481                                          1471/491
TAT CAC TCC GAA ACA AAT ATC GTA CGG TAC ATG AAG AGA TTA GAA AAC AAA GAT ATT TCC
Y   H   S   E   T   N   I   V   R   Y   M   K   R   L   E   N   K   D   I   S
1501/501                                          1531/511
CTT GTT CAC AGC ATG ATT CCT TTG GGG TCC TGT ACA ATG AAG CTC AAT AGT TCA GCT GAA
L   V   H   S   M   I   P   L   G   S   C   T   M   K   L   N   S   S   A   E
1561/521                                          1591/531
CTT GCA CCT ATT TCA TGG AAG GAA TTT GCC AAC ATC CAC CCC TTT GTG CCC TTG GAT CAA
L   A   P   I   S   W   K   E   F   A   N   I   H   P   F   V   P   L   D   Q
1621/541                                          1651/551
GCT CAA GGG TAT CAG CAG CTT TTC AAG GAC TTA GAG AAG GAC CTG TGT GAG ATT ACT GGT
A   Q   G   Y   Q   Q   L   F   K   D   L   E   K   D   L   C   E   I   T   G
1681/561                                          1711/571
TAC GAC AAA ATC TCC TTC CAA CCA AAC AGT GGA GCC CAA GGA GAG TAC GCA GGC TTG GCC
Y   D   K   I   S   F   Q   P   N   S   G   A   Q   G   E   Y   A   G   L   A
1741/581                                          1771/591
GCA ATC AAA GCT TAT TTA AAT GCA AAA GGA GAA CGT CAT CGA AGT GTT TGC CTT ATT CCT
A   I   K   A   Y   L   N   A   K   G   E   R   H   R   S   V   C   L   I   P
1801/601                                          1831/611
AGA TCT GCT CAT GGT ACA AAT CCA GCA AGT GCA CAG ATG GCA GGG ATG AAG ATT CAA CCA
R   S   A   H   G   T   N   P   A   S   A   Q   M   A   G   M   K   I   Q   P
```

FIG. 31D

```
1861/621                                1891/631
GTT GAA GTA GAT AAA AAT GGG AGC ATT GAT ATC TCC CAT TTA AAA GCA ATG GTG GAC AAA
V   E   V   D   K   N   G   S   I   D   I   S   H   L   K   A   M   V   D   K
1921/641                                1951/651
CAC AAG GAG AAC CTG GCA GCC ATC ATG ATC ACA TAC CCT TCC ACC AAT GGT GTG TTT GAG
H   K   E   N   L   A   A   I   M   I   T   Y   P   S   T   N   G   V   F   E
1981/661                                2011/671
GAG GAG ATT GGG GAT GTG TGT GAG CTG ATT CAC AAA AAC GGA GGC CAG GTT TAC CTG GAT
E   E   I   G   D   V   C   E   L   I   H   K   N   G   G   Q   V   Y   L   D
2041/681                                2071/691
GGA GCA AAC ATG AAC GCC CAA GTG GGT CTG TGT CGT CCT GGA GAT TAT GGC TCT GAT GTC
G   A   N   M   N   A   Q   V   G   L   C   R   P   G   D   Y   G   S   D   V
2101/701                                2131/711
TCT CAC TTA AAC CTT CAC AAA ACC TTT TGC ATT CCC CAT GGA GGA GGA GGA CCT GGA ATG
S   H   L   N   L   H   K   T   F   C   I   P   H   G   G   G   G   P   G   M
2161/721                                2191/731
GGA CCA ATT GGA GTG AAG AAA CAT CTG GCT CCC TAC TTG CCT ACC CAT CCT GTC ATC AAG
G   P   I   G   V   K   K   H   L   A   P   Y   L   P   T   H   P   V   I   K
```

FIG. 31E

```
2221/741                                2251/751
ATT CAG ACG GAT AAG GAT GCA TGT CCT TTG GGT ACT GTC AGT GCT GCA CCT TGG GGT TCC
I   Q   T   D   K   D   A   C   P   L   G   T   V   S   A   A   P   W   G   S
2281/761                                2311/771
AGT GCT ATA TTG CCT ATT TCC TGG GTG TAT ATC AAG ACA ATG GGA GCA AAG GGT CTT AAA
S   A   I   L   P   I   S   W   V   Y   I   K   T   M   G   A   K   G   L   K
2341/781                                2371/791
CAC GCT TCT GAG GTT GCT ATA TTA AAT GCA AAC TAC ATG GCA AAG AGG CTG GAG AAG CAC
H   A   S   E   V   A   I   L   N   A   N   Y   M   A   K   R   L   E   K   H
2401/801                                2431/811
TAC AAA ATC CTT TTC AGA GGA GTA AGA GGT TAT GTA GCC CAT GAA TTC ATT TTG GAT ACA
Y   K   I   L   F   R   G   V   R   G   Y   V   A   H   E   F   I   L   D   T
2461/821                                2491/831
AGA CCT TTC AAA AAA ACA GCA AAC ATT GAA GCT GTG GAT CTT GCT AAG CGA CTT CAG GAT
R   P   F   K   K   T   A   N   I   E   A   V   D   L   A   K   R   L   Q   D
2521/841                                2551/851
TAT GGT TTT CAT GCT CCA ACC ATG TCC TGG CCA GTG GCA GGC ACA CTT ATG ATT GAA CCA
Y   G   F   H   A   P   T   M   S   W   P   V   A   G   T   L   M   I   E   P
2581/861                                2611/871
ACA GAG TCT GAA GAC AAG GCA GAG CTG GAC AGG TTT TGT GAT GCA ATG ATC AGT ATT CGA
T   E   S   E   D   K   A   E   L   D   R   F   C   D   A   M   I   S   I   R
```

FIG. 31F

```
2641/881                                2671/891
CAG GAA ATT GCT GAA ATA GAG GAG GGC AGG ATG GAC CCT CAG ATT AAC CCA TTA AAG ATG
Q   E   I   A   E   I   E   E   G   R   M   D   P   Q   I   N   P   L   K   M
2701/901                                2731/911
TCA CCA CAT ACT CTA AAC TGT GTC ACT TCT TCA AAG TGG GAT CGT CCT TAT TCC AGA GAA
S   P   H   T   L   N   C   V   T   S   S   K   W   D   R   P   Y   S   R   E
2761/921                                2791/931
GTG GCA GCA TTC CCA CTG CCG TTT GTG AAA CCT GAG AGC AAG TTT TGG CCC ACA ATT GCT
V   A   A   F   P   L   P   F   V   K   P   E   S   K   F   W   P   T   I   A
2821/941                                2851/951
CGC ATC GAT GAC ATA TAC GGA GAT CAA CAC CTG GTT TGT ACC TGC CCA CCG ATG GAA GCC
R   I   D   D   I   Y   G   D   Q   H   L   V   C   T   C   P   P   M   E   A
2881/961                                2911/971
TAC GAA TCT CCC TTC TCT GAA CAG AAG AGA GCA TCT TCG TAA  (SEQ ID NO:74)
Y   E   S   P   F   S   E   Q   K   R   A   S   S   *    (SEQ ID NO:75)
```

FIG. 31G

SEQUENCE LISTING

```
(1) GENERAL INFORMATION:

   (iii) NUMBER OF SEQUENCES: 117

(2) INFORMATION FOR SEQ ID NO: 1:

     (i) SEQUENCE CHARACTERISTICS:
          (A) LENGTH: 27 base pairs
          (B) TYPE: nucleic acid
          (C) STRANDEDNESS: single
          (D) TOPOLOGY: linear

    (xi) SEQUENCE DESCRIPTION: SEQ ID NO: 1:

GCAGATCTAT GGGCAGAATC TTTCCAC                                         27

(2) INFORMATION FOR SEQ ID NO: 2:

     (i) SEQUENCE CHARACTERISTICS:
```

-continued (A) LENGTH: 25 base pairs
(B) TYPE: nucleic acid
(C) STRANDEDNESS: single
(D) TOPOLOGY: linear (xi) SEQUENCE DESCRIPTION: SEQ ID NO: 2:

GTGAATTCAG CGCAGGGTCC CCAAT 25

(2) INFORMATION FOR SEQ ID NO: 3:

(i) SEQUENCE CHARACTERISTICS:
(A) LENGTH: 28 base pairs
(B) TYPE: nucleic acid
(C) STRANDEDNESS: single
(D) TOPOLOGY: linear (xi) SEQUENCE DESCRIPTION: SEQ ID NO: 3:

TCAGATCTAT GATGGGGCAA CATCCAGC 28

(2) INFORMATION FOR SEQ ID NO: 4:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO: 4:

GCGAATTCAG GTACCAGACA TTTTCTTCTT 30

(2) INFORMATION FOR SEQ ID NO: 5:

(i) SEQUENCE CHARACTERISTICS:
(A) LENGTH: 27 base pairs
(B) TYPE: nucleic acid
(C) STRANDEDNESS: single
(D) TOPOLOGY: linear (xi) SEQUENCE DESCRIPTION: SEQ ID NO: 5:

GCGAATTCTT ATTCCTAACT CTTGTAA 27

(2) INFORMATION FOR SEQ ID NO: 6:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 6:

GARYTNTAYG TNATGGAGAT 20

(2) INFORMATION FOR SEQ ID NO: 7:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO: 7:

AAYTCNGGYT CNCCNGCYTC RTG 23

(2) INFORMATION FOR SEQ ID NO: 8:

(i) SEQUENCE CHARACTERISTICS:
(A) LENGTH: 21 base pairs

-continued (B) TYPE: nucleic acid
(C) STRANDEDNESS: single
(D) TOPOLOGY: linear (xi) SEQUENCE DESCRIPTION: SEQ ID NO: 8:

TKYTNAGYCA YGARTTYCAR G 21

(2) INFORMATION FOR SEQ ID NO: 9:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 9:

TTKGCNGART ANARNGTYTC 20

(2) INFORMATION FOR SEQ ID NO: 10:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 10:

ATGAAACAGA CACTGAAGAA 20

(2) INFORMATION FOR SEQ ID NO: 11:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 11:

ATGGAGATCT CGGACGGCCC 20

(2) INFORMATION FOR SEQ ID NO: 12:

(i) SEQUENCE CHARACTERISTICS:
(A) LENGTH: 20 base pairs
(B) TYPE: nucleic acid
(C) STRANDEDNESS: single
(D) TOPOLOGY: linear (xi) SEQUENCE DESCRIPTION: SEQ ID NO: 12:

TTCTTCAGTG TCTGTTTCAT 20

(2) INFORMATION FOR SEQ ID NO: 13:

(i) SEQUENCE CHARACTERISTICS:
(A) LENGTH: 9 amino acids
(B) TYPE: amino acid
(D) TOPOLOGY: linear (ii) MOLECULE TYPE: peptide (xi) SEQUENCE DESCRIPTION: SEQ ID NO: 13:

Gly Ser Arg Arg Ala Ser Val Gly Ser
1 5

(2) INFORMATION FOR SEQ ID NO: 14:

(i) SEQUENCE CHARACTERISTICS:

-continued (A) LENGTH: 30 base pairs
(B) TYPE: nucleic acid
(C) STRANDEDNESS: single
(D) TOPOLOGY: linear (xi) SEQUENCE DESCRIPTION: SEQ ID NO: 14:

ATCACTGAGC TCAAATTACC CCATGAGATG 30

(2) INFORMATION FOR SEQ ID NO: 15:

(i) SEQUENCE CHARACTERISTICS:
(A) LENGTH: 30 base pairs
(B) TYPE: nucleic acid
(C) STRANDEDNESS: single
(D) TOPOLOGY: linear (xi) SEQUENCE DESCRIPTION: SEQ ID NO: 15:

GGAAACTCGA GCTGGAAGCA GTGTTATGAA 30

(2) INFORMATION FOR SEQ ID NO: 16:

(i) SEQUENCE CHARACTERISTICS:
(A) LENGTH: 33 base pairs
(B) TYPE: nucleic acid
(C) STRANDEDNESS: single
(D) TOPOLOGY: linear (xi) SEQUENCE DESCRIPTION: SEQ ID NO: 16:

ATGGTACCAT GGAGGCGGCG CGGTGCATCG AGC 33

(2) INFORMATION FOR SEQ ID NO: 17:

(i) SEQUENCE CHARACTERISTICS:
(A) LENGTH: 31 base pairs
(B) TYPE: nucleic acid
(C) STRANDEDNESS: single
(D) TOPOLOGY: linear (xi) SEQUENCE DESCRIPTION: SEQ ID NO: 17:

ATCTCGAGAT ATTAACATTA GCAATGTTAC T 31

(2) INFORMATION FOR SEQ ID NO: 18:

(i) SEQUENCE CHARACTERISTICS:
(A) LENGTH: 16 amino acids
(B) TYPE: amino acid
(D) TOPOLOGY: linear (ii) MOLECULE TYPE: peptide (xi) SEQUENCE DESCRIPTION: SEQ ID NO: 18:

Gln Trp Thr Pro Glu Glu Asp Gln Lys Ala Arg Glu Ala Phe Arg Arg
1 5 10 15

(2) INFORMATION FOR SEQ ID NO: 19:

(i) SEQUENCE CHARACTERISTICS:
(A) LENGTH: 27 amino acids
(B) TYPE: amino acid
(D) TOPOLOGY: linear (ii) MOLECULE TYPE: peptide (xi) SEQUENCE DESCRIPTION: SEQ ID NO: 19:

Ser Val Glu Leu Arg Glu Leu Tyr Val Met Glu Ile Ser Asp Asn Pro
1 5 10 15

Gly Val His Glu Ala Gly Glu Pro Glu Phe Lys

-continued

```
            20                  25


(2) INFORMATION FOR SEQ ID NO: 20:

     (i) SEQUENCE CHARACTERISTICS:
          (A) LENGTH: 20 amino acids
          (B) TYPE: amino acid
          (D) TOPOLOGY: linear

    (ii) MOLECULE TYPE: peptide

    (xi) SEQUENCE DESCRIPTION: SEQ ID NO: 20:

Leu Ile Asp Arg Thr Arg Ile Val Ile Val Pro Ser Leu Asn Pro Asp
  1               5                  10                  15

Gly Arg Ile Ala
            20


(2) INFORMATION FOR SEQ ID NO: 21:

     (i) SEQUENCE CHARACTERISTICS:
          (A) LENGTH: 22 amino acids
          (B) TYPE: amino acid
          (D) TOPOLOGY: linear

    (ii) MOLECULE TYPE: peptide

    (xi) SEQUENCE DESCRIPTION: SEQ ID NO: 21:

Ser Leu Leu Ser His Glu Phe Gln Asp Glu Thr Asp Thr Glu Glu Glu
  1               5                  10                  15

Thr Leu Tyr Ser Ala Lys
            20


(2) INFORMATION FOR SEQ ID NO: 22:

     (i) SEQUENCE CHARACTERISTICS:
          (A) LENGTH: 13 amino acids
          (B) TYPE: amino acid
          (D) TOPOLOGY: linear

    (ii) MOLECULE TYPE: peptide

    (xi) SEQUENCE DESCRIPTION: SEQ ID NO: 22:

Val Glu Glu Gly Lys Val Pro Val Leu Asn Thr Pro Asp
  1               5                  10


(2) INFORMATION FOR SEQ ID NO: 23:

     (i) SEQUENCE CHARACTERISTICS:
          (A) LENGTH: 22 amino acids
          (B) TYPE: amino acid
          (D) TOPOLOGY: linear

    (ii) MOLECULE TYPE: peptide

    (xi) SEQUENCE DESCRIPTION: SEQ ID NO: 23:

Glu Leu Tyr Val Met Glu Ile Ser Asp Asn Pro Gly Val His Glu Ala
  1               5                  10                  15

Gly Glu Pro Glu Phe Lys
            20


(2) INFORMATION FOR SEQ ID NO: 24:

     (i) SEQUENCE CHARACTERISTICS:
          (A) LENGTH: 66 base pairs
          (B) TYPE: nucleic acid
          (C) STRANDEDNESS: single
          (D) TOPOLOGY: linear
```

-continued (xi) SEQUENCE DESCRIPTION: SEQ ID NO: 24:

GARCTNTAYG TNATGGARAT WAGYGAYAAY CCNGGNGTNC AYGARGCNGG NGARCCNGAR 60

TTYAAR 66

(2) INFORMATION FOR SEQ ID NO: 25:

(i) SEQUENCE CHARACTERISTICS:
(A) LENGTH: 66 base pairs
(B) TYPE: nucleic acid
(C) STRANDEDNESS: single
(D) TOPOLOGY: linear (xi) SEQUENCE DESCRIPTION: SEQ ID NO: 25:

GARTTRTAYG TNATGGARAT WTCNGAYAAY CCNGGNGTNC AYGARGCNGG NGARCCNGAR 60

TTYAAR 66

(2) INFORMATION FOR SEQ ID NO: 26:

(i) SEQUENCE CHARACTERISTICS:
(A) LENGTH: 62 base pairs
(B) TYPE: nucleic acid
(C) STRANDEDNESS: single
(D) TOPOLOGY: linear (xi) SEQUENCE DESCRIPTION: SEQ ID NO: 26:

GARYTNTAYG TNATGGAGAT CTCGGACAAC CCCGGYGTYC AYGARGCNGG NGARCCNGAR 60

TT 62

(2) INFORMATION FOR SEQ ID NO: 27:

(i) SEQUENCE CHARACTERISTICS:
(A) LENGTH: 54 base pairs
(B) TYPE: nucleic acid
(C) STRANDEDNESS: single
(D) TOPOLOGY: linear (xi) SEQUENCE DESCRIPTION: SEQ ID NO: 27:

ATGGAGATCT CGGACAACCC CGGCGTCCAT GAAGCAGGTG AGCCAGAGTT CAAG 54

(2) INFORMATION FOR SEQ ID NO: 28:

(i) SEQUENCE CHARACTERISTICS:
(A) LENGTH: 22 amino acids
(B) TYPE: amino acid
(D) TOPOLOGY: linear (ii) MOLECULE TYPE: peptide (xi) SEQUENCE DESCRIPTION: SEQ ID NO: 28:

Ser Leu Leu Ser His Glu Phe Gln Asp Glu Thr Asp Thr Glu Glu Glu
1 5 10 15

Thr Leu Tyr Ser Ala Lys
20

(2) INFORMATION FOR SEQ ID NO: 29:

(i) SEQUENCE CHARACTERISTICS:
(A) LENGTH: 66 base pairs
(B) TYPE: nucleic acid
(C) STRANDEDNESS: single
(D) TOPOLOGY: linear (xi) SEQUENCE DESCRIPTION: SEQ ID NO: 29:

-continued

```
AGYCTNCTNA GYCAYGARTT YCARGAYGAR ACNGAYACNG ARGARGARAC NCTNTAYAGY      60

GCNAAR                                                                 66
```

(2) INFORMATION FOR SEQ ID NO: 30:

(i) SEQUENCE CHARACTERISTICS:
(A) LENGTH: 66 base pairs
(B) TYPE: nucleic acid
(C) STRANDEDNESS: single
(D) TOPOLOGY: linear (xi) SEQUENCE DESCRIPTION: SEQ ID NO: 30:

```
TCNTTRTTRT CNCAYGARTT YCARGAYGAR ACNGAYACNG ARGARGARAC NTTRTAYTCN      60

GCNAAR                                                                 66
```

(2) INFORMATION FOR SEQ ID NO: 31:

(i) SEQUENCE CHARACTERISTICS:
(A) LENGTH: 61 base pairs
(B) TYPE: nucleic acid
(C) STRANDEDNESS: single
(D) TOPOLOGY: linear (xi) SEQUENCE DESCRIPTION: SEQ ID NO: 31:

```
TKYTNAGYCA YGARTTYCAR GATGAAACAG ACACTGAAGA AGARACNYTN TAYTCNGCVA      60

A                                                                      61
```

(2) INFORMATION FOR SEQ ID NO: 32:

(i) SEQUENCE CHARACTERISTICS:
(A) LENGTH: 45 base pairs
(B) TYPE: nucleic acid
(C) STRANDEDNESS: single
(D) TOPOLOGY: linear (xi) SEQUENCE DESCRIPTION: SEQ ID NO: 32:

```
TCCCTTTTGA GCCACGAATT CCAGGATGAA ACAGACACTG AAGAA                      45
```

(2) INFORMATION FOR SEQ ID NO: 33:

(i) SEQUENCE CHARACTERISTICS:
(A) LENGTH: 483 base pairs
(B) TYPE: nucleic acid
(C) STRANDEDNESS: single
(D) TOPOLOGY: linear (ii) MOLECULE TYPE: Genomic DNA (ix) FEATURE:
(A) NAME/KEY: Coding Sequence
(B) LOCATION: 1...483

(xi) SEQUENCE DESCRIPTION: SEQ ID NO: 33:

```
ATG GGG CAA CAT CCA GCA AAA TCA ATG GAC GTC AGA CGG ATA GAA GGA        48
Met Gly Gln His Pro Ala Lys Ser Met Asp Val Arg Arg Ile Glu Gly
  1               5                  10                  15

GGA GAA ATA CTG TTA AAC CAA CTT GCC GGA AGG ATG ATC CCA AAA GGG        96
Gly Glu Ile Leu Leu Asn Gln Leu Ala Gly Arg Met Ile Pro Lys Gly
             20                  25                  30

ACT TTG ACA TGG TCA GGC AAG TTT CCA ACA CTA GAT CAC GTG TTA GAC       144
Thr Leu Thr Trp Ser Gly Lys Phe Pro Thr Leu Asp His Val Leu Asp
         35                  40                  45

CAT GTG CAA ACA ATG GAG GAG ATA AAC ACC CTC CAG AAT CAG GGA GCT       192
His Val Gln Thr Met Glu Glu Ile Asn Thr Leu Gln Asn Gln Gly Ala
     50                  55                  60
```

-continued

```
TGG CCT GCT GGG GCG GGA AGG AGA GTA GGA TTA TCA AAT CCG ACT CCT       240
Trp Pro Ala Gly Ala Gly Arg Arg Val Gly Leu Ser Asn Pro Thr Pro
 65                 70                  75                  80

CAA GAG ATT CCT CAG CCC CAG TGG ACT CCC GAG GAA GAC CAA AAA GCA       288
Gln Glu Ile Pro Gln Pro Gln Trp Thr Pro Glu Glu Asp Gln Lys Ala
                85                  90                  95

CGC GAA GCT TTT CGC CGT TAT CAA GAA GAA AGA CCA CCG GAA ACC ACC       336
Arg Glu Ala Phe Arg Arg Tyr Gln Glu Glu Arg Pro Pro Glu Thr Thr
            100                 105                 110

ACC ATT CCT CCG TCT TCC CCT CCT CAG TGG AAG CTA CAA CCC GGG GAC       384
Thr Ile Pro Pro Ser Ser Pro Pro Gln Trp Lys Leu Gln Pro Gly Asp
        115                 120                 125

GAT CCA CTC CTG GGA AAT CAG TCT CTC CTC GAG ACT CAT CCG CTA TAC       432
Asp Pro Leu Leu Gly Asn Gln Ser Leu Leu Glu Thr His Pro Leu Tyr
    130                 135                 140

CAG TCA GAA CCA GCG GTG CCA GTG ATA AAA ACT CCC CCC TTG AAG AAG       480
Gln Ser Glu Pro Ala Val Pro Val Ile Lys Thr Pro Pro Leu Lys Lys
145                 150                 155                 160

AAA                                                                   483
Lys
```

(2) INFORMATION FOR SEQ ID NO: 34:

(i) SEQUENCE CHARACTERISTICS:
(A) LENGTH: 161 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 34:

```
Met Gly Gln His Pro Ala Lys Ser Met Asp Val Arg Arg Ile Glu Gly
  1               5                  10                  15

Gly Glu Ile Leu Leu Asn Gln Leu Ala Gly Arg Met Ile Pro Lys Gly
             20                  25                  30

Thr Leu Thr Trp Ser Gly Lys Phe Pro Thr Leu Asp His Val Leu Asp
        35                  40                  45

His Val Gln Thr Met Glu Glu Ile Asn Thr Leu Gln Asn Gln Gly Ala
     50                  55                  60

Trp Pro Ala Gly Ala Gly Arg Arg Val Gly Leu Ser Asn Pro Thr Pro
 65                 70                  75                  80

Gln Glu Ile Pro Gln Pro Gln Trp Thr Pro Glu Glu Asp Gln Lys Ala
                85                  90                  95

Arg Glu Ala Phe Arg Arg Tyr Gln Glu Glu Arg Pro Pro Glu Thr Thr
            100                 105                 110

Thr Ile Pro Pro Ser Ser Pro Pro Gln Trp Lys Leu Gln Pro Gly Asp
        115                 120                 125

Asp Pro Leu Leu Gly Asn Gln Ser Leu Leu Glu Thr His Pro Leu Tyr
    130                 135                 140

Gln Ser Glu Pro Ala Val Pro Val Ile Lys Thr Pro Pro Leu Lys Lys
145                 150                 155                 160

Lys
```

(2) INFORMATION FOR SEQ ID NO: 35:

(i) SEQUENCE CHARACTERISTICS:
(A) LENGTH: 174 amino acids

-continued (B) TYPE: amino acid
(D) TOPOLOGY: linear (ii) MOLECULE TYPE: protein (xi) SEQUENCE DESCRIPTION: SEQ ID NO: 35:

```
Met Gly Gly Trp Ser Ser Lys Pro Arg Lys Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Gly Ala Asn Ser Asn Asn Pro Asp Trp Asp Phe Asn Pro Val
         35                  40                  45

Lys Asp Asp Trp Pro Ala Ala Asn Gln Val Gly Val Gly Ala Phe Gly
     50                  55                  60

Pro Arg Leu Thr Pro Pro His Gly Gly Ile Leu Gly Trp Ser Pro Gln
 65                  70                  75                  80

Ala Gln Gly Ile Leu Thr Thr Val Ser Thr Ile Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn
                165                 170
```

(2) INFORMATION FOR SEQ ID NO: 36:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 36:

```
Met Gly Gly Trp Ser Ser Lys Pro Arg Lys Gly Met Gly Thr Asn Leu
  1               5                  10                  15

Ser Val Pro Asn Pro Leu Gly Phe Leu Pro Asp His Gln Leu Asp Pro
             20                  25                  30

Ala Phe Gly Ala Asn Ser Thr Asn Pro Asp Trp Asp Phe Asn Pro Ile
         35                  40                  45

Lys Asp His Trp Pro Ala Ala Asn Gln Val Gly Val Gly Ala Phe Gly
     50                  55                  60

Pro Gly Leu Thr Pro Pro His Gly Gly Ile Leu Gly Trp Ser Pro Gln
 65                  70                  75                  80

Ala Gln Gly Ile Leu Thr Thr Val Ser Thr Ile Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Leu His
        115                 120                 125

Gln Ala Leu Gln Asp Pro Arg Val Arg Gly Leu Tyr Leu Pro Ala Gly
    130                 135                 140
```

-continued

Gly Ser Ser Ser Gly Thr Val Asn Pro Ala Pro Asn Ile Ala Ser His
145 150 155 160

Ile Ser Ser Ile Ser Ala Arg Thr Gly Asp Pro Val Thr Ile
165 170

(2) INFORMATION FOR SEQ ID NO: 37:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 37:

Met Gly Gly Trp Ser Ser Lys Pro Arg Lys Gly Met Gly Thr Asn Leu
1 5 10 15

Ser Val Pro Asn Pro Leu Gly Phe Phe Pro Asp His Gln Leu Asp Pro
20 25 30

Ala Phe Gly Ala Asn Ser Asn Asn Pro Asp Trp Asp Phe Asn Pro Ile
35 40 45

Lys Asp His Trp Pro Gln Ala Asn Gln Val Gly Val Gly Ala Phe Gly
50 55 60

Pro Gly Phe Thr Pro Pro His Gly Gly Val Leu Gly Trp Ser Pro Gln
65 70 75 80

Ala Gln Gly Ile Leu Ala Thr Val Pro Ala Met Pro Pro Pro Ala Ser
85 90 95

Thr Asn Arg Gln Ser Gly Arg Gln Pro Thr Pro Ile Ser Pro Pro Leu
100 105 110

Arg Asp Ser His Pro Gln Ala Met Gln Trp Asn Ser Thr Ala Phe His
115 120 125

Gln Ala Leu Gln Asp Pro Arg Val Arg Gly Leu Tyr Phe Pro Ala Gly
130 135 140

Gly Ser Ser Ser Gly Thr Leu Asn Pro Val Pro Thr Ile Ala Ser His
145 150 155 160

Ile Ser Ser Ile Ser Ser Arg Ile Gly Asp Pro Ala Pro Asn
165 170

(2) INFORMATION FOR SEQ ID NO: 38:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 38:

Met Gly Gly Trp Ser Ser Lys Pro Arg Gln Gly Met Gly Thr Asn Leu
1 5 10 15

Ser Val Pro Asn Pro Leu Gly Phe Phe Pro Asp His Gln Leu Asp Pro
20 25 30

Ala Phe Lys Ala Asn Ser Asp Asn Pro Asp Trp Asp Leu Asn Pro His
35 40 45

Lys Asp Asn Trp Pro Asp Ser Asn Lys Val Gly Val Gly Ala Phe Gly
50 55 60

Pro Gly Phe Thr Pro Pro His Gly Gly Leu Leu Gly Trp Ser Pro Gln
65 70 75 80

Ala Gln Gly Ile Leu Thr Thr Val Pro Thr Ala Pro Pro Pro Ala Ser

-continued

```
                 85                  90                  95

Thr Asn Arg Gln Leu Gly Arg Lys Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
    130                 135                 140

Gly Ser Ser Ser Gly Thr Val Asn Pro Val Gln Asn Thr Val Ser Ser
145                 150                 155                 160

Ile Ser Ser Ile Leu Ser Lys Thr Gly Asp Pro Val Pro Asn
                165                 170
```

(2) INFORMATION FOR SEQ ID NO: 39:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 39:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Lys Ala Asn Ser Asp Asn Pro Asp Trp Asp Leu Asn Pro His
         35                  40                  45

Lys Asp Asn Trp Pro Asp Ser Asn Lys Val Gly Val Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Ile Leu Thr Thr Val Pro Thr Ala Pro Pro Pro Ala Ser
                 85                  90                  95

Thr Asn Arg Gln Leu Gly Arg Lys Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
    130                 135                 140

Gly Ser Ser Ser Gly Thr Val Asn Pro Val Gln Asn Thr Ala Ser Ser
145                 150                 155                 160

Ile Ser Ser Ile Leu Ser Thr Thr Gly Asp Pro Val Pro Asn
                165                 170
```

(2) INFORMATION FOR SEQ ID NO: 40:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 40:

```
Met Gly Gly Trp Ser Ser Lys Pro Arg Lys Gly Met Gly Thr Asn Leu
  1               5                  10                  15

Ser Val Pro Asn Pro Leu Gly Phe Phe Pro Asp His Gln Leu Asp Pro
             20                  25                  30
```

-continued

```
Ala Phe Lys Ala Asn Ser Glu Asn Pro Asp Trp Asp Leu Asn Pro Asn
        35                  40                  45

Lys Asp Asn Trp Pro Asp Ala Asn Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Leu Leu Thr Thr Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Gly Val Arg Ala Leu Tyr Phe Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn
                165                 170
```

(2) INFORMATION FOR SEQ ID NO: 41:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 41:

```
Met Gly Gly Trp Ser Ser Lys Pro Arg Lys Gly Met Gly Thr Asn Leu
  1               5                  10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Ser Ser Val Pro Ala Ala Pro Pro Pro Ala Ser
                85                  90                  95

Thr Asn Arg Gln Ser Gly Arg Gln Pro Ile Pro Leu Ser Pro Pro Leu
            100                 105                 110

Arg Asp Thr His Pro Gln Ala Met Gln Trp Asn Ser Thr Thr Phe His
        115                 120                 125

Gln Thr Leu Gln Asp Pro Arg Val Arg Ala Leu Tyr Phe Pro Ala Gly
    130                 135                 140

Gly Ser Ser Ser Gly Thr Val Ser Pro Ala Gln Asn Thr Val Ser Ala
145                 150                 155                 160

Ile Ser Ser Ile Leu Ser Lys Thr Gly Asp Pro Val Pro Asn
                165                 170
```

(2) INFORMATION FOR SEQ ID NO: 42:

(i) SEQUENCE CHARACTERISTICS:
(A) LENGTH: 174 amino acids
(B) TYPE: amino acid

-continued (D) TOPOLOGY: linear (ii) MOLECULE TYPE: protein (xi) SEQUENCE DESCRIPTION: SEQ ID NO: 42:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Gly Ala Asn Ser Asn Asn Pro Asp Trp Asp Phe Asn Pro Asn
         35                  40                  45

Lys Asp His Trp Pro Glu Ala Asn Gln Val Gly Ala Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Ile Leu Thr Thr Val Pro Ala Ala Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Thr Glu Ser Arg Thr Gly Asp Pro Ala Pro Asn
                165                 170
```

(2) INFORMATION FOR SEQ ID NO: 43:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 43:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Gly Ala Asn Ser Asn Asn Pro Asp Trp Asp Phe Asn Pro Asn
         35                  40                  45

Lys Asp His Trp Pro Glu Ala Asn Gln Val Gly Ala Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Ile Leu Thr Thr Val Pro Ala Ala Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
```

-continued 145 150 155 160

Ile Ser Ser Ile Ser Phe Ser Thr Gly Asp Pro Ala Pro Asn
165 170

(2) INFORMATION FOR SEQ ID NO: 44:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 44:

Met Gly Gly Trp Ser Ser Lys Pro Arg Gln Gly Met Gly Thr Asn Leu
1 5 10 15

Ser Val Pro Asn Pro Leu Gly Phe Phe Pro Asp His Gln Leu Asp Pro
20 25 30

Ala Phe Gly Ala Asn Ser Asn Asn Pro Asp Trp Asp Phe Asn Pro Asn
35 40 45

Lys Asp His Trp Pro Glu Ala Ile Lys Val Gly Ala Gly Asp Phe Gly
50 55 60

Pro Gly Phe Thr Pro Pro His Gly Gly Leu Leu Gly Trp Ser Pro Gln
65 70 75 80

Ala Gln Gly Ile Leu Thr Thr Val Pro Ala Ala Pro Pro Pro Val Ser
85 90 95

Thr Asn Arg Gln Ser Gly Arg Gln Pro Thr Pro Ile Ser Pro Pro Leu
100 105 110

Arg Asp Ser His Pro Gln Ala Met Gln Trp Asn Ser Thr Thr Phe His
115 120 125

Gln Ala Leu Leu Asp Pro Arg Val Arg Gly Leu Tyr Phe Pro Ala Gly
130 135 140

Gly Ser Ser Ser Gly Thr Val Asn Pro Val Pro Thr Thr Val Ser Pro
145 150 155 160

Ile Ser Ser Ile Ser Phe Ser Thr Gly Asp Pro Ala Pro Asn
165 170

(2) INFORMATION FOR SEQ ID NO: 45:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 45:

Met Gly Gly Trp Ser Ser Lys Pro Arg Gln Gly Met Gly Thr Asn Leu
1 5 10 15

Ser Val Pro Asn Pro Leu Gly Phe Phe Pro Asp His Gln Leu Asp Pro
20 25 30

Ala Phe Gly Ala Asn Ser His Asn Pro Asp Trp Asp Phe Asn Pro Asn
35 40 45

Lys His Asp Trp Pro Glu Ala Asn Gln Val Gly Ala Gly Ala Phe Gly
50 55 60

Pro Gly Phe Thr Pro Pro His Gly Gly Leu Leu Gly Trp Ser Pro Gln
65 70 75 80

Ala Gln Gly Val Leu Thr Thr Val Pro Val Ala Pro Pro Pro Ala Ser
85 90 95

-continued

```
Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Ser Ser Arg Thr Gly Asp Pro Ala Pro Asn
                165                 170
```

(2) INFORMATION FOR SEQ ID NO: 46:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 46:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Gly Ala Asn Ser Asn Asn Pro Asp Trp Asp Phe Asn Pro Asn
         35                  40                  45

Lys Asp Gln Trp Pro Glu Ala Asn Gln Val Gly Ala Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Ile Leu Thr Thr Val Pro Ala Ala Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn
                165                 170
```

(2) INFORMATION FOR SEQ ID NO: 47:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 47:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
             20                  25                  30
```

-continued

```
Ala Phe Gly Ala Asn Ser Asn Asn Pro Asp Trp Asp Phe Asn Pro Asn
        35                  40                  45

Lys Asp Arg Trp Pro Glu Ala Asn Gln Val Gly Ala Gly Ala Phe Gly
    50                  55                  60

Pro Gly Tyr Pro Pro Pro His Gly Gly Leu Leu Gly Trp Ser Pro Gln
 65                 70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Val Gln Gln Asp Pro Arg Val Arg Gly Leu Tyr Phe Pro Pro Gly
    130                 135                 140

Gly Ser Ser Ser Gly Thr Val Asn Pro Val Pro Thr Thr Ala Ser Pro
145                 150                 155                 160

Ile Ser Ser Ile Ser Ser Arg Thr Gly Asp Pro Ala Pro Asn
                165                 170
```

(2) INFORMATION FOR SEQ ID NO: 48:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 48:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Ala Gly Ala Phe Gly
    50                  55                  60

Pro Gly Phe Thr Pro Pro His Gly Gly Leu Leu Gly Trp Ser Pro Gln
 65                 70                  75                  80

Ala Gln Gly Ile Leu Thr Thr Val Pro Val Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Leu Leu Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn
                165                 170
```

(2) INFORMATION FOR SEQ ID NO: 49:

(i) SEQUENCE CHARACTERISTICS:
(A) LENGTH: 170 amino acids
(B) TYPE: amino acid
(D) TOPOLOGY: linear -continued (ii) MOLECULE TYPE: protein (xi) SEQUENCE DESCRIPTION: SEQ ID NO: 49:

```
Met Gly Gly Trp Ser Ser Lys Pro Arg Gln Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Gly Ala Asn Ser Asn Asn Pro Asp Trp Asp Phe Asn Pro Asn
         35                  40                  45

Lys Asp His Trp Pro Ala Glu Asn Gln Val Gly Ala Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Ile Leu Thr Thr Leu Pro Ala Ala Pro Pro Pro Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
        115                 120                 125

Gln Ala Arg Val Arg Gly Leu Tyr Phe Pro Ala Gly Gly Ser Ser Ser
    130                 135                 140

Gly Thr Val Asn Pro Val Pro Thr Thr Ala Ser Pro Ile Ser Ser Ile
145                 150                 155                 160

Phe Ser Arg Thr Gly Asp Pro Ala Pro Asn
                165                 170
```

(2) INFORMATION FOR SEQ ID NO: 50:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 50:

```
Met Gly Gly Trp Ser Ser Lys Pro Arg Lys Gly Met Gly Thr Asn Leu
  1               5                  10                  15

Ser Val Pro Asn Pro Leu Gly Phe Phe Pro Asp His Gln Leu Asp Pro
             20                  25                  30

Ala Phe Gly Ala Asn Ser Asn Asn Pro Asp Trp Asp Phe Asn Pro Asn
         35                  40                  45

Lys Asp His Trp Pro Glu Ala Asn Gln Val Gly Ala Gly Ala Phe Gly
     50                  55                  60

Pro Gly Phe Thr Pro Pro His Gly Leu Ile Leu Gly Trp Ser Pro Gln
 65                  70                  75                  80

Ala Gln Gly Ile Leu Thr Thr Val Pro Ala Ala Pro Pro Ser Ala Ser
                 85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe Gln
        115                 120                 125

Gln Ala Leu Gln Asp Pro Arg Val Arg Val Leu Tyr Phe Pro Ala Gly
    130                 135                 140

Gly Ser Ser Ser Gly Thr Val Asn Pro Val Pro Thr Thr Ala Ser Leu
145                 150                 155                 160
```

-continued

Ile Ser Ser Ile Phe Ser Arg Ile Gly Asp Pro Val Thr Asn
165 170

(2) INFORMATION FOR SEQ ID NO: 51:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 51:

Met Gly Gly Trp Ser Ser Lys Pro Arg Lys Gly Met Gly Thr Asn Leu
1 5 10 15

Ser Val Pro Asn Pro Leu Gly Phe Phe Pro Asp His Gln Leu Asp Pro
20 25 30

Ala Phe Gly Ala Asn Ser Asn Asn Pro Asp Trp Asp Phe Asn Pro Asn
35 40 45

Lys Asp Gln Trp Pro Glu Ala Asn Gln Val Gly Ala Gly Ala Phe Gly
50 55 60

Pro Gly Phe Thr Pro Pro His Gly Gly Leu Leu Gly Trp Ser Pro Gln
65 70 75 80

Ala Gln Gly Ile Leu Thr Thr Leu Pro Ala Ala Pro Pro Pro Ala Ser
85 90 95

Thr Asn Arg Gln Ser Gly Arg Gln Pro Thr Pro Ile Ser Pro Pro Leu
100 105 110

Arg Asp Ser His Pro Gln Ala Met Gln Trp Asn Ser Thr Thr Phe Gln
115 120 125

Gln Ala Leu Leu Asp Pro Arg Val Arg Gly Leu Tyr Phe Pro Ala Gly
130 135 140

Gly Ser Ser Ser Gly Thr Val Asn Pro Val Pro Thr Thr Ala Ser Leu
145 150 155 160

Ile Ser Ser Ile Ser Phe Ser Thr Gly Asp Pro Val Thr Asn
165 170

(2) INFORMATION FOR SEQ ID NO: 52:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 52:

Met Gly Gly Trp Ser Ser Lys Pro Arg Lys Gly Met Gly Gln Asn Leu
1 5 10 15

Ser Thr Ser Asn Pro Leu Gly Phe Phe Pro Asp His Gln Leu Asp Pro
20 25 30

Ala Phe Arg Ala Asn Thr Ala Asn Pro Asp Trp Asp Phe Asn Pro Asn
35 40 45

Lys Asp Thr Trp Pro Asp Ala Asn Lys Val Gly Ala Gly Ala Phe Gly
50 55 60

Leu Gly Phe Thr Pro Pro His Gly Gly Leu Leu Gly Trp Ser Pro Gln
65 70 75 80

Ala Gln Gly Ile Leu Glu Leu Pro Ala Asn Ile Pro Pro Pro Ala Ser
85 90 95

-continued

```
Thr Asn Arg Gln Ser Gly Arg Gln Pro Thr Pro Leu Ser Pro Pro Leu
            100                 105                 110

Arg Asn Thr His Pro Gln Ala Met Gln Trp Asn Ser Thr Ala Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Thr Asn
                165                 170
```

(2) INFORMATION FOR SEQ ID NO: 53:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 53:

```
Met Gly Gly Trp Ser Ser Lys Pro Arg Lys Gly Met Gln Thr Asn Leu
  1               5                  10                  15

Ser Thr Ser Asn Pro Leu Gly Phe Phe Pro Asp His Gln Leu Asp Pro
            20                  25                  30

Ala Phe Arg Ala Asn Thr Ala Asn Pro Asp Trp Asp Phe Asn Pro Asn
        35                  40                  45

Lys Asp Thr Trp Pro Asp Ala Asn Lys Val Gly Ala Gly Ala Phe Gly
    50                  55                  60

Leu Gly Leu Thr Pro Pro His Gly Gly Leu Leu Gly Trp Ser Pro Gln
 65                  70                  75                  80

Ala Gln Gly Ile Leu Gln Thr Val Pro Ala Asn Pro Pro Pro Ala Ser
                85                  90                  95

Thr Asn Arg Thr Ser Gly Arg Gln Pro Thr Pro Leu Ser Pro Pro Leu
            100                 105                 110

Arg Asp Ser Thr Pro Gln Ala Met Gln Trp Asn Ser Thr Thr Phe His
        115                 120                 125

Gln Thr Leu Gln Asp Pro Arg Val Arg Gly Leu Tyr Pro Pro Ala Gly
    130                 135                 140

Gly Ser Ser Ser Gly Thr Val Asn Pro Val Pro Asn Thr Thr Val His
145                 150                 155                 160

Ile Ser Ser Ile Phe Thr Arg Ile Gly Asp Pro Ala Leu Asn
                165                 170
```

(2) INFORMATION FOR SEQ ID NO: 54:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 54:

```
Met Gly Gly Trp Ser Ser Lys Pro Arg Lys Gly Met Gln Thr Asn Leu
  1               5                  10                  15

Thr Ser Pro Asn Pro Leu Gly Phe Phe Pro Asp His Gln Leu Asp Pro
            20                  25                  30

Ala Phe Arg Ala Asn Thr Ala Asn Pro Asp Trp Asp Phe Asn Pro Asn
```

-continued

```
        35                  40                  45

Lys Asp Ser Trp Pro Asp Ala Asn Lys Val Gly Ala Gly Ala Phe Gly
     50                  55                  60

Leu Gly Phe Thr Pro Pro His Gly Gly Leu Leu Gly Trp Ser Pro Gln
 65                  70                  75                  80

Ala Gln Gly Ile Leu Gln Thr Leu Pro Ala Asn Pro Pro Pro Ala Ser
                 85                  90                  95

Thr Asn Arg Gln Ser Gly Arg Gln Pro Thr Pro Leu Ser Pro Pro Leu
            100                 105                 110

Arg Asn Thr His Pro Gln Ala Met Gln Trp Asn Ser Thr Thr Phe His
        115                 120                 125

Gln Thr Leu Gln Asp Pro Arg Val Arg Gly Leu Tyr Leu Pro Ala Gly
    130                 135                 140

Gly Ser Ser Ser Gly Thr Val Asn Pro Val Pro Thr Thr Val Ser Pro
145                 150                 155                 160

Ile Ser Ser Ile Phe Ser Arg Thr Ile Asp Pro Ala Leu Asn
                165                 170
```

(2) INFORMATION FOR SEQ ID NO: 55:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 55:

```
Met Gly Gly Trp Ser Ser Lys Pro Arg Lys Gly Met Gly Gln Asn Leu
  1               5                  10                  15

Ser Thr Ser Asn Pro Leu Gly Phe Phe Pro Asp His Gln Leu Asp Pro
             20                  25                  30

Ala Phe Arg Ala Asn Thr Asn Asn Pro Asp Trp Asp Phe Asn Pro Asn
         35                  40                  45

Lys Asp Thr Trp Pro Asp Ala Asn Lys Val Gly Ala Gly Ala Phe Gly
     50                  55                  60

Leu Gly Phe Thr Pro Pro His Gly Gly Leu Leu Gly Trp Ser Pro Gln
 65                  70                  75                  80

Ala Gln Gly Ile Ile Gln Thr Leu Pro Ala Asn Pro Pro Pro Ala Ser
                 85                  90                  95

Thr Asn Arg Gln Ser Gly Arg Gln Pro Thr Pro Leu Ser Pro Pro Leu
            100                 105                 110

Arg Thr Thr His Pro Gln Ala Met Gln Trp Asn Ser Thr Thr Phe His
        115                 120                 125

Gln Thr Leu Gln Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160

Ile Ser Ser Ile Phe Ser Arg Ile Gly Asp Pro Ala Leu Asn
                165                 170
```

(2) INFORMATION FOR SEQ ID NO: 56:

(i) SEQUENCE CHARACTERISTICS:
(A) LENGTH: 174 amino acids
(B) TYPE: amino acid
(D) TOPOLOGY: linear -continued (ii) MOLECULE TYPE: protein (xi) SEQUENCE DESCRIPTION: SEQ ID NO: 56:

```
Met Gly Gly Trp Ser Ser Lys Pro Arg Lys Gly Met Gly Gln Asn Leu
  1               5                  10                  15

Ser Thr Ser Asn Pro Leu Gly Phe Phe Pro Asp His Gln Leu Asp Pro
             20                  25                  30

Ala Phe Arg Ala Asn Thr Ala Asn Pro Asp Trp Asp Phe Asn Pro Asn
         35                  40                  45

Lys Asp Thr Trp Pro Asp Ala Asn Lys Val Gly Ala Gly Ala Phe Gly
     50                  55                  60

Leu Gly Phe Thr Pro Pro His Gly Gly Leu Leu Gly Trp Ser Pro Gln
 65                  70                  75                  80

Ala Gln Gly Ile Leu Gln Thr Val Pro Ala Asn Pro Pro Pro Ala Ser
                 85                  90                  95

Thr Asn Arg Gln Ser Gly Arg Gln Pro Thr Pro Leu Ser Pro Pro Leu
            100                 105                 110

Arg Asp Ala His Pro Gln Ala Met Gln Trp Asn Ser Thr Thr Phe His
        115                 120                 125

Gln Thr Leu Gln Asp Pro Arg Val Arg Gly Leu Tyr Phe Pro Ala Gly
    130                 135                 140

Gly Ser Ser Ser Gly Thr Val Asn Pro Val Leu Thr Thr Ala Ser Pro
145                 150                 155                 160

Leu Ser Ser Ile Phe Ser Arg Ile Gly Asp Leu Ala Pro Asn
                165                 170
```

(2) INFORMATION FOR SEQ ID NO: 57:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 57:

```
Met Gly Gly Trp Ser Ser Lys Pro Arg Lys Gly Met Gly Gln Asn Leu
  1               5                  10                  15

Ser Thr Ser Asn Pro Leu Gly Phe Phe Pro Asp His Gln Leu Asp Pro
             20                  25                  30

Ala Phe Arg Ala Asn Thr Arg Asn Pro Asp Trp Asp Phe Asn Pro Asn
         35                  40                  45

Lys Asp Thr Trp Pro Asp Ala Asn Lys Val Gly Ala Gly Ala Phe Gly
     50                  55                  60

Leu Gly Phe Thr Pro Pro His Gly Gly Leu Leu Gly Trp Ser Pro Gln
 65                  70                  75                  80

Ala Gln Gly Ile Leu Gln Thr Leu Pro Ala Asn Pro Pro Pro Ala Ala
                 85                  90                  95

Thr Asn Arg Gln Ser Gly Arg Gln Pro Thr Pro Leu Ser Pro Pro Leu
            100                 105                 110

Arg Asp Ala His Pro Gln Ala Met Gln Trp Thr Ser Thr Thr Phe His
        115                 120                 125

Gln Ala Leu Gln Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Pro
145                 150                 155                 160
```

-continued

```
Ile Leu Ser Ile Phe Ser Lys Ile Gly Asp Leu Ala Pro Asn
                165                 170
```

(2) INFORMATION FOR SEQ ID NO: 58:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 58:

```
Met Gly Leu Ser Trp Thr Val Pro Leu Glu Gly Trp Gly Lys Asn His
  1               5                  10                  15

Ser Thr Thr Asn Pro Leu Gly Phe Phe Pro Asp His Gln Leu Asp Pro
             20                  25                  30

Ala Phe Arg Ala Asn Thr Arg Asn Pro Asp Trp Asp His Asn Pro Asn
        35                  40                  45

Lys Asp His Trp Thr Glu Ala Asn Lys Val Gly Val Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Ile Met Lys Thr Leu Pro Ala Asp Pro Pro Pro Ala Ser
                 85                  90                  95

Thr Asn Arg Gln Ser Gly Arg Gln Pro Ile Pro Ile Thr Pro Pro Leu
            100                 105                 110

Arg Asp Ser Thr Pro Gln Ala Met Gln Trp Asn Ser Thr Thr Phe His
        115                 120                 125

Gln Ala Leu Gln Asp Pro Arg Val Arg Gly Leu Tyr Leu Phe Ala Gly
    130                 135                 140

Gly Ser Ser Ser Gly Thr Val Asn Pro Val Pro Thr Thr Ala Ser Leu
145                 150                 155                 160

Ile Ser Ser Ile Phe Ser Arg Ile Gly Asp Pro Ala Pro Asn
                165                 170
```

(2) INFORMATION FOR SEQ ID NO: 59:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 59:

```
Met Gly Leu Ser Trp Thr Val Pro Leu Glu Gly Trp Gly Lys Asn His
  1               5                  10                  15

Ser Thr Thr Asn Pro Leu Gly Phe Phe Pro Asp His Gln Leu Asp Pro
             20                  25                  30

Ala Phe Arg Ala Asn Ser Thr Arg Pro Asp Trp Asp Phe His Pro Asn
        35                  40                  45

Lys Asp His Trp Thr Glu Ala Asn Lys Val Gly Val Gly Ala Phe Gly
     50                  55                  60

Pro Gly Phe Thr Pro Pro His Gly Gly Leu Leu Gly Trp Ser Pro Gln
 65                  70                  75                  80

Ala Gln Gly Met Leu Lys Thr Leu Pro Ala Asp Pro Pro Pro Ala Ser
                 85                  90                  95

Thr Asn Arg Gln Ser Gly Arg Gln Pro Thr Pro Ile Thr Pro Pro Leu
```

-continued

```
            100                 105                 110

Arg Asp Ser His Pro Gln Ala Met Gln Trp Asn Ser Thr Thr Phe His
        115                 120                 125

Gln Ala Leu Gln Asp Pro Arg Val Arg Gly Leu Tyr Phe Pro Ala Gly
    130                 135                 140

Gly Ser Ser Ser Gly Thr Val Asn Pro Val Pro Thr Thr Ala Ser Leu
145                 150                 155                 160

Ile Ser Ser Ile Phe Ser Arg Thr Ile Asp Pro Ala Pro Asn
                165                 170
```

(2) INFORMATION FOR SEQ ID NO: 60:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 60:

```
Met Gly Ala Pro Leu Ser Thr Thr Arg Arg Gly Met Gly Gln Asn Leu
  1               5                  10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Lys Asn
        35                  40                  45

Lys Asp Thr Trp Pro Met Ala Asn Lys Val Gly Val Gly Gly Tyr Gly
    50                  55                  60

Pro Gly Phe Thr Pro Pro His Gly Gly Leu Leu Gly Trp Ser Pro Gln
 65                  70                  75                  80

Ala Gln Gly Val Leu Thr Thr Leu Pro Ala Asp Pro Pro Pro Ala Ser
                 85                  90                  95

Thr Asn Arg Leu Ser Gly Arg Lys Pro Thr Pro Val Ser Pro Pro Leu
            100                 105                 110

Arg Asp Ser Thr Pro Gln Ala Met Gln Trp Asn Ser Thr His Phe His
        115                 120                 125

Gln Ala Leu Leu Asp Pro Arg Val Arg Ala Leu Tyr Phe Pro Ala Gly
    130                 135                 140

Gly Ser Ser Ser Gly Thr Gln Asn Pro Ala Pro Thr Ile Ala Ser Leu
145                 150                 155                 160

Thr Ser Ser Ile Ser Ser Lys Thr Gly Gly Pro Ala Met Asn
                165                 170
```

(2) INFORMATION FOR SEQ ID NO: 61:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 61:

```
Met Gly Ala Pro Leu Ser Thr Thr Arg Arg Gly Met Gly Thr Asn Leu
  1               5                  10                  15

Ser Val Pro Asn Pro Leu Gly Phe Leu Pro Asp His Gln Leu Asp Pro
            20                  25                  30

Leu Phe Arg Ala Asn Ser Ser Ser Pro Asp Trp Asp Phe Asn Thr Asn
        35                  40                  45
```

-continued

```
Lys Asp Ser Trp Pro Met Ala Asn Lys Val Gly Val Gly Ala Gly Tyr
     50                  55                  60

Pro Gly Phe Thr Pro Pro His Gly Gly Leu Leu Gly Trp Ser Pro Gln
 65                  70                  75                  80

Ala Gln Gly Val Leu Thr Thr Leu Pro Ala Asp Pro Pro Pro Ala Ser
                 85                  90                  95

Thr Asn Arg Gln Leu Gly Arg Gln Lys Thr Gln Val Ser Pro Pro Leu
            100                 105                 110

Arg Asp Thr His Pro Gln Ala Met Gln Trp Asn Ser Thr His Phe His
        115                 120                 125

Gln Ala Leu Leu Asp Pro Arg Val Arg Ala Leu Tyr Phe Pro Ala Gly
    130                 135                 140

Gly Ser Ser Ser Gly Thr Gln Asn Pro Ala Pro Thr Ile Ala Ser Leu
145                 150                 155                 160

Thr Ser Ser Ile Ser Ser Lys Thr Gly Gly Pro Ala Met Asn
                165                 170
```

(2) INFORMATION FOR SEQ ID NO: 62:

(i) SEQUENCE CHARACTERISTICS:
(A) LENGTH: 174 amino acids
(B) TYPE: amino acid
(D) TOPOLOGY: linear (ii) MOLECULE TYPE: protein (xi) SEQUENCE DESCRIPTION: SEQ ID NO: 62:

```
Met Gly Gly Trp Ser Ser Lys Pro Arg Lys Gly Met Gly Gln Asn Leu
  1               5                  10                  15

Ser Thr Ser Asn Pro Leu Gly Phe Phe Pro Glu His Gln Leu Asp Pro
             20                  25                  30

Ala Phe Lys Ala Asn Ser Thr Asn Pro Asp Trp Asp Phe Asn Pro Lys
         35                  40                  45

Lys Asp Tyr Trp Pro Glu Ala Thr Lys Val Gly Ala Gly Ala Phe Gly
     50                  55                  60

Pro Gly Phe Thr Pro Pro His Gly Gly Leu Leu Gly Leu Ser Pro Gln
 65                  70                  75                  80

Ala Gln Gly Ile Leu Thr Thr Leu Pro Ala Asn Pro Pro Pro Ala Ser
                 85                  90                  95

Thr Asn Arg Gln Ser Gly Arg Gln Pro Thr Pro Leu Ser Pro Pro Leu
            100                 105                 110

Arg Asp Thr His Pro Gln Ala Met Gln Trp Asn Ser Thr Thr Phe His
        115                 120                 125

Gln Ala Leu Gln Asp Pro Arg Val Arg Gly Leu Tyr Phe Pro Ala Gly
    130                 135                 140

Gly Ser Ser Ser Gly Thr Leu Asn Pro Val Pro Asn Thr Ala Ser His
145                 150                 155                 160

Ile Ser Ser Val Phe Ser Thr Thr Gly Asp Pro Ala Pro Asn
                165                 170
```

(2) INFORMATION FOR SEQ ID NO: 63:

(i) SEQUENCE CHARACTERISTICS:
(A) LENGTH: 1116 base pairs
(B) TYPE: nucleic acid
(C) STRANDEDNESS: single
(D) TOPOLOGY: linear -continued

```
    (ii) MOLECULE TYPE: Genomic DNA

    (ix) FEATURE:
          (A) NAME/KEY: Coding Sequence
          (B) LOCATION: 1...1116

    (xi) SEQUENCE DESCRIPTION: SEQ ID NO: 63:

ATG GAG ATC TCG GAC AAC CCC GGT GTT CAT GAA GCA GGT GAG CCA GAG        48
Met Glu Ile Ser Asp Asn Pro Gly Val His Glu Ala Gly Glu Pro Glu
  1               5                  10                  15

TTC AAG TAT ATT GGT AAC ATG CAT GGG AAT GAA GTT GTG GGG CGA GAG        96
Phe Lys Tyr Ile Gly Asn Met His Gly Asn Glu Val Val Gly Arg Glu
             20                  25                  30

CTG CTC CTG AAC CTC ATC GAG TAC CTC TGC AAG AAC TTC GGC ACA GAT       144
Leu Leu Leu Asn Leu Ile Glu Tyr Leu Cys Lys Asn Phe Gly Thr Asp
         35                  40                  45

CCC GAA GTG ACT GAC TTG GTC CAG AGC ACG CGG ATC CAC ATC ATG CCG       192
Pro Glu Val Thr Asp Leu Val Gln Ser Thr Arg Ile His Ile Met Pro
     50                  55                  60

TCC ATG AAC CCA GAT GGC TAC GAG AAG TCC CAG GAA GGA GAC AGA GGA       240
Ser Met Asn Pro Asp Gly Tyr Glu Lys Ser Gln Glu Gly Asp Arg Gly
 65                  70                  75                  80

GGC ACC GTT GGC AGA AAT AAC AGC AAC AAC TAC GAC CTG AAC CGG AAC       288
Gly Thr Val Gly Arg Asn Asn Ser Asn Asn Tyr Asp Leu Asn Arg Asn
                 85                  90                  95

TTC CCA GAT CAG TTC TTC CAG GTG ACA GAC CCT CCG CAG CCA GAA ACT       336
Phe Pro Asp Gln Phe Phe Gln Val Thr Asp Pro Pro Gln Pro Glu Thr
            100                 105                 110

CTT GCT GTC ATG AGC TGG TTG AAA ACT TAC CCG TTC GTG CTT TCA GCA       384
Leu Ala Val Met Ser Trp Leu Lys Thr Tyr Pro Phe Val Leu Ser Ala
        115                 120                 125

AAC CTG CAT GGA GGT TCT CTG GTG GTT AAT TAC CCT TTT GAT GAC GAT       432
Asn Leu His Gly Gly Ser Leu Val Val Asn Tyr Pro Phe Asp Asp Asp
    130                 135                 140

GAA CAA GGA ATA GCC ATA TAC AGT AAA TCC CCA GAC GAT GCT GTG TTT       480
Glu Gln Gly Ile Ala Ile Tyr Ser Lys Ser Pro Asp Asp Ala Val Phe
145                 150                 155                 160

CAG CAG CTG GCA CTT TCC TAC TCC AAG GAA AAC AAA AAG ATG TAT CAG       528
Gln Gln Leu Ala Leu Ser Tyr Ser Lys Glu Asn Lys Lys Met Tyr Gln
                165                 170                 175

GGA AGC CCT TGT AAG GAT TTG TAC CCC ACA GAG TAC TTT CCA CAT GGC       576
Gly Ser Pro Cys Lys Asp Leu Tyr Pro Thr Glu Tyr Phe Pro His Gly
            180                 185                 190

ATC ACG AAC GGG GCC CAG TGG TAC AAC GTT CCA GGT GGG ATG CAG GAC       624
Ile Thr Asn Gly Ala Gln Trp Tyr Asn Val Pro Gly Gly Met Gln Asp
        195                 200                 205

TGG AAT TAC TTA AAT ACC AAC CTG TTT GAA GTG ACC ATT GAG CTG GGC       672
Trp Asn Tyr Leu Asn Thr Asn Leu Phe Glu Val Thr Ile Glu Leu Gly
    210                 215                 220

TGT GTG AAA TAC CCA AAA GCA GAG GAG CTG CCG AAG TAC TGG GAG CAG       720
Cys Val Lys Tyr Pro Lys Ala Glu Glu Leu Pro Lys Tyr Trp Glu Gln
225                 230                 235                 240

AAC CGT AGA TCT CTC CTC CAG TTC ATT AAA CAG GTT CAC CGC GGC ATC       768
Asn Arg Arg Ser Leu Leu Gln Phe Ile Lys Gln Val His Arg Gly Ile
                245                 250                 255

TGG GGA TTT GTG CTG GAT GCC ACG GAC GGA AGG GGC ATT CTC AAC GCC       816
Trp Gly Phe Val Leu Asp Ala Thr Asp Gly Arg Gly Ile Leu Asn Ala
            260                 265                 270

ACC ATC AGC GTC GCC GAC ATC AAC CAC CCC GTG ACC ACC TAC AAA GAT       864
Thr Ile Ser Val Ala Asp Ile Asn His Pro Val Thr Thr Tyr Lys Asp
        275                 280                 285
```

-continued

```
GGG GAC TAC TGG CGC CTC TTG GTC CAG GGG ACG TAC AAA GTC ACA GCA      912
Gly Asp Tyr Trp Arg Leu Leu Val Gln Gly Thr Tyr Lys Val Thr Ala
    290                 295                 300

TCT GCC CGA GGG TAT GAT CCA GTC ACT AAA ACG GTG GAA GTC GAC AGC      960
Ser Ala Arg Gly Tyr Asp Pro Val Thr Lys Thr Val Glu Val Asp Ser
305                 310                 315                 320

AAA GGT GGG GTG CAG GTC AAC TTC ACT CTT TCA CGG ACA GAC GCC AAA     1008
Lys Gly Gly Val Gln Val Asn Phe Thr Leu Ser Arg Thr Asp Ala Lys
                325                 330                 335

GTG GAG GAG GGG AAG GTG CCA GTC CTG AAC ACC CCA GAC ACC AGC GAC     1056
Val Glu Glu Gly Lys Val Pro Val Leu Asn Thr Pro Asp Thr Ser Asp
            340                 345                 350

CCC AAC GAG AAG GAG TTT GAG ACT CTG ATC AAA GAT CTA TCT GCT GAA     1104
Pro Asn Glu Lys Glu Phe Glu Thr Leu Ile Lys Asp Leu Ser Ala Glu
        355                 360                 365

AAC GGC CTG GAG                                                     1116
Asn Gly Leu Glu
    370
```

(2) INFORMATION FOR SEQ ID NO: 64:

(i) SEQUENCE CHARACTERISTICS:
(A) LENGTH: 372 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 64:

```
Met Glu Ile Ser Asp Asn Pro Gly Val His Glu Ala Gly Glu Pro Glu
  1               5                  10                  15

Phe Lys Tyr Ile Gly Asn Met His Gly Asn Glu Val Val Gly Arg Glu
             20                  25                  30

Leu Leu Leu Asn Leu Ile Glu Tyr Leu Cys Lys Asn Phe Gly Thr Asp
        35                  40                  45

Pro Glu Val Thr Asp Leu Val Gln Ser Thr Arg Ile His Ile Met Pro
     50                  55                  60

Ser Met Asn Pro Asp Gly Tyr Glu Lys Ser Gln Glu Gly Asp Arg Gly
 65                  70                  75                  80

Gly Thr Val Gly Arg Asn Asn Ser Asn Asn Tyr Asp Leu Asn Arg Asn
                 85                  90                  95

Phe Pro Asp Gln Phe Phe Gln Val Thr Asp Pro Pro Gln Pro Glu Thr
            100                 105                 110

Leu Ala Val Met Ser Trp Leu Lys Thr Tyr Pro Phe Val Leu Ser Ala
        115                 120                 125

Asn Leu His Gly Gly Ser Leu Val Val Asn Tyr Pro Phe Asp Asp Asp
    130                 135                 140

Glu Gln Gly Ile Ala Ile Tyr Ser Lys Ser Pro Asp Asp Ala Val Phe
145                 150                 155                 160

Gln Gln Leu Ala Leu Ser Tyr Ser Lys Glu Asn Lys Lys Met Tyr Gln
                165                 170                 175

Gly Ser Pro Cys Lys Asp Leu Tyr Pro Thr Glu Tyr Phe Pro His Gly
            180                 185                 190

Ile Thr Asn Gly Ala Gln Trp Tyr Asn Val Pro Gly Gly Met Gln Asp
        195                 200                 205

Trp Asn Tyr Leu Asn Thr Asn Leu Phe Glu Val Thr Ile Glu Leu Gly
```

-continued

```
    210                 215                 220

Cys Val Lys Tyr Pro Lys Ala Glu Glu Leu Pro Lys Tyr Trp Glu Gln
225                 230                 235                 240

Asn Arg Arg Ser Leu Leu Gln Phe Ile Lys Gln Val His Arg Gly Ile
                245                 250                 255

Trp Gly Phe Val Leu Asp Ala Thr Asp Gly Arg Gly Ile Leu Asn Ala
            260                 265                 270

Thr Ile Ser Val Ala Asp Ile Asn His Pro Val Thr Thr Tyr Lys Asp
        275                 280                 285

Gly Asp Tyr Trp Arg Leu Leu Val Gln Gly Thr Tyr Lys Val Thr Ala
    290                 295                 300

Ser Ala Arg Gly Tyr Asp Pro Val Thr Lys Thr Val Glu Val Asp Ser
305                 310                 315                 320

Lys Gly Gly Val Gln Val Asn Phe Thr Leu Ser Arg Thr Asp Ala Lys
                325                 330                 335

Val Glu Glu Gly Lys Val Pro Val Leu Asn Thr Pro Asp Thr Ser Asp
            340                 345                 350

Pro Asn Glu Lys Glu Phe Glu Thr Leu Ile Lys Asp Leu Ser Ala Glu
        355                 360                 365

Asn Gly Leu Glu
    370
```

(2) INFORMATION FOR SEQ ID NO: 65:

(i) SEQUENCE CHARACTERISTICS:
(A) LENGTH: 462 base pairs
(B) TYPE: nucleic acid
(C) STRANDEDNESS: single
(D) TOPOLOGY: linear (ii) MOLECULE TYPE: Genomic DNA (ix) FEATURE:
(A) NAME/KEY: Coding Sequence
(B) LOCATION: 1...462

(xi) SEQUENCE DESCRIPTION: SEQ ID NO: 65:

```
TTT GTC CAG GAC AAG AGT GGC AAG GCA ATT TCT AAA GCT ACC ATT GTC        48
Phe Val Gln Asp Lys Ser Gly Lys Ala Ile Ser Lys Ala Thr Ile Val
  1               5                  10                  15

CTT AAT GAA GGC TTG AGG GTC TAC ACT AAA GAA GGT GGC TAT TTC CAT        96
Leu Asn Glu Gly Leu Arg Val Tyr Thr Lys Glu Gly Gly Tyr Phe His
             20                  25                  30

GTG CTG TTG GCT CCT GGT TTG CAT AAC ATC AAT GCG ATA GCG GAT GGG       144
Val Leu Leu Ala Pro Gly Leu His Asn Ile Asn Ala Ile Ala Asp Gly
         35                  40                  45

TAC CAA CAA AAG CAT ATG AAG GTC TTG GTA CGC CAC GAT GCA CCC AGC       192
Tyr Gln Gln Lys His Met Lys Val Leu Val Arg His Asp Ala Pro Ser
     50                  55                  60

TCT GTG TTC ATG GTA TTT GAC ATG GAA AAC AGG ATA TTT GGT CTG CCT       240
Ser Val Phe Met Val Phe Asp Met Glu Asn Arg Ile Phe Gly Leu Pro
 65                  70                  75                  80

CGA GAG CTG GTT GTA ACT GTT GCA GGT GCA ATT ATG TCT GCT TTG GTC       288
Arg Glu Leu Val Val Thr Val Ala Gly Ala Ile Met Ser Ala Leu Val
                 85                  90                  95

CTC ACT GCC TGT ATC ATC TGG TGT GTC TGC TCA ATC AAG GCC AAC AGA       336
Leu Thr Ala Cys Ile Ile Trp Cys Val Cys Ser Ile Lys Ala Asn Arg
            100                 105                 110

CAC AAA GAT GGC TTC CAC TGC CGG CAG CAC CAC GAC GAT TAC GAG GAC       384
His Lys Asp Gly Phe His Cys Arg Gln His His Asp Asp Tyr Glu Asp
```

-continued

```
        115                 120                 125

GAA ATC CGC ATG ATG TCC ACT GGC TCA AAG AAA TCC CTT TTG AGC CAC      432
Glu Ile Arg Met Met Ser Thr Gly Ser Lys Lys Ser Leu Leu Ser His
    130                 135                 140

GAA TTC CAG GAT GAA ACA GAC ACT GAA GAA                              462
Glu Phe Gln Asp Glu Thr Asp Thr Glu Glu
145                 150
```

(2) INFORMATION FOR SEQ ID NO: 66:

(i) SEQUENCE CHARACTERISTICS:
(A) LENGTH: 154 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 66:

```
Phe Val Gln Asp Lys Ser Gly Lys Ala Ile Ser Lys Ala Thr Ile Val
  1               5                  10                  15

Leu Asn Glu Gly Leu Arg Val Tyr Thr Lys Glu Gly Gly Tyr Phe His
             20                  25                  30

Val Leu Leu Ala Pro Gly Leu His Asn Ile Asn Ala Ile Ala Asp Gly
        35                  40                  45

Tyr Gln Gln Lys His Met Lys Val Leu Val Arg His Asp Ala Pro Ser
     50                  55                  60

Ser Val Phe Met Val Phe Asp Met Glu Asn Arg Ile Phe Gly Leu Pro
 65                  70                  75                  80

Arg Glu Leu Val Val Thr Val Ala Gly Ala Ile Met Ser Ala Leu Val
                 85                  90                  95

Leu Thr Ala Cys Ile Ile Trp Cys Val Cys Ser Ile Lys Ala Asn Arg
             100                 105                 110

His Lys Asp Gly Phe His Cys Arg Gln His His Asp Asp Tyr Glu Asp
        115                 120                 125

Glu Ile Arg Met Met Ser Thr Gly Ser Lys Lys Ser Leu Leu Ser His
    130                 135                 140

Glu Phe Gln Asp Glu Thr Asp Thr Glu Glu
145                 150
```

(2) INFORMATION FOR SEQ ID NO: 67:

(i) SEQUENCE CHARACTERISTICS:
(A) LENGTH: 48 amino acids
(B) TYPE: amino acid
(D) TOPOLOGY: linear (ii) MOLECULE TYPE: peptide (xi) SEQUENCE DESCRIPTION: SEQ ID NO: 67:

```
His Gly Gly Ile Leu Gly Trp Ser Pro Gln Ala Gln Gly Ile Leu Thr
  1               5                  10                  15

Thr Val Ser Thr Ile Pro Pro Pro Ala Ser Thr Asn Arg Trp Ser Gly
             20                  25                  30

Arg Trp Pro Thr Pro Ile Ser Pro Pro Leu Arg Asp Ser His Pro Gln
        35                  40                  45
```

(2) INFORMATION FOR SEQ ID NO: 68:

(i) SEQUENCE CHARACTERISTICS:

-continued (A) LENGTH: 48 amino acids
(B) TYPE: amino acid
(D) TOPOLOGY: linear (ii) MOLECULE TYPE: peptide (xi) SEQUENCE DESCRIPTION: SEQ ID NO: 68:

```
Ala Gly Arg Arg Val Gly Leu Ser Asn Pro Thr Pro Gln Glu Ile Pro
  1               5                  10                  15

Gln Pro Gln Trp Thr Pro Glu Glu Asp Gln Lys Ala Arg Glu Ala Phe
            20                  25                  30

Arg Arg Tyr Gln Glu Glu Arg Pro Pro Glu Thr Thr Thr Ile Pro Pro
        35                  40                  45
```

(2) INFORMATION FOR SEQ ID NO: 69:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO: 69:

```
Lys Ala Arg Glu Ala Phe Arg Arg
  1               5
```

(2) INFORMATION FOR SEQ ID NO: 70:

(i) SEQUENCE CHARACTERISTICS:
(A) LENGTH: 15 amino acids
(B) TYPE: amino acid
(D) TOPOLOGY: linear (ii) MOLECULE TYPE: peptide (xi) SEQUENCE DESCRIPTION: SEQ ID NO: 70:

```
Asp Val Ser Gly Val Leu Phe Gln Tyr Pro Asp Thr Glu Gly Lys
  1               5                  10                  15
```

(2) INFORMATION FOR SEQ ID NO: 71:

(i) SEQUENCE CHARACTERISTICS:
(A) LENGTH: 17 amino acids
(B) TYPE: amino acid
(D) TOPOLOGY: linear (ii) MOLECULE TYPE: peptide (xi) SEQUENCE DESCRIPTION: SEQ ID NO: 71:

```
Glu Val Tyr Arg Leu Ala Leu Gln Thr Arg Glu Gln His Ile Arg Arg
  1               5                  10                  15

Asp
```

(2) INFORMATION FOR SEQ ID NO: 72:

(i) SEQUENCE CHARACTERISTICS:
(A) LENGTH: 14 amino acids
(B) TYPE: amino acid
(D) TOPOLOGY: linear (ii) MOLECULE TYPE: peptide (xi) SEQUENCE DESCRIPTION: SEQ ID NO: 72:

```
Ser Gly Ala Gln Gly Glu Tyr Ala Gly Leu Ala Ala Ile Lys
  1               5                  10
```

-continued (2) INFORMATION FOR SEQ ID NO: 73:

(i) SEQUENCE CHARACTERISTICS:
(A) LENGTH: 8 amino acids
(B) TYPE: amino acid
(D) TOPOLOGY: linear (ii) MOLECULE TYPE: peptide (xi) SEQUENCE DESCRIPTION: SEQ ID NO: 73:

```
Ile Gln Pro Ile Glu Val Asp Lys
  1               5
```

(2) INFORMATION FOR SEQ ID NO: 74:

(i) SEQUENCE CHARACTERISTICS:
(A) LENGTH: 2922 base pairs
(B) TYPE: nucleic acid
(C) STRANDEDNESS: single
(D) TOPOLOGY: linear (ii) MOLECULE TYPE: Genomic DNA (ix) FEATURE:
(A) NAME/KEY: Coding Sequence
(B) LOCATION: 1...2919

(xi) SEQUENCE DESCRIPTION: SEQ ID NO: 74:

```
GAG GCG GCG CGG TGC ATC GAG CAG CTG CTG CCG CGG CAC GAT GAC TTC       48
Glu Ala Ala Arg Cys Ile Glu Gln Leu Leu Pro Arg His Asp Asp Phe
  1               5                  10                  15

TCC CGG CGG CAC ATC GGC CCC CGG GAG GGG GAG AAG AGG GAG ATG CTG       96
Ser Arg Arg His Ile Gly Pro Arg Glu Gly Glu Lys Arg Glu Met Leu
             20                  25                  30

CGA GCC CTC GGG GTG CAG AGC GTC GAG GAG CTG ATG GAT AAA GCC ATC      144
Arg Ala Leu Gly Val Gln Ser Val Glu Glu Leu Met Asp Lys Ala Ile
         35                  40                  45

CCG GGC AGC ATC CGG CTG CGC AGG CCG CTG AGG ATG GAG GAC CCC GTG      192
Pro Gly Ser Ile Arg Leu Arg Arg Pro Leu Arg Met Glu Asp Pro Val
     50                  55                  60

GGT GAA AAT GAA ATC CTT GAA ACT TTA TAC AAT ATT GCA AGC AAG AAC      240
Gly Glu Asn Glu Ile Leu Glu Thr Leu Tyr Asn Ile Ala Ser Lys Asn
 65                  70                  75                  80

AAG ATA TGG AGG TCC TAT ATA GGC ATG GGT TAT TAC AAC TGC TCA GTG      288
Lys Ile Trp Arg Ser Tyr Ile Gly Met Gly Tyr Tyr Asn Cys Ser Val
                 85                  90                  95

CCT CAA CCC ATT GCA CGG AAT TTG TTG GAG AAT GCA GGA TGG GTT ACC      336
Pro Gln Pro Ile Ala Arg Asn Leu Leu Glu Asn Ala Gly Trp Val Thr
            100                 105                 110

CAG TAT ACT CCC TAC CAA CCT GAG GTC TCA CAG GGC AGG CTG GAG AGC      384
Gln Tyr Thr Pro Tyr Gln Pro Glu Val Ser Gln Gly Arg Leu Glu Ser
        115                 120                 125

CTG CTA AAT TAC CAG ACT ATG GTG TGT GAT ATC ACA GGA ATG GAT GTG      432
Leu Leu Asn Tyr Gln Thr Met Val Cys Asp Ile Thr Gly Met Asp Val
    130                 135                 140

GCT AAT GCA TCA TTG CTG GAT GAG GGG ACA GCT GCT GCA GAA GCT ATG      480
Ala Asn Ala Ser Leu Leu Asp Glu Gly Thr Ala Ala Ala Glu Ala Met
145                 150                 155                 160

CAA TTA TGT CAC AGG CAC AAC AAA AGG AGG AAG TTT TAT GTA GAT TCC      528
Gln Leu Cys His Arg His Asn Lys Arg Arg Lys Phe Tyr Val Asp Ser
                165                 170                 175

CGA TGC CAC CCT CAG ACT ATA GCA GTG GTC CAA ACT AGA GCC AAT TAT      576
Arg Cys His Pro Gln Thr Ile Ala Val Val Gln Thr Arg Ala Asn Tyr
            180                 185                 190
```

-continued

```
ACA GGT GTT ATT ACT GAG CTC AAA TTA CCC CAT GAG ATG GAT TTC AGT      624
Thr Gly Val Ile Thr Glu Leu Lys Leu Pro His Glu Met Asp Phe Ser
        195                 200                 205

GGA AAG GAT GTC AGT GGA GTA TTA TTT CAG TAT CCA GAC ACT GAG GGG      672
Gly Lys Asp Val Ser Gly Val Leu Phe Gln Tyr Pro Asp Thr Glu Gly
    210                 215                 220

AAG GTG GAA GAC TTC TCT GAA CTT GTT GAA AGA GCT CAT CAG AAC GGG      720
Lys Val Glu Asp Phe Ser Glu Leu Val Glu Arg Ala His Gln Asn Gly
225                 230                 235                 240

ACT CTT GCC TGC TGT GCT ACT GAT CTT CTG GCT CTC TGT ATT CTG AAG      768
Thr Leu Ala Cys Cys Ala Thr Asp Leu Leu Ala Leu Cys Ile Leu Lys
                245                 250                 255

CCT CCT GGA GAG TTT GGG GTA GAT GTT GTC CTG GGT AGC TCC CAG AGA      816
Pro Pro Gly Glu Phe Gly Val Asp Val Val Leu Gly Ser Ser Gln Arg
            260                 265                 270

TTT GGT GTG CCA CTC TGC TAT GGG GGA CCC CAC GCA GCA TTC TTC GCT      864
Phe Gly Val Pro Leu Cys Tyr Gly Gly Pro His Ala Ala Phe Phe Ala
        275                 280                 285

GTC AAG GAA AAC CTA GTG AGA ATG ATG CCA GGC AGG ATG GTG GGT GTC      912
Val Lys Glu Asn Leu Val Arg Met Met Pro Gly Arg Met Val Gly Val
    290                 295                 300

ACA AGA GAT GCA AAT GGA AAA GAA GTT TAC CGA CTG GCT TTA CAA ACA      960
Thr Arg Asp Ala Asn Gly Lys Glu Val Tyr Arg Leu Ala Leu Gln Thr
305                 310                 315                 320

CGA GAG CAG CAT ATC AGG AGG GAC AAA GCT ACA AGC AAC ATC TGC ACA     1008
Arg Glu Gln His Ile Arg Arg Asp Lys Ala Thr Ser Asn Ile Cys Thr
                325                 330                 335

GCA CAG GCT CTT CTG GCT AAT ATG GCA GCC ATG TTT GGT GTC TAC CAT     1056
Ala Gln Ala Leu Leu Ala Asn Met Ala Ala Met Phe Gly Val Tyr His
            340                 345                 350

GGG TCT GAT GGA TTA AGG GAT ATT GCA AGA CGG GTA CAC AAT GCT ACT     1104
Gly Ser Asp Gly Leu Arg Asp Ile Ala Arg Arg Val His Asn Ala Thr
        355                 360                 365

TTA ATC CTG GCT GAA GGT CTC AGG AGA GCT GGT CAT AAA CTG CAC CAT     1152
Leu Ile Leu Ala Glu Gly Leu Arg Arg Ala Gly His Lys Leu His His
    370                 375                 380

GAT CTG TTC TTT GAT ACC TTG ACA GTC ACG TGT GGA TGC TCA GTC AAA     1200
Asp Leu Phe Phe Asp Thr Leu Thr Val Thr Cys Gly Cys Ser Val Lys
385                 390                 395                 400

GAA GTT TTG GAC AGG GCA GCT CTT AGA AAG ATA AAT TTT CGC ATT TAT     1248
Glu Val Leu Asp Arg Ala Ala Leu Arg Lys Ile Asn Phe Arg Ile Tyr
                405                 410                 415

AGT GAT GGC AGA CTT GGA GTA TCA CTT GAT GAA ACT GTA AGT GAG AAA     1296
Ser Asp Gly Arg Leu Gly Val Ser Leu Asp Glu Thr Val Ser Glu Lys
            420                 425                 430

GAC CTA GAT GAC ATA TTA TGG ATT TTT GGT TGC GAG TCT TCA GCT GAA     1344
Asp Leu Asp Asp Ile Leu Trp Ile Phe Gly Cys Glu Ser Ser Ala Glu
        435                 440                 445

CTA ATT GCT GAA GGT ATG GGC GAG GAA ACC AAA GGT ATC CTT AGC ACC     1392
Leu Ile Ala Glu Gly Met Gly Glu Glu Thr Lys Gly Ile Leu Ser Thr
    450                 455                 460

CCA TTT AAG AGA ACT TCC AAA TTC TTG ACC CAT CAG GTT TTC AAC AGC     1440
Pro Phe Lys Arg Thr Ser Lys Phe Leu Thr His Gln Val Phe Asn Ser
465                 470                 475                 480

TAT CAC TCC GAA ACA AAT ATC GTA CGG TAC ATG AAG AGA TTA GAA AAC     1488
Tyr His Ser Glu Thr Asn Ile Val Arg Tyr Met Lys Arg Leu Glu Asn
                485                 490                 495

AAA GAT ATT TCC CTT GTT CAC AGC ATG ATT CCT TTG GGG TCC TGT ACA     1536
Lys Asp Ile Ser Leu Val His Ser Met Ile Pro Leu Gly Ser Cys Thr
```

-continued

```
            500                 505                 510

ATG AAG CTC AAT AGT TCA GCT GAA CTT GCA CCT ATT TCA TGG AAG GAA      1584
Met Lys Leu Asn Ser Ser Ala Glu Leu Ala Pro Ile Ser Trp Lys Glu
        515                 520                 525

TTT GCC AAC ATC CAC CCC TTT GTG CCC TTG GAT CAA GCT CAA GGG TAT      1632
Phe Ala Asn Ile His Pro Phe Val Pro Leu Asp Gln Ala Gln Gly Tyr
    530                 535                 540

CAG CAG CTT TTC AAG GAC TTA GAG AAG GAC CTG TGT GAG ATT ACT GGT      1680
Gln Gln Leu Phe Lys Asp Leu Glu Lys Asp Leu Cys Glu Ile Thr Gly
545                 550                 555                 560

TAC GAC AAA ATC TCC TTC CAA CCA AAC AGT GGA GCC CAA GGA GAG TAC      1728
Tyr Asp Lys Ile Ser Phe Gln Pro Asn Ser Gly Ala Gln Gly Glu Tyr
                565                 570                 575

GCA GGC TTG GCC GCA ATC AAA GCT TAT TTA AAT GCA AAA GGA GAA CGT      1776
Ala Gly Leu Ala Ala Ile Lys Ala Tyr Leu Asn Ala Lys Gly Glu Arg
            580                 585                 590

CAT CGA AGT GTT TGC CTT ATT CCT AGA TCT GCT CAT GGT ACA AAT CCA      1824
His Arg Ser Val Cys Leu Ile Pro Arg Ser Ala His Gly Thr Asn Pro
        595                 600                 605

GCA AGT GCA CAG ATG GCA GGG ATG AAG ATT CAA CCA GTT GAA GTA GAT      1872
Ala Ser Ala Gln Met Ala Gly Met Lys Ile Gln Pro Val Glu Val Asp
    610                 615                 620

AAA AAT GGG AGC ATT GAT ATC TCC CAT TTA AAA GCA ATG GTG GAC AAA      1920
Lys Asn Gly Ser Ile Asp Ile Ser His Leu Lys Ala Met Val Asp Lys
625                 630                 635                 640

CAC AAG GAG AAC CTG GCA GCC ATC ATG ATC ACA TAC CCT TCC ACC AAT      1968
His Lys Glu Asn Leu Ala Ala Ile Met Ile Thr Tyr Pro Ser Thr Asn
                645                 650                 655

GGT GTG TTT GAG GAG GAG ATT GGG GAT GTG TGT GAG CTG ATT CAC AAA      2016
Gly Val Phe Glu Glu Glu Ile Gly Asp Val Cys Glu Leu Ile His Lys
            660                 665                 670

AAC GGA GGC CAG GTT TAC CTG GAT GGA GCA AAC ATG AAC GCC CAA GTG      2064
Asn Gly Gly Gln Val Tyr Leu Asp Gly Ala Asn Met Asn Ala Gln Val
        675                 680                 685

GGT CTG TGT CGT CCT GGA GAT TAT GGC TCT GAT GTC TCT CAC TTA AAC      2112
Gly Leu Cys Arg Pro Gly Asp Tyr Gly Ser Asp Val Ser His Leu Asn
    690                 695                 700

CTT CAC AAA ACC TTT TGC ATT CCC CAT GGA GGA GGA GGA CCT GGA ATG      2160
Leu His Lys Thr Phe Cys Ile Pro His Gly Gly Gly Gly Pro Gly Met
705                 710                 715                 720

GGA CCA ATT GGA GTG AAG AAA CAT CTG GCT CCC TAC TTG CCT ACC CAT      2208
Gly Pro Ile Gly Val Lys Lys His Leu Ala Pro Tyr Leu Pro Thr His
                725                 730                 735

CCT GTC ATC AAG ATT CAG ACG GAT AAG GAT GCA TGT CCT TTG GGT ACT      2256
Pro Val Ile Lys Ile Gln Thr Asp Lys Asp Ala Cys Pro Leu Gly Thr
            740                 745                 750

GTC AGT GCT GCA CCT TGG GGT TCC AGT GCT ATA TTG CCT ATT TCC TGG      2304
Val Ser Ala Ala Pro Trp Gly Ser Ser Ala Ile Leu Pro Ile Ser Trp
        755                 760                 765

GTG TAT ATC AAG ACA ATG GGA GCA AAG GGT CTT AAA CAC GCT TCT GAG      2352
Val Tyr Ile Lys Thr Met Gly Ala Lys Gly Leu Lys His Ala Ser Glu
    770                 775                 780

GTT GCT ATA TTA AAT GCA AAC TAC ATG GCA AAG AGG CTG GAG AAG CAC      2400
Val Ala Ile Leu Asn Ala Asn Tyr Met Ala Lys Arg Leu Glu Lys His
785                 790                 795                 800

TAC AAA ATC CTT TTC AGA GGA GTA AGA GGT TAT GTA GCC CAT GAA TTC      2448
Tyr Lys Ile Leu Phe Arg Gly Val Arg Gly Tyr Val Ala His Glu Phe
                805                 810                 815

ATT TTG GAT ACA AGA CCT TTC AAA AAA ACA GCA AAC ATT GAA GCT GTG      2496
```

-continued

```
Ile Leu Asp Thr Arg Pro Phe Lys Lys Thr Ala Asn Ile Glu Ala Val
            820                 825                 830

GAT CTT GCT AAG CGA CTT CAG GAT TAT GGT TTT CAT GCT CCA ACC ATG     2544
Asp Leu Ala Lys Arg Leu Gln Asp Tyr Gly Phe His Ala Pro Thr Met
        835                 840                 845

TCC TGG CCA GTG GCA GGC ACA CTT ATG ATT GAA CCA ACA GAG TCT GAA     2592
Ser Trp Pro Val Ala Gly Thr Leu Met Ile Glu Pro Thr Glu Ser Glu
    850                 855                 860

GAC AAG GCA GAG CTG GAC AGG TTT TGT GAT GCA ATG ATC AGT ATT CGA     2640
Asp Lys Ala Glu Leu Asp Arg Phe Cys Asp Ala Met Ile Ser Ile Arg
865                 870                 875                 880

CAG GAA ATT GCT GAA ATA GAG GAG GGC AGG ATG GAC CCT CAG ATT AAC     2688
Gln Glu Ile Ala Glu Ile Glu Glu Gly Arg Met Asp Pro Gln Ile Asn
                885                 890                 895

CCA TTA AAG ATG TCA CCA CAT ACT CTA AAC TGT GTC ACT TCT TCA AAG     2736
Pro Leu Lys Met Ser Pro His Thr Leu Asn Cys Val Thr Ser Ser Lys
            900                 905                 910

TGG GAT CGT CCT TAT TCC AGA GAA GTG GCA GCA TTC CCA CTG CCG TTT     2784
Trp Asp Arg Pro Tyr Ser Arg Glu Val Ala Ala Phe Pro Leu Pro Phe
        915                 920                 925

GTG AAA CCT GAG AGC AAG TTT TGG CCC ACA ATT GCT CGC ATC GAT GAC     2832
Val Lys Pro Glu Ser Lys Phe Trp Pro Thr Ile Ala Arg Ile Asp Asp
    930                 935                 940

ATA TAC GGA GAT CAA CAC CTG GTT TGT ACC TGC CCA CCG ATG GAA GCC     2880
Ile Tyr Gly Asp Gln His Leu Val Cys Thr Cys Pro Pro Met Glu Ala
945                 950                 955                 960

TAC GAA TCT CCC TTC TCT GAA CAG AAG AGA GCA TCT TCG TAA             2922
Tyr Glu Ser Pro Phe Ser Glu Gln Lys Arg Ala Ser Ser
                965                 970
```

(2) INFORMATION FOR SEQ ID NO: 75:

(i) SEQUENCE CHARACTERISTICS:
(A) LENGTH: 973 amino acids
(B) TYPE: amino acid
(D) TOPOLOGY: linear (ii) MOLECULE TYPE: protein (v) FRAGMENT TYPE: internal (xi) SEQUENCE DESCRIPTION: SEQ ID NO: 75:

```
Glu Ala Ala Arg Cys Ile Glu Gln Leu Leu Pro Arg His Asp Asp Phe
  1               5                  10                  15

Ser Arg Arg His Ile Gly Pro Arg Glu Gly Glu Lys Arg Glu Met Leu
            20                  25                  30

Arg Ala Leu Gly Val Gln Ser Val Glu Glu Leu Met Asp Lys Ala Ile
        35                  40                  45

Pro Gly Ser Ile Arg Leu Arg Arg Pro Leu Arg Met Glu Asp Pro Val
    50                  55                  60

Gly Glu Asn Glu Ile Leu Glu Thr Leu Tyr Asn Ile Ala Ser Lys Asn
 65                  70                  75                  80

Lys Ile Trp Arg Ser Tyr Ile Gly Met Gly Tyr Tyr Asn Cys Ser Val
                85                  90                  95

Pro Gln Pro Ile Ala Arg Asn Leu Leu Glu Asn Ala Gly Trp Val Thr
            100                 105                 110

Gln Tyr Thr Pro Tyr Gln Pro Glu Val Ser Gln Gly Arg Leu Glu Ser
        115                 120                 125

Leu Leu Asn Tyr Gln Thr Met Val Cys Asp Ile Thr Gly Met Asp Val
    130                 135                 140
```

-continued

```
Ala Asn Ala Ser Leu Leu Asp Glu Gly Thr Ala Ala Ala Glu Ala Met
145                 150                 155                 160

Gln Leu Cys His Arg His Asn Lys Arg Arg Lys Phe Tyr Val Asp Ser
                165                 170                 175

Arg Cys His Pro Gln Thr Ile Ala Val Val Gln Thr Arg Ala Asn Tyr
            180                 185                 190

Thr Gly Val Ile Thr Glu Leu Lys Leu Pro His Glu Met Asp Phe Ser
        195                 200                 205

Gly Lys Asp Val Ser Gly Val Leu Phe Gln Tyr Pro Asp Thr Glu Gly
    210                 215                 220

Lys Val Glu Asp Phe Ser Glu Leu Val Glu Arg Ala His Gln Asn Gly
225                 230                 235                 240

Thr Leu Ala Cys Cys Ala Thr Asp Leu Leu Ala Leu Cys Ile Leu Lys
                245                 250                 255

Pro Pro Gly Glu Phe Gly Val Asp Val Val Leu Gly Ser Ser Gln Arg
            260                 265                 270

Phe Gly Val Pro Leu Cys Tyr Gly Gly Pro His Ala Ala Phe Phe Ala
        275                 280                 285

Val Lys Glu Asn Leu Val Arg Met Met Pro Gly Arg Met Val Gly Val
    290                 295                 300

Thr Arg Asp Ala Asn Gly Lys Glu Val Tyr Arg Leu Ala Leu Gln Thr
305                 310                 315                 320

Arg Glu Gln His Ile Arg Arg Asp Lys Ala Thr Ser Asn Ile Cys Thr
                325                 330                 335

Ala Gln Ala Leu Leu Ala Asn Met Ala Ala Met Phe Gly Val Tyr His
            340                 345                 350

Gly Ser Asp Gly Leu Arg Asp Ile Ala Arg Arg Val His Asn Ala Thr
        355                 360                 365

Leu Ile Leu Ala Glu Gly Leu Arg Arg Ala Gly His Lys Leu His His
    370                 375                 380

Asp Leu Phe Phe Asp Thr Leu Thr Val Thr Cys Gly Cys Ser Val Lys
385                 390                 395                 400

Glu Val Leu Asp Arg Ala Ala Leu Arg Lys Ile Asn Phe Arg Ile Tyr
                405                 410                 415

Ser Asp Gly Arg Leu Gly Val Ser Leu Asp Glu Thr Val Ser Glu Lys
            420                 425                 430

Asp Leu Asp Asp Ile Leu Trp Ile Phe Gly Cys Glu Ser Ser Ala Glu
        435                 440                 445

Leu Ile Ala Glu Gly Met Gly Glu Glu Thr Lys Gly Ile Leu Ser Thr
    450                 455                 460

Pro Phe Lys Arg Thr Ser Lys Phe Leu Thr His Gln Val Phe Asn Ser
465                 470                 475                 480

Tyr His Ser Glu Thr Asn Ile Val Arg Tyr Met Lys Arg Leu Glu Asn
                485                 490                 495

Lys Asp Ile Ser Leu Val His Ser Met Ile Pro Leu Gly Ser Cys Thr
            500                 505                 510

Met Lys Leu Asn Ser Ser Ala Glu Leu Ala Pro Ile Ser Trp Lys Glu
        515                 520                 525

Phe Ala Asn Ile His Pro Phe Val Pro Leu Asp Gln Ala Gln Gly Tyr
    530                 535                 540

Gln Gln Leu Phe Lys Asp Leu Glu Lys Asp Leu Cys Glu Ile Thr Gly
545                 550                 555                 560
```

-continued

```
Tyr Asp Lys Ile Ser Phe Gln Pro Asn Ser Gly Ala Gln Gly Glu Tyr
                565                 570                 575

Ala Gly Leu Ala Ala Ile Lys Ala Tyr Leu Asn Ala Lys Gly Glu Arg
            580                 585                 590

His Arg Ser Val Cys Leu Ile Pro Arg Ser Ala His Gly Thr Asn Pro
        595                 600                 605

Ala Ser Ala Gln Met Ala Gly Met Lys Ile Gln Pro Val Glu Val Asp
    610                 615                 620

Lys Asn Gly Ser Ile Asp Ile Ser His Leu Lys Ala Met Val Asp Lys
625                 630                 635                 640

His Lys Glu Asn Leu Ala Ala Ile Met Ile Thr Tyr Pro Ser Thr Asn
                645                 650                 655

Gly Val Phe Glu Glu Glu Ile Gly Asp Val Cys Glu Leu Ile His Lys
            660                 665                 670

Asn Gly Gly Gln Val Tyr Leu Asp Gly Ala Asn Met Asn Ala Gln Val
        675                 680                 685

Gly Leu Cys Arg Pro Gly Asp Tyr Gly Ser Asp Val Ser His Leu Asn
    690                 695                 700

Leu His Lys Thr Phe Cys Ile Pro His Gly Gly Gly Gly Pro Gly Met
705                 710                 715                 720

Gly Pro Ile Gly Val Lys Lys His Leu Ala Pro Tyr Leu Pro Thr His
                725                 730                 735

Pro Val Ile Lys Ile Gln Thr Asp Lys Asp Ala Cys Pro Leu Gly Thr
            740                 745                 750

Val Ser Ala Ala Pro Trp Gly Ser Ser Ala Ile Leu Pro Ile Ser Trp
        755                 760                 765

Val Tyr Ile Lys Thr Met Gly Ala Lys Gly Leu Lys His Ala Ser Glu
    770                 775                 780

Val Ala Ile Leu Asn Ala Asn Tyr Met Ala Lys Arg Leu Glu Lys His
785                 790                 795                 800

Tyr Lys Ile Leu Phe Arg Gly Val Arg Gly Tyr Val Ala His Glu Phe
                805                 810                 815

Ile Leu Asp Thr Arg Pro Phe Lys Lys Thr Ala Asn Ile Glu Ala Val
            820                 825                 830

Asp Leu Ala Lys Arg Leu Gln Asp Tyr Gly Phe His Ala Pro Thr Met
        835                 840                 845

Ser Trp Pro Val Ala Gly Thr Leu Met Ile Glu Pro Thr Glu Ser Glu
    850                 855                 860

Asp Lys Ala Glu Leu Asp Arg Phe Cys Asp Ala Met Ile Ser Ile Arg
865                 870                 875                 880

Gln Glu Ile Ala Glu Ile Glu Glu Gly Arg Met Asp Pro Gln Ile Asn
                885                 890                 895

Pro Leu Lys Met Ser Pro His Thr Leu Asn Cys Val Thr Ser Ser Lys
            900                 905                 910

Trp Asp Arg Pro Tyr Ser Arg Glu Val Ala Ala Phe Pro Leu Pro Phe
        915                 920                 925

Val Lys Pro Glu Ser Lys Phe Trp Pro Thr Ile Ala Arg Ile Asp Asp
    930                 935                 940

Ile Tyr Gly Asp Gln His Leu Val Cys Thr Cys Pro Pro Met Glu Ala
945                 950                 955                 960

Tyr Glu Ser Pro Phe Ser Glu Gln Lys Arg Ala Ser Ser
                965                 970
```

-continued (2) INFORMATION FOR SEQ ID NO: 76:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 76:

```
Met Gln Trp Asn Ser Thr Ala Phe His Gln Thr Leu Gln Asp Pro Arg
  1               5                  10                  15

Val Arg Gly Leu Tyr Leu Pro Ala Gly Gly Ser Ser Ser Gly Thr Val
             20                  25                  30

Asn Pro Ala Pro Asn Ile Ala Ser His Ile Ser Ser Ile Ser Ala Arg
         35                  40                  45

Thr Gly Asp Pro Val Thr Asn
     50                  55
```

(2) INFORMATION FOR SEQ ID NO: 77:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 77:

```
Met Gln Trp Asn Ser Thr Ala Leu His Gln Ala Leu Gln Asp Pro Arg
  1               5                  10                  15

Val Arg Gly Leu Tyr Phe Pro Ala Gly Gly Ser Ser Ser Gly Thr Val
             20                  25                  30

Asn Pro Ala Pro Asn Ile Ala Ser His Ile Ser Ser Ile Ser Ala Arg
         35                  40                  45

Thr Gly Asp Pro Val Thr Asn
     50                  55
```

(2) INFORMATION FOR SEQ ID NO: 78:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 78:

```
Met Gln Trp Asn Ser Thr Ala Leu His Gln Ala Leu Gln Asp Pro Arg
  1               5                  10                  15

Val Arg Gly Leu Tyr Phe Pro Ala Gly Gly Ser Ser Ser Gly Thr Leu
             20                  25                  30

Asn Pro Val Gln Thr Ile Ala Ser His Ile Ser Ser Ile Ser Ser Arg
         35                  40                  45

Ile Gly Asp Pro Ala Pro Asn
     50                  55
```

(2) INFORMATION FOR SEQ ID NO: 79:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 79:

```
Met Gln Trp Asn Ser Thr Thr Leu His Gln Thr Leu Gln Asp Pro Arg
  1               5                  10                  15

Val Arg Ala Leu Tyr Phe Pro Ala Gly Gly Ser Ser Ser Gly Thr Val
```

-continued

```
            20                  25                  30

Asn Pro Val Gln Asn Thr Val Ser Ser Ile Ser Ser Ile Leu Ser Lys
        35                  40                  45

Thr Gly Asp Pro Val Pro Asn
    50                  55
```

(2) INFORMATION FOR SEQ ID NO: 80:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 80:

```
Met Gln Trp Asn Ser Thr Thr Leu His Gln Thr Leu Gln Asp Pro Arg
  1               5                  10                  15

Val Arg Ala Leu Tyr Phe Pro Ala Gly Gly Ser Ser Ser Gly Thr Val
            20                  25                  30

Asn Pro Val Gln Asn Thr Ala Ser Ser Ile Ser Ser Ile Leu Ser Thr
        35                  40                  45

Thr Gly Asp Pro Val Pro Asn
    50                  55
```

(2) INFORMATION FOR SEQ ID NO: 81:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 81:

```
Met Gln Trp Asn Ser Thr Thr Leu His Gln Thr Leu Gln Asp Pro Gly
  1               5                  10                  15

Val Arg Ala Leu Tyr Phe Pro Ala Gly Gly Ser Ser Ser Gly Thr Val
            20                  25                  30

Ser Pro Ala Gln Asn Thr Val Ser Ala Ile Ser Ser Ile Leu Ser Lys
        35                  40                  45

Thr Gly Asp Pro Val Pro Asn
    50                  55
```

(2) INFORMATION FOR SEQ ID NO: 82:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 82:

```
Met Gln Trp Asn Ser Thr Thr Leu His Gln Thr Leu Gln Asp Pro Arg
  1               5                  10                  15

Val Arg Ala Leu Tyr Phe Pro Ala Gly Gly Ser Ser Ser Gly Thr Val
            20                  25                  30

Ser Pro Ala Pro Asn Thr Val Ser Ala Ile Ser Ser Ile Leu Ser Lys
        35                  40                  45

Thr Gly Asp Pro Val Pro Asn
    50                  55
```

(2) INFORMATION FOR SEQ ID NO: 83:

(i) SEQUENCE CHARACTERISTICS:
(A) LENGTH: 55 amino acids

-continued (B) TYPE: amino acid
(D) TOPOLOGY: linear (xi) SEQUENCE DESCRIPTION: SEQ ID NO: 83:

```
Met Gln Trp Asn Ser Thr Thr Leu His Gln Ala Leu Leu Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Ala Ser Pro Ile Ser Ser Thr Phe Ser Arg
         35                  40                  45

Thr Gly Asp Pro Ala Pro Asn
     50                  55
```

(2) INFORMATION FOR SEQ ID NO: 84:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 84:

```
Met Gln Trp Asn Ser Thr Thr Leu His Gln Ala Leu Leu Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Ala Ser Pro Ile Ser Ser Ile Phe Ser Arg
         35                  40                  45

Thr Gly Asp Pro Ala Pro Asn
     50                  55
```

(2) INFORMATION FOR SEQ ID NO: 85:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 85:

```
Met Gln Trp Asn Ser Thr Thr Leu His Gln Ala Leu Leu Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Val Ser Pro Ile Ser Ser Ile Phe Ser Arg
         35                  40                  45

Thr Gly Asp Pro Ala Pro Asn
     50                  55
```

(2) INFORMATION FOR SEQ ID NO: 86:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 86:

```
Met Gln Trp Asn Ser Thr Thr Leu His Gln Ala Leu Leu Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Ala Ser Pro Ile Ser Ser Ile Ser Ser Arg
         35                  40                  45
```

-continued

```
Thr Gly Asp Pro Ala Pro Asn
     50                  55
```

(2) INFORMATION FOR SEQ ID NO: 87:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 87:

```
Met Gln Trp Asn Ser Thr Thr Leu His Gln Ala Leu Leu Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Ala Ser Pro Ile Ser Ser Ile Phe Ser Arg
         35                  40                  45

Thr Gly Asp Pro Ala Pro Asn
     50                  55
```

(2) INFORMATION FOR SEQ ID NO: 88:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 88:

```
Met Gln Trp Asn Ser Thr Thr Leu His Gln Val Leu Leu Asp Pro Arg
  1               5                  10                  15

Val Arg Gly Leu Tyr Phe Pro Pro Gly Gly Ser Ser Ser Gly Thr Val
             20                  25                  30

Asn Pro Val Pro Thr Thr Ala Ser Pro Ile Ser Ser Ile Ser Ser Arg
         35                  40                  45

Thr Gly Asp Pro Ala Pro Asn
     50                  55
```

(2) INFORMATION FOR SEQ ID NO: 89:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 89:

```
Met Gln Trp Asn Ser Thr Thr Leu His Gln Ala Leu Leu Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Ala Ser Pro Ile Ser Ser Ile Phe Ser Arg
         35                  40                  45

Thr Gly Asp Pro Ala Pro Asn
     50                  55
```

(2) INFORMATION FOR SEQ ID NO: 90:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 90:

-continued

Met Gln Trp Asn Ser Thr Thr Leu His Gln Ala Leu Leu Asp Pro Arg
1 5 10 15

Val Arg Gly Leu Tyr Phe Pro Ala Gly Gly Ser Ser Ser Gly Thr Val
20 25 30

Asn Pro Val Pro Thr Thr Ala Ser Pro Ile Ser Ser Ile Phe Ser Arg
35 40 45

Thr Gly Asp Pro Ala Pro Asn
50 55

(2) INFORMATION FOR SEQ ID NO: 91:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 91:

Met Gln Trp Asn Ser Thr Thr Leu Gln Gln Ala Leu Gln Asp Pro Arg
1 5 10 15

Val Arg Val Leu Tyr Phe Pro Ala Gly Gly Ser Ser Ser Gly Thr Val
20 25 30

Asn Pro Val Pro Thr Thr Ala Ser Leu Ile Ser Ser Ile Phe Ser Arg
35 40 45

Ile Gly Asp Pro Val Thr Asn
50 55

(2) INFORMATION FOR SEQ ID NO: 92:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 92:

Met Gln Trp Asn Ser Thr Thr Leu Gln Gln Ala Leu Leu Asp Pro Arg
1 5 10 15

Val Arg Gly Leu Tyr Phe Pro Ala Gly Gly Ser Ser Ser Gly Thr Val
20 25 30

Asn Pro Val Pro Thr Thr Ala Ser Leu Ile Ser Ser Ile Phe Ser Arg
35 40 45

Thr Gly Asp Pro Val Thr Asn
50 55

(2) INFORMATION FOR SEQ ID NO: 93:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 93:

Met Gln Trp Asn Ser Thr Thr Leu His Gln Thr Leu Gln Asp Pro Arg
1 5 10 15

Val Arg Gly Leu Tyr Phe Pro Ala Gly Gly Ser Ser Ser Gly Thr Val
20 25 30

Asn Pro Val Pro Thr Thr Val Ser Pro Ile Ser Ser Ile Phe Ser Arg
35 40 45

Ile Gly Asp Pro Ala Leu Asn
50 55

-continued (2) INFORMATION FOR SEQ ID NO: 94:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 94:

```
Met Gln Trp Asn Ser Thr Thr Leu His Gln Thr Leu Gln Asp Pro Arg
  1               5                  10                  15

Val Arg Gly Leu Tyr Pro Pro Ala Gly Gly Ser Ser Ser Gly Thr Val
             20                  25                  30

Asn Pro Val Pro Thr Thr Val Ser His Ile Ser Ser Ile Phe Thr Arg
         35                  40                  45

Ile Gly Asp Pro Ala Leu Asn
     50                  55
```

(2) INFORMATION FOR SEQ ID NO: 95:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 95:

```
Met Gln Trp Asn Ser Thr Thr Leu His Gln Thr Leu Gln Asp Pro Arg
  1               5                  10                  15

Val Arg Gly Leu Tyr Leu Pro Ala Gly Gly Ser Ser Ser Gly Thr Val
             20                  25                  30

Asn Pro Val Pro Thr Thr Val Ser Pro Ile Ser Ser Ile Phe Ser Arg
         35                  40                  45

Ile Gly Asp Pro Ala Leu Asn
     50                  55
```

(2) INFORMATION FOR SEQ ID NO: 96:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 96:

```
Met Gln Trp Asn Ser Thr Thr Leu His Gln Thr Leu Gln Asp Pro Arg
  1               5                  10                  15

Val Arg Gly Leu Tyr Phe Pro Ala Gly Gly Ser Ser Ser Gly Thr Val
             20                  25                  30

Asn Pro Val Pro Thr Thr Ala Ser Pro Ile Ser Ser Ile Phe Ser Arg
         35                  40                  45

Ile Gly Asp Pro Ala Leu Asn
     50                  55
```

(2) INFORMATION FOR SEQ ID NO: 97:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 97:

```
Met Gln Trp Asn Ser Thr Thr Leu His Gln Thr Leu Gln Asp Pro Arg
  1               5                  10                  15
```

-continued

```
Val Arg Gly Leu Tyr Phe Pro Ala Gly Gly Ser Ser Ser Gly Thr Val
            20                  25                  30

Asn Pro Val Pro Thr Thr Ala Ser Pro Leu Ser Ser Ile Phe Ser Arg
        35                  40                  45

Ile Gly Asp Pro Ala Leu Asn
    50                  55
```

(2) INFORMATION FOR SEQ ID NO: 98:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 98:

```
Met Gln Trp Ile Ser Thr Thr Leu His Gln Ala Leu Gln Asp Pro Arg
  1               5                  10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Leu Ser Ile Phe Ser Lys
        35                  40                  45

Ile Gly Asp Leu Ala Pro Asn
    50                  55
```

(2) INFORMATION FOR SEQ ID NO: 99:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 99:

```
Met Gln Trp Asn Ser Thr Thr Leu His Gln Ala Leu Gln Asp Pro Arg
  1               5                  10                  15

Val Arg Gly Leu Tyr Phe Pro Ala Gly Gly Ser Ser Ser Gly Thr Val
            20                  25                  30

Asn Pro Val Pro Thr Thr Ala Ser Leu Ile Ser Ser Ile Phe Ser Arg
        35                  40                  45

Ile Gly Asp Pro Ala Pro Asn
    50                  55
```

(2) INFORMATION FOR SEQ ID NO: 100:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 100:

```
Met Gln Trp Asn Ser Thr Thr Leu His Gln Ala Leu Gln Asp Pro Arg
  1               5                  10                  15

Val Arg Gly Leu Tyr Phe Pro Ala Gly Gly Ser Ser Ser Gly Thr Val
            20                  25                  30

Asn Pro Val Pro Thr Thr Ala Ser Leu Ile Ser Ser Ile Phe Ser Arg
        35                  40                  45

Ile Gly Asp Pro Ala Pro Asn
    50                  55
```

(2) INFORMATION FOR SEQ ID NO: 101:

(i) SEQUENCE CHARACTERISTICS:

-continued (A) LENGTH: 55 amino acids
(B) TYPE: amino acid
(D) TOPOLOGY: linear (xi) SEQUENCE DESCRIPTION: SEQ ID NO: 101:

```
Met Gln Trp Asn Ser Thr His Leu His Gln Ala Leu Leu Asp Pro Arg
  1               5                  10                  15

Val Arg Ala Leu Tyr Phe Pro Ala Gly Gly Ser Ser Ser Gly Thr Gln
             20                  25                  30

Asn Pro Ala Pro Thr Ile Ala Ser Leu Thr Ser Ser Ile Ser Ser Lys
         35                  40                  45

Thr Gly Gly Pro Ala Met Asn
     50                  55
```

(2) INFORMATION FOR SEQ ID NO: 102:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 102:

```
Met Gln Trp Asn Ser Thr His Leu His Gln Ala Leu Leu Asp Pro Arg
  1               5                  10                  15

Val Arg Ala Leu Tyr Phe Pro Ala Gly Gly Ser Ser Ser Gly Thr Gln
             20                  25                  30

Asn Pro Ala Pro Thr Ile Ala Ser Leu Thr Ser Ser Ile Ser Ser Lys
         35                  40                  45

Thr Gly Gly Pro Ala Met Asn
     50                  55
```

(2) INFORMATION FOR SEQ ID NO: 103:

(i) SEQUENCE CHARACTERISTICS:
(A) LENGTH: 55 amino acids
(B) TYPE: amino acid
(D) TOPOLOGY: linear (xi) SEQUENCE DESCRIPTION: SEQ ID NO: 103:

```
Met Gln Trp Asn Ser Thr Thr Leu His Gln Ala Leu Gln Asp Pro Arg
  1               5                  10                  15

Val Arg Gly Leu Tyr Phe Pro Ala Gly Gly Ser Ser Ser Gly Thr Leu
             20                  25                  30

Asn Pro Val Pro Asn Thr Ala Ser His Ile Ser Ser Val Phe Ser Thr
         35                  40                  45

Thr Gly Asp Pro Ala Pro Asn
     50                  55
```

(2) INFORMATION FOR SEQ ID NO: 104:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 104:

```
ACGCAGATCT CCATCGCCGC GTCGCAGAAG ATCTCAATCT CGGGAATCTC AATGTTAGTA     60

TTCCTTGGAC TCATAAGGTG GGAAACTTTA CGGGGCTTTA TTCCTCTACA GTACCTATCT    120

TTAATCCTGA ATGGCAAACT CCTTCCTTTC CTAAGATTCA TTTACAAGAG GACATTATTA    180
```

-continued

```
ATAGGTGTCA ACAATTTGTG GGCCCTCTCA CTGTAAATGA AAAGAGAAGA TTGAAATTAA    240

TTATGCCTGC TAGATTCTAT CCTACCCACA CTAAATATTT GCCCTTAGAC AAAGGAATTA    300

AACCTTATTA TCCAGATCAG GTAGTTAATC ATTACTTCCA AACCAGACAT TATTTACATA    360

CTCTTTGGAA GGCTGGTATT CTATATAAGC GGGAAACCAC ACGTAGCGCA TCATTTTGCG    420

GGTCACCATA TTCTTGGGAA CAAGAGCTAC AGCATGGGAG GTTGGTCATC AAAACCTCGC    480

AAAGGCATGG GGACGAATCT TTCTGTTCCC AATCCTCTGG GATTCTTTCC CGATCATCAG    540

TTGGACCCTG CATTCGGAGC CAACTCAAAC AATCCAGATT GGGACTTCAA CCCCGTCAAG    600

GACGACTGGC CAGCAGCCAA CCAAGTAGGA GTGGGAGCAT TCGGGCCAAG GCTCACCCCT    660

CCACACGGCG GTATTTTGGG GTGGAGCCCT CAGGCTCAGG GCATATTGAC CACAGTGTCA    720

ACAATTCCTC CTCCTGCCTC CACCAATCGG CAGTCAGGAA GGCAGCCTAC TCCCATCTCT    780

CCACCTCTAA GAGACAGTCA TCCTCAGGCC ATGCAGTGGA A                        821
```

(2) INFORMATION FOR SEQ ID NO: 105:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 105:

```
ACGAAGGTCT CAATCGCCGC GTCGCAGAAG ATCTCAATCT CGGGAATCCC AATGTTAGTA     60

TCCCTTGGAC TCATAAGGTG GGAAACTTTA CTGGGCTTTA TTCTTCTACT GTACCTGTCT    120

TTAATCCTGA ATGGCAAACT CCCTCTTTTC CTGACATTCA TTTGCAGGAG GACATTATTA    180

ATAGATGTCA ACAATATGTG GGCCCTCTTA CAGTTAATGA AAAAAGAAGA TTAAAATTAA    240

TTATGCCTGC TAGGTTTTAT CCTAACCTTA CTAAATATTT GCCCTTAGAC AAAGGCATTA    300

AACCTTATTA TCCAGAACAG ACAGTTAATC ATTACTTCAA AACTAGGCAT TATTTGCATA    360

CTCTGTGGAA GGCTGGTAGT CTATATAAGA GAGAAACTAC ACGCAGCGCC TCATTTTGTG    420

GGTCACCATA TTCTTGGGAA CAAGAGCTAC AGCATGGGAG GTTGGTCTTC AAAACCTCGG    480

AAAGGCATGG GGACGAATCT TTCGGTACCC AATCCTCTGG GATTCTTTCC CGATCACCAG    540

TTGGACCCTG CGTTCGGAGC CAACTCAAAC AATCCCGATT GGGACTTCAA CCCCAACAAG    600

GATCACTGGC CAGAGGCAAA TCAGGTAGGA GCGGGAGCAT TCGGGCCAGG GTTCACCCCA    660

CCACACGGAG GTCTTTTGGG GTGGAGCCCT CAGGCCCAGG GCATATTGAC AACAGTGCCA    720

GCAGCTCCTC CTTCTGCCTC CACCAATCGG CAGTCAGGAA GACAGCCTAC GCCCATCTCT    780

CCACCTCTAA GAGACAGTCA TCCTCAGGCC ATGCAGTGGA A                        821
```

(2) INFORMATION FOR SEQ ID NO: 106:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 106:

```
ACGAAGGTCT CAATCACCGC GTCGCAGAAG ATCTCAATCT CGGGAATCCC AATGTTAGTA     60

TCCCTTGGAC TCATAAGGTG GGAAACTTTA CTGGGCTTTA TTCTTCTACT GTACCTGTCT    120

TTAATCCTGA ATGGCAAACT CCCTCTTTTC CTGACATTCA TTTGCAGGAG GACATTATTA    180

ATAGATGTCA ACAATATGTG GGCCCTCTTA CAGTTAATGA AAAAAGAAGA TTAAAATTAA    240
```

-continued

TTATGCCTGC TAGGTTTTAT CCTAACCTTA CCAAATATTT GCCCTTAGAT AAAGGCATTA 300

AACCTTATTA TCCTGAACAT GCAGTTAATC ATTACTTCAA AACAAGGCAT TATTTACATA 360

CTCTGTGGAA GGCTGGCATC TTATATAAAA GAGAAACTAC ACGCAGTGCC TCATTTTGTG 420

GGTCACCATA TTCTTGGGAA CAAGAGCTAC AGCATGGGAG GTTGGTCTTC CAAACCTCGG 480

AAAGGCATGG GGACGAATCT TTCTGTTCCC AATCCTCTGG GATTCTTTCC CGATCACCAG 540

TTGGACCCTG CATTCGGAGC CAACTCAAAC AATCCAGATT GGGACTTCAA CCCCAACAAG 600

GATCAATGGC CAGAGGCAAA TCAGGTAGGA GCGGGAGCAT TCGGGCCAGG GTTCACCCCA 660

CCACACGGAG GTCTTTTGGG GTGGAGCCCT CAGGCACAAG GCATATTGAC AACACTGCCA 720

GCAGCTCCTC CTCCTGGCTC CACCAATCGG CAGTCAGGAA GACAGCCTAC GCCCATCTCT 780

CCACCTCTAA GAGACAGTCA TCCTCAGGCC ATGCAGTGGA A 821

(2) INFORMATION FOR SEQ ID NO: 107:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 107:

ACGAAGATCT CAATCGCCGC GTCGCAGAAG ATCTCAATCT CCAGCTTCCC AATGTTAGTA 60

TCCCTTGGAC TCATAAGGTG GGAAATTTTA CGGGGCTTTA CTCTTCTACT ATACCTGTCT 120

TTAATCCTAA CTGGAAAACT CCATCTTTTC CTGATATTCA TTTGCACCAG GACATTATTA 180

ACAAATGTGA ACAATTTGTA GGTCCTCTAA CTGTAAATGA AAAACGAAGA TTAAACTTAG 240

TCATGCCTGC TAGATTTTTT CCCATCTCTA CGAAATATTT GCCCCTAGAG AAAGGTATAA 300

AACCTTATTA TCCAGATAAT GTAGTTAATC ATTACTTCCA AACCAGACAC TATTTACATA 360

CCCTATGGAA GGCGGGCATC TTATATAAAA GAGAAACTAC ACGTAGCGCC TCATTTTGTG 420

GGTCACCTTA TTCTTGGGAA CAAGAGCTAC ATCATGGGGC TTTCTTGGAC GGTCCCTCTC 480

GAANNNTGGG GGAAGAATAT TTCCACCACC AATCCTCTGG GATTTTTTCC CGACCACCAG 540

TTGGATCCAG CATTCAGAGC AAACACCAGA AATCCAGATT GGGACCACAA TCCCAACAAA 600

GACCACTGGA CAGAAGCCAA CAAGGTAGGA GTGGGAGCAT TCGGGCCTGG GTTCACTCCC 660

CCACACGGAG GCCTTTTGGG GTGGAGCCCT CAGGCTCAAG GCATGCTAAA AACATTGCCA 720

GCAGATCCGC CTCCTGGCTC CACCAATCGG CAGTCAGGAA GGCAGCCTAC CCCAATCACT 780

CCACCTTTGA GAGACACTCA TCCTCAGGCC ATGCAGTGGA A 821

(2) INFORMATION FOR SEQ ID NO: 108:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 108:

ACGAAGATCT CAATCGCCGC GTCGCAGAAG ATCTCAATCT CCAGCTTCCC AATGTTAGTA 60

TCCCTTGGAC TCATAAGGTG GGAAATTTTA CGGGGCTCTA CTCTTCTACT ATTCCTGTCT 120

TTAATCCTAA CTGGAAAACT CCATCTTTTC CTGATATTCA TTTGCACCAG GACATTATTA 180

ACAAATGTGA ACAATTTGTA GGTCCTCTAA CAGTAAATGA AAAACGAAGA TTAAACTTAG 240

-continued

```
TCATGCCTGC TAGATTTTTT CCCATCTCTA CAAAATATTT GCCCCTAGAG AAAGGTATAA    300

AACCTTATTA TCCAGATAAT GTAGTTAATC ATTACTTCCA AACCAGACAC TATTTACATA    360

CCCTATGGAA GGCTGGGCAT CTATATAAAA GAGAAACTAC ACGTAGCGCC TCATTTTGTG    420

GGTCACCATA TTCTTGGGAA CAAGAGCTAC ATCATGGGGC TTTCTTGGAC GGTCCCTCTC    480

GAANNNTGGG GGAAGAATAT TTCCACCACC AATCCTCTGG GATTTTTTCC CGACCACCAG    540

TTGGATCCAG CATTCAGAGC AAACACCAGA AATCCAGATT GGGACCACAA TCCCAACAAA    600

GACCACTGGA CAGAAGCCAA CAAGGTAGGA GTGGGAGCCT TCGGGCCGGG GTTCACTCCC    660

CCACACGGAG GCCTTTTGGG GTGGAGCCCT CAGGCTCAAG GCATGCTAAA AACATTGCCA    720

GCAGACCCGC CTCCTGGCTC CACCAATCGG CAGTCAGGAA GGCAGCCTAC CCCAATCACT    780

CCACCTTTGA GAGACACTCA TCCTCAGGCC ATGCAGTGGA A                         821
```

(2) INFORMATION FOR SEQ ID NO: 109:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 109:

```
ACGAAGGTCT CAATCGCCGC GTCGCAGAAG ATCTCAATCT CCAGCTTCCC AATGTTAGTA     60

TCCCTTGGAC TCATAAGGTG GGAAATTTTA CGGGGCTCTA CTCTTCTACT GTACCTGCTT    120

TCAATCCTCA CTGGTAAACT CCTTCTTTTC CTGATATTCA TTTGCATCAA GACCTGATAT    180

CTAAATGTGA ACAATTTGTA GGCCCACTTA CCAAAAATGA ATTAAGAAGG TTGAAATTGA    240

TTATGCCAGC CAGATTCTTT CCCTAACTTA CTAAATATTT CCCTCTGGAG AAAGACATTA    300

AACCTTATTA TCCAGAGCAT GCAGTTAATC ATTATTTTCA AACCAGACAT TATTTGCATA    360

CTTTATGGAA GGCGGGAATT TTATATAAGA GAGAATCCAC ACGTAGCGCC TCATTTTGTG    420

GGTCACCATA TTCTTGGGAA CAAGAGCTAC AGCATGGAGC ACCTCTCTCA ACGACCAAGA    480

AGGGGCATGG GACAGAATCT CTCTGTGCCC AATCCACTGG GATTCTTTCC AGACCATCAA    540

CTGGATCCTC TTTTCAGAGC AAATTCCAGC AGTCCCGATT GGGACTTCAA CAAAAACAAG    600

GACACTTGGC CAATGGCAAA CAAGGTAGGA GTGGGAGGTT ACGGTCCAGG GTTCACACCC    660

CCACACGGTG GCCTGTTGGG GTGGAGCCCT CAGGCACAAG GTGTTCTAAC AACCTTGCCA    720

GCAGATCCGC CTCCTGGCTC CACCAATCGG CTGTCCGGGA GGAAGCCAAC CCCAGTCTCT    780

CCACCTCTAA GAGACACACA TCCACAGGCA ATGCAGTGGA A                         821
```

(2) INFORMATION FOR SEQ ID NO: 110:

(i) SEQUENCE CHARACTERISTICS:
(A) LENGTH: 821 base pairs
(B) TYPE: nucleic acid
(C) STRANDEDNESS: single
(D) TOPOLOGY: linear (xi) SEQUENCE DESCRIPTION: SEQ ID NO: 110:

```
ACGAAGGTCT CAATCGCCGC GTCGCAGAAG ATCTCAATCT CCAGCTTCCC AATGTTAGTA     60

TCCCTTGGAC TCATAAGGTG GGAAATTTTA CGGGGCTCTA CTCTTCTACT GTACCTGCTT    120

TCAATCCTAA CTGGTAAACT CCTTCTTTTC CTGATATTCA TTTACATCAG GATATGATAT    180

CTAAATGTGA ACAATTTGTA GGCCCGCTCA CTAAAAATGA ATTAAGAAGA TTAAAATTGG    240

TCATGCCAGC TAGATTTTAT CCTAAGCATA CCAAATATTT CCTACTGGAG AAAGGGATTA    300
```

-continued

```
AACCCTATTA TCCAGATCAG GCAGTTAATC ATTATTTTCA AACCAGACAT TATTTGCATA    360

CTTTATGGAA GGCGGGAATT CTATATAAGA GAGAAACCAC ACGTAGCGCC TCATTTTGTG    420

GGTCACATAT TCCTTGGGAA CAAGAGCTAC AGCATGGAGC ACCTCTCTCA ACGACCAAGA    480

AGGGGCATGG GACAGAATTT CTCTGTGCCC AATCCACTGG GCTTCTTGCC AGACCATCAG    540

CTGGATCCGC TATTCAGAGC AAATTCCAGC AGTCCCGACT GGGACTTCAA CACAAACAAG    600

GACAGTTGGC CAATGGCAAA CAAGGTAGGA GTGGGAGGCT ACGGTCCAGG GTTCACACCC    660

CCACACGGTG GCCTGCTGGG GTGGAGCCCT CAGGCACAGG GTGTTTTAAC AACCTTGCCA    720

GCAGATCCGC CTCCTGGTTC CACCAATCGG CTGTCCGGGA GGAAGCCAAC CCAAGTCTCT    780

CCACCTCTAA GAGACACACA TCCTCAGGCC ATGCAGTGGA A                        821
```

(2) INFORMATION FOR SEQ ID NO: 111:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 111:

```
TTCCACTGCC TTCCACCAAA CTCTGCAGGA TCCCAGAGTC AGGGGTCTGT ATCTTCCTGC     60

TGGTGGCTCC AGTTCAGGAA CAGTAAACCC TGCTCCGAAT ATTGCCTCTC ACATCTCGTC    120

AATCTCCGCG AGGACTGGGG ACCCTGTGAC GAACATGGAG AACATCACAT CAGGATTCCT    180

AGGACCCCTG CTCGTGTTAC AGGCGGGGTT TTTCTTGTTG ACAAGAATCC TCACAATACC    240

GCAGAGTCTA GACTCGTGGT GGACTTCTCT CAATTTTCTA GGGGGATCTC CCGTGTGTCT    300

TGGCCAAAAT TCGCAGTCCC CAACCTCCAA TCACTCACCA ACCTCCTGTC CTCCAATTTG    360
```

(2) INFORMATION FOR SEQ ID NO: 112:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 112:

```
CTCCACAACA TTCCAACAAG CTCTGCAGGA TCCCAGAGTC AGGGTCCTTT ATTTTCCTGC     60

TGGTGGCTCC AGTTCCGGAA CAGTAAACCC TGCTCCGACT ACTGCCTCTC TCATTTCGTC    120

AATCTTCTCG AGGATTGGGG ACCCTGTAAC GAACATGGAG AACACAACAT CAGGATTCCT    180

AGGACCCCTG CTCGTGTTAC AGGCGGGGTT TTTCTTGTTG ACAAAAATCC TCACAATACC    240

ACAGAGTCTA GACTCGTGGT GGACTTCTCT CAATTTTCTA GGGGGAGCAC CCGTGTGTCC    300

TGGCCAAAAT TCGCAGTCCC CAACCTCCAA TCACTCACCA ACCTCTTGTC CTCCAATTTG    360
```

(2) INFORMATION FOR SEQ ID NO: 113:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 113:

```
CTCCACAACA TTCCAACAAG CTCTGCTAGA TCCCAGAGTG AGGGGCCTAT ATTTTCCTGC     60

TGGTGGCTCC AGTTCCGGAA CAGTAAACCC TGTTCCGACT ACTGCCTCTC TCATTTCGTC    120
```

-continued

```
AATCTTCTCG AGGACTGGGG ACCCTGTAAC GAACATGGAG AACACAACAT CAGGATTCCT    180

AGGACCCCTG CTCGTGTTAC AGGCGGGGTT TTTCTTGTTG ACAAGAATCC TCACAATACC    240

ACAGAGTCTA GACTCGTGGT GGACTTCTCT CAATTTTCTA GGGGAAGCAC CAAGGTGTCC    300

TGGCCAAAAT TCGCAGTCCC CAACCTCCAA TCACTCACCA ACCTCTTGTC CTCCAATTTG    360
```

(2) INFORMATION FOR SEQ ID NO: 114:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 114:

```
TTCCACAACA TTCCACCAAG CTCTGCAGGA TCCCAGAGTA AGAGGCCTGT ATTTTCCTGC     60

TGGTGGCTCC AGTTCCGGAA CAGTGAACCC TGTTCCGACT ACTGCCTCAC TCATCTCGTC    120

AATCTTCTCG AGGATTGGGG ACCCTGCACC GAACATGGAA AGCATCACAT CAGGATTCCT    180

AGGACCCCTG CTCGTGTTAC AGGCGGGGTT TTTCTTGTTG ACAAAAATCC TCACAATACC    240

GCAGAGTCTA GACTCGGGGT GGACTTCTCT CAATTTTCTA GGGGGAGCTC CCGTGTGTCT    300

TGGCCAAAAT TCGCAGTCCC CAACCTCCAG TCACTCACCA ACCTCTTGTC CTCCAATTTG    360
```

(2) INFORMATION FOR SEQ ID NO: 115:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 115:

```
CTCCACAACA TTTCATCAAG CTCTGCAGGA TCCCAGAGTA AGAGGCCTGT ATTTTCCTGC     60

TGGTGGCTCC AGTTCCGGAA CAGTGAACCC TGTTCCGACT ACTGCCTCAC TCATCTCGTC    120

AATCTTCTCG AGGATTGGGG ACCCTGCACC GAACATGGAA AGCATCACAT CAGGATTCCT    180

AGGACCCCTG CTCGTGTTAC AGGCGGGGTT TTTCTTGTTG ACAAAAATCC TCACAATACC    240

GCAGAGTCTA GACTCGTGGT GGACTTCTCT CAATTTTCTA GGGGGAGCTC CCGTGTGTCT    300

TGGCCAAAAT TCGCAGTCCC CAACCTCCAA TCACTCACCA ACCTCTTGTC CTCCAATTTG    360
```

(2) INFORMATION FOR SEQ ID NO: 116:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 116:

```
CTCAACTCAC TTCCACCAGG CTCTGTTGGA TCCGAGGGTA AGGGCACTGT ATTTTCCTGC     60

TGGTGGCTCC AGTTCAGGCA CGCAGAACCC TGCTCCGACT ATTGCCTCTC TCACATCATC    120

AATCTCCTCG AAGACTGGGG GCCCTGCTAT GAACATGGAC AACATCACAT CAGGACTCCT    180

AGGACCCCTG CTCGTGTTAC AGGCGGTGTG TTTCTTGTTG ACAAAAATCC TCACAATACC    240

ACAGAGTCTA GACTCGTGGT GGACTTCTCT CAATTTTCTA GGGGGACTAC CCGGGTGTCC    300

TGGCCAAAAT TCGCAGTCCC CAACCTCCAA TCACTTACCA ACCTCCTGTC CTCCAACTTG    360
```

-continued (2) INFORMATION FOR SEQ ID NO: 117:

(i) SEQUENCE CHARACTERISTICS:
(A) LENGTH: 360 base pairs
(B) TYPE: nucleic acid
(C) STRANDEDNESS: single
(D) TOPOLOGY: linear (xi) SEQUENCE DESCRIPTION: SEQ ID NO: 117:

```
CTCAACTCAC TTCCACCAAG CTCTGTTGGA TCCCAGGGTA AHGGCACTGT ATTTTCCTGC     60

TGGTGGCTCC AGTTCAGGAA CACAGAACCC TGCTCCGACT ATTGCCTCTC TCACATCATC    120

AATCTCCTCG AAGACTGGGG GCCCTGCTAT GAACATGGAG AACATCACAT CAGGACTCCT    180

AGGACCCCTG CGCGTGTTAC AGGCGGTGTG TTTCTTGTTG ACAAAAATCC TCACAATACC    240

ACAGAGTCTA GACTCGTGGT GGACTTCTCT CAATTTTCTA GGGGGACTAC CCAGGTGTCC    300

TGGCCAAAAT TCGCAGTCCC CAACCTCCAA TCACTTACCA ACCTCCTGTC CTCCAACTTG    360
```

HEPADNAVIRUS RECEPTOR

CROSS REFERENCE TO RELATED APPLICATIONS

This application is a division of U.S. application Ser. No. 08/683,262 (now U.S. Pat. No. 5,929,220), filed Jul. 18, 1996, which claims priortity from U.S. provisional application Ser. No. 60/001,371, filed Jul. 21, 1995.

This invention was supported in part by grants from the National Institutes of Health. The government has certain rights to the invention.

BACKGROUND OF THE INVENTION

The field of the invention is cellular receptors for viruses of the family Hepadnaviridae, and nucleic acids encoding the same.

The human hepatitis B virus (HBV) and related animal viruses that infect woodchucks, ground squirrels, Pekin ducks, and herons form a group of hepatotropic DNA viruses in the family Hepadnaviridae. In humans, HBV causes acute and chronic liver disease and hepatocellular carcinoma.

The initial event of infection, interaction between the viral envelope protein and specific cellular receptor(s), is poorly understood. Hepadnaviruses express at least two co-terminal envelope proteins from a single envelope gene by alternative use of in-frame AUG codons. The large envelope protein (pre-S/S protein) of duck hepatitis B virus (DHBV) contains a 161–163 amino acid segment called the pre-S domain, and a carboxylterminal 167 amino acid segment called the S domain. The small envelope protein (S protein alone) is produced by translation from an internal AUG codon. The large envelope protein of HBV is similar, but has pre-S1 and pre-S2 domains in place of the single DHBV pre-S domain. As a result, two pre-S containing proteins are produced: a large envelope protein (preS1+preS2+S) and a middle envelope protein (preS2+S). The large envelope protein is myristylated and phosphorylated (Grgacic et al., *J. Virol.* 68:7344–7350, 1994; Macrae et al., *Virology* 181:359–363, 1991; Persing et al., *J. Virol.* 61:1672–1677, 1987). The large envelope protein mediates infection by DHBV and by hepatitis delta virus (HDV), which borrows the envelope proteins of other hepadnaviruses to enter a hepatocyte (Fernholz et al., *Virology* 197:64–73, 1993; Summers et al., *J. Virol.* 65:1310–1317, 1991; Sureau et al., *J. Virol.* 67:366–372). The pre-S domain is believed to be responsible for binding a cellular receptor. Although several cellular proteins bind the HBV envelope, none have been shown to be the actual receptor (Budkowska et al., *J. Virol.* 67:4316–4322, 1993; Budkowska et al., *J. Virol.* 69:840–848, 1995; Hertogs et al., *Virology* 197:549–557, 1993; Mehdi et al., *J. Virol.* 68:2415–2424, 1994; Neurath et al., *J. Exp. Med.* 176:1561–1569, 1992; Pontisso et al., *J. Gen. Virol.* 73:2041–2045, 1992).

Since no cell culture system is available for the study of HBV, DHBV was developed as a model system. DHBV infection of ducklings and primary duck hepatocytes has been well characterized (Pugh et al., *Virology* 172:564–572, 1989; Tuttleman et al., *J. Virol.* 58:17–25, 1986).

SUMMARY OF THE INVENTION

The invention features a purified nucleic acid that encodes a member of the hepadnavirus family of cellular receptors, or, where the receptor is a complex of two or more polypeptides, a component thereof. By "a member of the hepadnavirus family of cellular receptors" (hereafter a "hepadnavirus receptor") is meant a protein that binds the pre-S domain of the hepadnavirus large envelope protein so as to mediate or induce entry of a hepadnavirus virion into a host cell. A "hepadnavirus receptor", as used herein, can be the whole receptor, where the receptor is a monomer, or a subunit of a hepadnavirus receptor that binds the pre-S receptor binding site of the pre-S domain.

The identity of a hepadnavirus receptor that "mediates entry of the hepadnavirus virion into a host cell" can be confirmed using two biological activity assays. First, an antibody preparation specific for a member of the hepadnavirus family of receptor proteins should have the ability to block, inhibit, or reduce hepadnaviral infection of, or entry into, a cell, the virus being capable of infecting the same cell type in the absence of antibody. Either polyclonal or monoclonal receptor-specific antibodies can be used. For the second assay, a cDNA that encodes a member of the hepadnavirus family of receptor proteins is transfected into a cell line. The cell line is one that is ordinarily not a target cell for a hepadnavirus. Transfection of receptor-encoding cDNA sequence into these cells should confer properties on the cell line that enable them to be infected by a hepadnavirus, or enable the virus to bind to the cell surface. By performing these two aforementioned assays, a hepadnavirus receptor is distinguished from a non-receptor hepadnavirus pre-S binding protein.

By "purified nucleic acid" is meant a nucleic acid that is not immediately contiguous with both of the coding sequences with which it is immediately contiguous (i.e., one at the 5' and one at the 3' end) in the naturally-occurring genome of the organism from which the nucleic acid of the invention is derived. The term encompasses deoxyribonucleic acid (DNA), for example, a cDNA or a genomic DNA fragment produced by the polymerase chain reaction (PCR), or produced by restriction endonuclease treatment. The cDNA or genomic DNA fragment can be incorporated into a vector, integrated into the genome of the same or a different species than the organism from which it was originally derived, linked to an additional coding sequence to form a hybrid gene encoding a chimeric polypeptide, or independent of any other nucleic acid sequences. The term also encompasses ribonucleic acid (RNA). The nucleic acid may be double-stranded or single-stranded, sense or antisense.

Examples of purified nucleic acids of the invention include those which encode amino acid sequences substantially the same as those shown in FIGS. 18 and 19; and those having sequences that are either identical to, or hybridize under conditions of high or moderate stringency to, the 2.5 kb p170 cDNA included in the ATCC deposit Ep170pUC, designated No. 69869. High stringency conditions are herein defined as the following: hybridizing with 50% deionized formamide, 800 mM NaCl; 20 mM Pipes, pH 6.5, 0.5% SDS, 100 μg/ml denatured, sonicated salmon sperm DNA at 42° C. for 12–20 hours, washing with 30 mM NaCl/3.0 mM sodium citrate (0.2×SSC)/0.1% SDS at 55° C., while moderate stringency conditions are as follows: hybridizing with 50% deionized formamide, 800 mM NaCl; 20 mM Pipes, pH 6.5, 0.5% SDS, 100 μg/ml denatured, sonicated salmon sperm DNA at 42° C. for 12–20 hours, washing with 75 mM NaCl/7.5 mM sodium citrate (0.5×SSC)/0.1% SDS at 55° C. Such hybridization conditions are useful in a method of identifying a nucleic acid sequence encoding a hepadnavirus receptor polypeptide. The method involves providing a genomic or cDNA library; contacting the library with a nucleic acid that encodes a portion of a hepadnavirus receptor, e.g., the duck p170 receptor, under conditions permitting hybridization between the nucleic acid and a homologous nucleotide sequence in the library; and identifying a clone from the library which hybridizes to the nucleic acid, hybridization being indicative of the presence in the clone of a nucleotide sequence homologous to a hepadnavirus receptor-encoding nucleotide sequence.

The invention also includes fragments of a purified nucleic acid that encodes a member of the hepadnavirus family of receptors. Examples include a nucleic acid of at least 20 nucleotides in length, or at least 30 or 50 nucleotides in length, that includes a strand which hybridizes under high stringency conditions to either the sense or antisense strand of a nucleic acid encoding part or all of a naturally occurring hepadnavirus receptor polypeptide. A nucleic acid fragment is useful, e.g., as a probe for identifying additional members of the hepadnavirus family of receptors, or for administering a portion of a hepadnavirus receptor sequence to a cell, e.g., a cell in a patient, using gene therapy techniques. Such portions of a hepadnavirus can include the peptides 1–4 shown in FIG. 14A.

The invention also includes vectors (e.g., plasmids, phage, or viral nucleic acid) or cells (prokaryotic or eukaryotic) which contain nucleic acids encoding any of the various hepadnavirus receptors of the invention. The vector can be any vector suitable for maintaining or making multiple copies of a nucleic acid of the invention, or can be one that is suitable for administering a nucleic acid of the invention to a cell or to a mammal infected with a hepadnavirus, e.g., to a human patient infected with HBV, or to cells removed from the patient for ex vivo gene therapy. Examples of vectors useful in a method of inhibiting hepadnavirus replication include, but are not limited to, adenovirus vectors, adeno-associated vectors, and retroviral vectors. Any of the various vectors of the invention can be included in a therapeutic composition along with a pharmaceutically acceptable carrier.

A purified nucleic acid of the invention can be under the transcriptional control of a heterologous promoter (i.e., a promoter other than one naturally associated with the given receptor gene of the invention). The promoter may direct the expression of the nucleic acid of the invention in a particular tissue or at a particular stage of development. A nucleic acid of the invention can also be in the form of a transgene in a transgenic non-human animal, e.g., in a mouse. A transgenic animal bearing a transgene that encodes a hepadnavirus receptor is useful as an animal model to assay potential reagents for treating a hepadnavirus infection.

The invention also features hepadnavirus receptor polypeptides encoded by any of the various nucleic acids of the invention, for example, recombinant polypeptides expressed by a cell transformed with the nucleic acid. The polypeptide can be included in a therapeutic composition as an active ingredient, along with a pharmaceutically acceptable carrier, or it can be expressed from the nucleic acid within a target cell. The invention also includes an antibody that forms an immune complex with a hepadnavirus receptor of the invention. The antibody can be included in a therapeutic composition along with a pharmaceutically-acceptable carrier, or can be packaged in the form of a kit to be used as a diagnostic reagent. As a therapeutic, the antibody is useful for reducing the level of hepadnaviral infection in an animal, e.g., a human patient. The method involves administering a therapeutic preparation of the antibody to the animal in a dosage effective to inhibit the infection.

The invention also features a ligand that binds a member of the hepadnavirus family of receptors, hereafter referred to as a "p170 ligand." By "p170 ligand" is meant a molecule that specifically binds to the p170 binding site in the pre-S domain, in a mode that is competitive with the naturally-occurring hepadnavirus envelope. Preferably, a p170 ligand is a portion of the pre-S domain (hereafter a pre-S polypeptide) which binds the hepadnavirus receptor. The amino acid sequence of a pre-S polypeptide is substantially identical to a region of a wild type hepadnavirus pre-S domain (see, e.g., FIGS. 16 and 17), the region being smaller in length than the complete amino acid sequence of the wild type pre-S domain, and being one that binds to a hepadnavirus receptor. A pre-S polypeptide of the invention is at least twelve amino acids, preferably at least nine amino acids, or more preferably at least six amino acids in length. By "binds to a hepadnavirus receptor" is meant that the p170 ligand forms a specific interaction with the receptor sufficient for copurification of the two components by an antibody specific for one of them. Alternatively, binding is indicated by co-purification on a GST affinity column, as described herein.

Where the hepadnavirus is DHBV, the aminoterminal amino acid of the pre-S p170 polypeptide amino acid sequence corresponds to a position selected from the group consisting of positions 1 to 87, or amino acids 25 to 87, 59 to 87, 70 to 87, or 80 to 87, all inclusive, of the amino acid sequence of FIG. 16. The carboxylterminal amino acid of the amino acid sequence can correspond to a position selected from the group consisting of positions 102 to 161, 104 to 161, 126 to 161, or 138 to 161, all inclusive, of the amino acid sequence of FIG. 16. Examples of pre-S polypeptides of the invention can include, but are not limited to, those including amino acids 25–161, 59–161, 71–161, 80–161, 87–161, 1–138, 1–126, 1–104, 1–102, 25–104, 25–102, 80–104, 25–126, 59–126, 71–126, 42–102, 59–104, all inclusive. Since applicants have identified the two basic amino acid residues at positions 95 and 97 as being essential for binding to the hepadnavirus receptor, it is recognized that a pre-S polypeptide encompassing amino acids 95 and 97 is a suitable p170 ligand. The full DHBV pre-S p170 nucleotide and amino acid sequences are shown in FIG. 16 (Mandart et al., *J. Virol.,* 49:782–792, 1984).

Corresponding regions of the receptor binding site in the human HBV pre-S domain will be easily identified from the sequence alignment shown in FIG. 20, and by routine techniques of sequence analysis. For example, the receptor binding site in the HBV pre-S domain includes amino acids 89–104. The aminoterminal amino acid of the binding site preferably corresponds to one of the amino acids between positions 71 and 89, inclusive, of the amino acid sequence of FIG. 20. The carboxylterminal amino acid of the receptor binding site preferably corresponds to one of the amino acids between positions 104 to 118, inclusive, of FIG. 20. Examples of HBV pre-S polypeptides of the invention can include, but are not limited to, those including amino acids 89–104, or 71–118, of FIG. 20. Since applicants have identified the arginine residue at position 99 as being essential for binding to the hepadnavirus receptor, it is recognized that a pre-S polypeptide encompassing amino acid 99 is a suitable hepadnavirus receptor ligand. The full HBV pre-S nucleotide and amino acid sequences of several strains that infect primates are shown in FIG. 17 (Norder et al., *Virology,* 198:489–503, 1994). Using pre-S protein fused to glutathione S-transferase and immobilized on Sepharose beads, we have now identified an additional binding protein of 120-kDa (p120). p120 expression is restricted to the liver, kidney and the pancreas, the three major organs of DHBV replication. While optimal p170 binding requires intact pre-S protein, binding to p120 occurs much more efficiently with a few N- or C-terminally truncated forms. The p120 binding site was mapped to residues 98–102 of the pre-S region, which overlaps with a cluster of known virus-neutralizing epitopes. Site-directed mutagenesis revealed residues 100–102 (Phe-Arg-Arg) as the critical p120 contact site; non-conservative substitution in any of the three positions abolished p120 binding. Double mutations at positions 100–102 markedly reduced DHBV infectivity in cell culture. Short pre-S peptides covering the clustered neutralizing epitopes (also p170/p120 binding sites) reduced DHBV infectivity in primary duck hepatocyte cultures. Thus, p120 represents a candidate component of the DHBV receptor complex.

The hepadnavirus receptors and pre-S polypeptides of the invention can be fused to a glutathione-S-transferase amino acid sequence (Smith et al., *Gene* 67:31, 1988). The polypeptide can be glycosylated or unglycosylated. "Glycosylated", as used herein, refers to having one or more covalently-linked carbohydrate moieties attached to the protein. By "unglycosylated" is meant lacking covalently-linked carbohydrate moieties. The hepadnavirus receptor can also be myristylated or unmyristylated, or phosphorylated or unphosphorylated, meaning that the hepadnavirus receptor or pre-S polypeptide has one or more covalently-attached myristic acid or phosphate groups, respectively.

The invention also includes a vaccine for the prevention of a hepadnaviral infection. A vaccine can be in the form of either an immunologically cross-reactive form of a naturally-occurring hepadnavirus receptor, or a nucleic acid encoding the same. A vaccine of the invention can also be in the form of a pre-S polypeptide, or a nucleic acid encoding a pre-S polypeptide. Where the vaccine is administered as a live cell vaccine, it may be desirable to inactivate the ability of the pre-S polypeptide to activate the receptor. Thus, a codon corresponding to an amino acid residue of the naturally occurring pre-S polypeptide can be deleted or altered to encode an amino acid residue different from the amino acid residue of the naturally occurring pre-S polypeptide; for the p170 ligand, this is preferably an amino acid residue selected from the group consisting of amino acids 95 and 97. Examples of suitable mutations of p170 include, but are not limited to, a substitution of Arg to Leu at position 95 (R95L), a substitution of Lys to Ser at position 95 (K95S), or a substitution of Arg to Cys at position 97 (R97C) of the sequence of FIG. 16. Codons encoding the hepadnavirus receptor binding-site of p170 can also be deleted from the vaccine, e.g., by a deletion of all of the codons encoding binding site amino acids, e.g., amino acids 87 to 102, or by deleting codons encoding amino acids 95 and 97, from the nucleic acids, thereby to delete receptor-binding capacity from the polypeptide it encodes. Corresponding modifications of p120 can be made and used in vaccines. Such polypeptide and nucleic acid-based vaccines are useful in a method of immunizing an animal against hepadnaviral infection, by introducing an immunizing amount of the nucleic acid or polypeptide into the animal.

Also encompassed within the invention is a method of producing a hepadnavirus receptor polypeptide, by the steps of (a) providing the cell that includes a nucleic acid encoding a hepadnavirus receptor; and (b) culturing the cell under conditions permitting expression of the polypeptide from the nucleic acid.

Finally, the invention includes a method for identifying an antagonist to a hepadnavirus receptor. The method involves (a) contacting a hepadnaviral receptor, in the presence and in the absence of the candidate antagonist, with a form of hepadnavirus envelope protein; and (b) comparing the level of binding of the receptor to the form of hepadnavirus envelope protein in the presence of the candidate antagonist, with the level of binding of the receptor to the form of hepadnavirus envelope protein in the absence of the candidate antagonist. A lower level of binding in the presence of the candidate antagonist than in its absence indicates that the candidate antagonist is capable of competing with the form of hepadnavirus envelope protein for binding to the receptor. "Antagonist", as used herein, refers to a chemical substance that inhibits an activity of the receptor, such as its ability to bind a ligand or agonist, e.g., a hepadnavirus. A "form of hepadnavirus envelope protein" can be a naturally occurring hepadnavirus; a hepadnavirus envelope particle; a hepadnavirus subparticle; an envelope protein; a hepadnavirus pre-S protein; or a pre-S polypeptide of at least six amino acids that includes the hepadnavirus receptor-binding domain as characterized herein. The hepadnaviral receptor polypeptide can be provided in the form of a cultured eukaryotic cell transfected with a nucleic acid that encodes a hepadnavirus receptor, the receptor being expressed in the cell preferably as a cell surface receptor. The hepadnaviral receptor can also be provided in the form of a transgenic non-human animal bearing a transgene, the transgene including a nucleic acid that encodes a hepadnavirus receptor as a source of the receptor.

As used herein, a "hepadnavirus" refers to a member of the Hepadnavirdae family of viruses, including, but not limited to, hepatitis B virus and hepatitis delta virus (Wang et al., Nature, 323:508–13, 1986). Cellular receptors that interact with other hepadnavirus species are included within the scope of the invention. Examples include, but are not limited to, avian strains such as duck hepatitis B virus (DHBV; Mandart et al., *J. Virol.* 49:782–792, 1984; Mason et al. J. Virol. 36:829–36, 1978), or heron HBV (Sprengel et al., J. Virol., 62:3832–39, 1988); woodchuck hepatitis virus (WHV; Summers et al. Proc. Natl. Acad Sci. USA, 75:4533–37, 1978), and squirrel hepatitis virus (e.g., Marion et al. Proc. Natl. Acad Sci. USA, 77:2941–45, 1980). These species can be useful laboratory models of the human hepatitis B virus. Examples of other hepadnaviruses within the scope of the invention include, but are not limited to, HBV strains infecting various human organs, including liver cells, exocrine and endocrine cells, tubular epithelium of the kidney, spleen cells, leukocytes, lymphocytes, e.g., splenic, peripheral blood, B or T lymphocytes, and cells of the lymph nodes and pancreas (see, e.g., Mason et al., Hepatology, 9:635–645, 1989). Various HBV strains within the scope of the invention include those disclosed by Norder et al., J. Virol., 198:489–503, 1994). The invention also applies to hepadnaviruses infecting non-human mammalian species, such as domesticated livestock or household pets. Nucleic acids derived from any of these species are useful for identifying and isolating further members of the hepadnavirus family of cellular receptors.

Where the method of inhibiting hepadnavirus replication is used to treat a hepadnaviral infection in an animal, a "naturally-occurring" hepadnavirus refers to a form or sequence of the virus as it exists in an animal, e.g., a natural isolate derived from an infected animal. In all other contexts, a "naturally-occurring" hepadnavirus is intended to be synonymous with the sequence known to those skilled in the art as the "wild type" sequence, e.g., the wild type pre-S protein sequences shown in FIGS. 16 and 17. If an amino acid sequence of a pre-S protein of a hepadnavirus that is derived from a natural isolate differs from the conventionally accepted "wild type" sequence, it is understood that the sequence of the natural isolate may be the proper comparison sequence for designing mutant polypeptides of the invention. The sequence of the natural isolate can be compared to the sequences cited herein to identify a receptor binding domain analogous to that of the DHBV pre-S domain.

Other terms and definitions used herein will be understood by those of routine skill in the art. For example, by "apparent molecular weight" is meant the molecular weight determined on a denaturing polyacrylamide gel by comparison with standards, e.g., protein standards, of known molecular weight. "Receptor", as used herein, refers to a molecule on the surface of a target cell that binds to and permits entry of its target ligand into the cell, e.g., a ligand such as a hepadnavirus virion. By "inhibiting hepadnavirus replication" is meant lowering the rate or extent of replication relative to replication in the absence of a mutant polypeptide of the invention. The term "fragment", as applied to a polypeptide will ordinarily be at least about 6 contiguous amino acids, typically at least about 9 or 12 contiguous amino acids, more typically at least about 20, or preferably at least about 30 or 35 or more contiguous amino acids in length. The term "fragment" as applied to a nucleic acid will ordinarily be at least about 15, typically at least about 20 or 30, more typically at least about 50, bp in length.

The methods, nucleic acids, and polypeptides of the invention can be used to inhibit entry of a hepadnavirus into a host cell, e.g., a cell of a mammal, e.g., a human patient, as an effective therapy for treating individuals with a persistent HBV infection, or as a means of reducing the risk of hepatocellular carcinoma in an infected animal. Polypeptides of the invention can be administered to an infected animal either directly or by gene therapy techniques. The screening methods of the invention are simple, rapid, and efficient assays designed to identify candidate antagonists or ligands, e.g., pre-S polypeptide ligands, with anti-hepadnaviral activity.

Other features and advantages of the invention will be apparent from the following detailed description and from the claims.

BRIEF DESCRIPTION OF THE DRAWINGS

FIG. 12 is a chart showing the location and nature of amino acid substitutions in mutants of the DHBV pre-S domain (SEQ ID NO:18).

FIG. 14A is an illustration of four peptide sequences from p170 (SEQ ID NOS:19–22).

FIG. 14B shows the sequence similarity of peptides 1 (SEQ ID NO:19) and 2 (SEQ ID NO:20) to various carboxypeptidases.

FIG. 15 is an illustration of cloning p170 DNA from the p170 peptide sequences (SEQ ID NOS:23–32).

FIG. 16 is an illustration of the nucleic acid sequence (SEQ ID NO:33) of the DHBV pre-S gene and the corresponding translated amino acid sequence (SEQ ID NO:34).

FIG. 18 is an illustration of the nucleic acid sequence (SEQ ID NO:63) of the 5' 1.1 kb of the p170 cDNA and the corresponding translated amino acid sequence (SEQ ID NO:64).

FIG. 19 is an illustration of the nucleic acid sequence (SEQ ID NO:65) of the 3' 460 bp of the p170 cDNA and the corresponding translated amino acid sequence (SEQ ID NO:66).

FIG. 20 is an illustration of the pre-S amino acid sequence in human HBV (SEQ ID NO:67) that corresponds to the p170 binding site in the DHBV pre-S protein (SEQ ID NO:68).

FIG. 30 is a set of p120 peptides (SEQ ID NOS:70–73).

FIG. 31 is the nucleic acid sequence (SEQ ID NO:74) and deduced amino acid sequence (SEQ ID NO:75) of the p120 and cDNA alone.

DEPOSIT

Figure 1A:
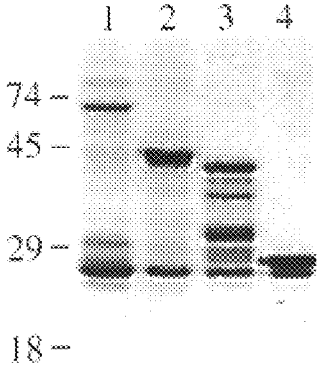
FIG. 1A is a Coomassie-blue stained SDS-polyacrylamide gel showing the migration of Glutathione-S-transferase (GST) fusion proteins. The molecular size of the protein markers are shown to the left.

Under the terms of the Budapest Treaty on the International Recognition of the Deposit of Microorganisms for the Purpose of Patent Procedure, a deposit of the plasmid Ep170pUC has been made with the American Type Culture Collection (ATCC) of Rockville, Md., USA, where the deposit was given Accession No. 69869.

Applicants' assignee, the General Hospital Corporation, represents that the ATCC is a depository affording permanence of the deposit and ready accessibility thereto by the public if a patent is granted. All restrictions on the availability to the public of the material so deposited will be irrevocably removed upon the granting of a patent. The material will be available during the pendency of the patent application to one determined by the Commissioner to be entitled thereto under 37 CFR 1.14 and 35 U.S.C. §122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicants' assignee acknowledges its duty to replace the deposit should the depository be unable to furnish a sample when requested due to the condition of the deposit.

DETAILED DESCRIPTION

Applicants have identified cellular receptors that specifically interact with the pre-S domain of the DHBV envelope protein. One receptor is a 170 kD cell surface glycoprotein, and is referred to as the p170 receptor. Applicants have mapped the p170 binding site to a major neutralizing epitope of the pre-S domain (amino acids 87–102), within which are two basic amino acids required for virion-receptor interaction. A 46 amino acid pre-S polypeptide covering this binding site inhibits DHBV infection of primary duck hepatocytes. We have also identified an additional pre-S binding protein of 120-kDa (p120). The possible role of p120 as part of the DHBV receptor complex is suggested by its restricted expression in DHBV infectible tissues, by co-localization of its binding site with three virus neutralizing epitopes, and by markedly decreased infectivity of DHBV mutants constructed with impaired p120 binding motif.

Materials and Methods

Cloning and expression of p170 sequences in *E. coli*: As a negative control, the pre-S domain of DHBV (FIG. 16; Tong et al., *Virology* 176:596–603, 1990) was amplified by the polymerase chain reaction (PCR)(Saike et al., Science 239:487, 1988), using the sense primer 5'-GC AGATCTATGGGCAGAATCTTTCCAC-3' (SEQ ID NO:1) (underlined untemplated BglII site for cloning) and the antisense primer 5'-GT GAATTCAGCGCAGGGTCCCCAAT-3' (SEQ ID NO:2) (underlined EcoRI site). Twenty cycles of amplification were carried out using 1 ng of HBV DNA and 1 unit of vent DNA polymerase (New England Biolabs). The PCR product was purified from an agarose gel, digested with BglII and EcoRI, and cloned between the BamHI and EcoRI sites of the PGEX 2TK vector (Pharmacia), which carries coding sequences for the GST protein. DNA fragments of DHBV covering the entire envelope gene (pre-S/S), the pre-S domain, and portions of the pre-S domain were generated by PCR (FIG. 16; Mandart et al., supra). Extra nucleotides for the BglII or BamHI site were put at the 5' end of the sense primers, while extra nucleotides for an in-frame stop codon and an EcoRI site were added at the 5' end of the antisense primer. Twenty cycles of amplification were carried out with one unit of vent DNA polymerase (New England Biolabs) and 1–10 ng of DHBV-16 DNA (Mandart et al., supra). The PCR products were cloned into the BamHI/EcoRI sites of pGEX 2TK. The sense primer for the preS region was: 5'-TCAGATCTATGATGGGGCAACATCCAGC-3' (SEQ ID NO:3) (underlined BglII site). The antisense primer for the end of the pre-S region: 5'-GCGAATTCAGGTACCAGACATTTTCTTCTT-4' (SEQ ID NO:4) (underlined EcoRI site). The antisense primer for the end of the S region: 5'-GCGAATTCTTATTCCTAACTCTTGTAA-3' (SEQ ID NO:5) (underlined EcoRI).

Pre-S deletion mutants are designated by the positions of the first and last pre-S amino acid residues included in the fragment. For example, pre-S(25–104) expressed amino acid residues 25 through 104 of the DHBV pre-S domain. Several pre-S deletion mutants with the 3' ends of the inserts located at the XhoI, SmaI, or HindIII site of DHBV (corresponding to pre-S amino acid 138, amino acid 126, and amino acid 97, respectively) were constructed through double enzymatic digestion of recombinant 2TK plasmids. For example, pre-S(25-126) was generated by removing a short SmaI-EcoRI fragment from pre-S(25–161), with subsequent filling-in of the sticky ends and recircularization of the plasmid by blunt-end ligation. Since a termination codon did not follow the insert immediately, fusion proteins expressed from these particular constructs contained a few miscellaneous amino acid residues at the carboxylterminus derived from the vector sequence downstream of the EcoRI site.

To construct DHBV pre-S substitution mutants, a 1.4 kb EcoRI-BamHI fragment covering the entire pre-S domain was cloned into pAlter-II vector (Promega). Mutagenesis was performed according to supplier's protocol ("Altered sites II: in vitro mutagenesis system technical manual", Promega) from single stranded template DNA. Most mutations introduced or destroyed a restriction enzyme recognition site, so that loss of the restriction site could be monitored as an indication that mutagenesis was successful. Mutations were confirmed by DNA sequencing. The entire pre-S domain of the mutants was amplified and subcloned into PGEX 2TK. Substitution mutants are identified by a single letter for the wild-type amino acid, followed by the numerical position of the amino acid, and a letter for the mutant amino acid. Expression and purification of GST fusion proteins were based on the supplier's protocol (GST Gene Fusion System, Promega). Fusion proteins were expressed by induction with 0.1 mM IPTG for 1 hour and following sonication, purified through a glutathione-sepharose beads (at a ratio of about 1 μl bead per ml bacteria culture). For the expression of the entire pre-S/S fusion protein of DHBV, induction with IPTG lasted for 3 to 4 hrs. The size, purity and yield of recombinant proteins were analyzed by SDS-12% polyacrylamide gel electrophoresis (PAGE) followed by Coomassie blue staining.

Preparation and labeling of primary duck hepatocytes. DHBV-free Pekin ducklings less than two weeks of age were perfused sequentially with 0.5 mM EGTA and 0.5 mg/ml collagenase through the portal vein (Pugh et al., supra; Tuttleman et al., supra). Hepatocytes were seeded in petri dishes at approximately 90% confluency using Leibovitz's L-15 medium supplemented with 5% fetal calf serum. Subsequent cultures employed serum-free medium supplemented with 1–1.5% dimethyl sulfoxide (DMSO)(Pugh et al., supra). For metabolic labeling, cells were starved in methionine-free Dulbecco's modified Eagle medium (DMEM) for 1 hour, then incubated for 4 hours with L-15 medium supplemented with $^{35}$S-methionine (Amersham) or Tran$^{35}$S Label (New England Nuclear) at 0.1 mci/ml concentration. Cells from each 60 mm dish were treated with 2 ml lysis buffer (50 mM Tris-Hcl, pH 7.5, 150 mM NaCl, 1% Triton X100, 1% sodium deoxycholate) supplemented with the protease inhibitors aprotinin, leupeptin and PMSF. Nuclei were removed by centrifugation and lysates stored at −80° C. For cell surface labeling with $^{125}$I, hepatocytes were detached from a 100 mm petri dish by treatment with Versene/EDTA, washed and resuspended in 0.5 ml phosphate buffered saline solution (PBS). Cell viability was examined by trypan blue exclusion and found to be greater than 90%. Labeling was accomplished with 1 mci of $^{125}$I and 40 u of lactoperoxidase (Boehringer-Mannheim), and the labeling reaction was carried out for 20 minutes with four additions of 15 μl 0.04% $H_2O_2$ (Marchalonis et al. *Biochem. J.* 113:299–305, 1969). After removing free $^{125}$I by centrifugation, cells were lysed as described above.

As a control for cell surface labeling, $^{125}$I labeling of unfractionated liver proteins was performed. Frozen duck liver tissue was homogenized in lysis buffer and dialyzed overnight in 1.8% NaCl solution. Around 100 μg protein was labeled with 1 mci of $^{125}$I using the iodogen method (Fraker et al., *Biochem. Biophys. Res. Comm.* 80:849–57, 1978) Labeled proteins were recovered by chromatography through a Sephadex G50 column (Pharmacia).

Detection of pre-S binding proteins in labeled lysates. To reduce the levels of cellular proteins which bind to the GST component of the pre-S fusion protein or directly to the sepharose beads, labeled lysates were first preincubated twice at 4° C. with a mixture of empty sepharose beads and GST-bound beads. The beads were washed extensively and used as a negative control in 8% SDS-PAGE. The precleared lysates were then incubated at 4° C. for 6 to 16 hours with the specific GST-pre-S fusion protein. After extensive washing of the beads four times with lysis buffer, bound proteins were eluted from beads by heating to 95° C. for 5 minutes, and separated on 8% SDS-PAGE under denaturing conditions. Proteins retained in the second preclearing reaction were run in parallel. The gel was fixed with 10% acetic acid, treated with AMPLIFY™, a signal intensifying solution (Amersham), dried, and exposed. For experiments performed with the $^{125}$I labeled proteins, the treatment step with AMPLIFY™, a signal intensifying solution was omitted. Comparison of protein bands binding only to the pre-S fusion indicated the specificity of the interaction.

Infection of primary duck hepatocytes and polypeptide inhibition assay. Pre-S polypeptides expressed as GST fusion proteins were purified on glutathione sepharose beads and cleaved with thrombin. The beads which contained the GST moiety were removed and supernatant collected. Primary duck hepatocytes were preincubated with different concentrations of proteins at room temperature for 30 minutes.

DHBV positive duck serum ('viremic sera') was obtained from a Pekin duckling transfected with cloned DHBV DNA. Two weeks after transfection, when DHBV became strongly positive in the blood, the duckling was bled and blood stored at 4° C. overnight. The blood was centrifuged to obtain sera. Five μl of the resulting DHBV positive duck serum were added and incubation continued at 37° C. for three hours. The cells were extensively washed and incubated with fresh L-15 medium supplemented with a 1:200 dilution of rabbit anti-pre-S antiserum to prevent secondary infection. This antiserum was obtained by immunizing a rabbit with purified pre-S polypeptide (amino acids 1–161, expressed as GST fusion protein and cleaved to remove GST). Cells were harvested one-week postinfection and assayed for intracellular DHBV nucleic acid by Southern blot analysis.

Detection of p170 in different duck tissues. For these experiments, the elution profile of p170 through an anion exchange column was established. One ml of $^{35}$S-labeled duck hepatocyte lysates was dialyzed overnight in 50 mM Tris-HCl, pH 8.3. The lysates were applied to a column packed with preswollen DEAE-cellulose (Sigma) equilibrated with 50 mM Tris-HCl, pH 8.3. Bound proteins were sequentially eluted with 100, 200, and 400 mM NaCl in 50 mM Tris-HCl, pH 8.3. The peak of radioactivity in each fraction was collected and dialyzed back against lysis buffer. After incubation with GST-pre-S fusion protein, bound proteins were revealed by 8% SDS-PAGE and fluorography. To study tissue distribution of p170, 0.6–1.2 g of frozen tissue was homogenized in 6–12 ml of lysis buffer and after overnight dialysis against 50 mM Tris-HCl, pH 8.3, insoluble materials were removed by centrifugation (10,000 g for 20 min. at 4° C.) followed by filtration through a 0.45 μm filter. The solution was passed through a column containing 8 g of preswollen DEAE-cellulose and eluted with 100 mM and 200 mM NaCl in 50 mM Tris-HCl, pH 8.3. The 200 mM NaCl eluent was dialyzed against the lysis buffer and precleared twice with 10–20 μl bed volume of Sepharose beads. The concentration of proteins in each sample was determined by the Biorad protein assay (Lowry et al., J. Biol. Chem. 193:265, 1951), and 7 mg protein from each sample was incubated with 4–8 μg of GST-pre-S fusion protein. After separation of bound proteins with a 8% SDS-PAGE, protein bands were visualized by silver staining, using a Gelgold staining kit (Pierce).

Protein microsequencing of p170. p170 was purified from 40 g of duck liver using the method described above, separated from GST-pre-S protein by SDS-PAGE, and transferred to polyvinylidene difluoride membrane (PVDF) membranes (Biorad). After staining with ponceau S, strips of the membrane containing about 20 μg of p170 were obtained for sequencing analysis by digesting with lyase C, and separating high pressure liquid chromatography (HPLC). Selected peptide peaks were sequenced by the Edman degradation method.

Cloning of p170 cDNA. An intra-peptide "miniPCR" procedure was used to obtain portions of the coding sequences, designated peptide 1 and peptide 3. The degenerate nucleic acid sequences encoding peptides 1 and 3 were then used as unique PCR primers to amplify the coding region spanning these two peptides. The degenerate PCR primers were:

a) peptide 1 sense: 5'-GAXYTNTAYGTNATGGAGAT-3' (SEQ ID NO:6)

b) peptide 1 antisense: 5'-AAYTCNGGYTCNCCNGCYTCXTG-3' (SEQ ID NO:7)

c) peptide 3 sense: 5'-TZYTNAGYCAYGAXTTYCAXG-3' (SEQ ID NO:8)

d) peptide 3 antisense: 5'-TTZGCNGAXTANAXNGTYTC-3' (SEQ IN NO:9)

FIG. 15 shows amino acid residues 6–27 of peptide 1 (pk-81), and the entire 22 amino acids of peptide 3 (pk-69). Potential nucleotide sequences that code for peptides 1 and 3 are shown below each amino acid sequence. "Degenerate primer & product" identifies the primers used for intra-peptide miniPCR. "Specific primer & product" refers to specific amplification of 2.5 kb sequences between peptide 1 and 2 using a sense primer derived from peptide 1 and an antisense primer derived from peptide 3. Primers are shown in small letters, while amplified sequences are shown in capital letters. For convenience the antisense primers are written in the sense orientation.

The template was first strand cDNA transcribed from duck liver mRNA using random hexamer primers and superscript II reverse transcriptase (Gibco/BRL). Thirty-five cycles of amplification consisting of denaturing and annealing steps were carried out. The PCR products of expected sizes were isolated from a 4% NieSieve agarose gel, cloned, and sequenced.

Results

Figure 7A:
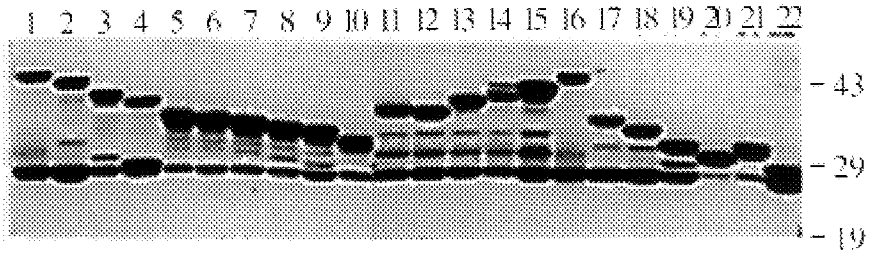
FIG. 7A is an autoradiographic image of an SDS-polyacrylamide gel showing the expression and purification of GST-pre-S deletion mutants. Molecular size markers are shown to the right.

A 170 kd cell surface glycoprotein binds to the pre-S domain of DHBV large envelope protein. The entire envelope protein of DHBV and the pre-S domain of HBV (the combined pre-S1 and pre-S2 domains) were cloned into the pGEX 2TK vector and expressed as GST fusion proteins. FIG. 1A shows the expression and purification of the GST fusion proteins in which GST is fused to: the DHBV pre-S/S protein (lane 1); the DHBV pre-S domain (lane 2); the HBV pre-S domain (lane 3); or the intact GST protein expressed from the pGEX 2TK expression vector (lane 4). In addition to a protein band of expected size, all the recombinant constructs displayed a band with a mobility slightly faster than the intact GST protein. The band was seen in all the additional fusion protein constructs (FIGS. 7A and 6B). It most likely corresponds to a proteolytic cleavage product of the fusion proteins around the cloning site.

Figure 1B:
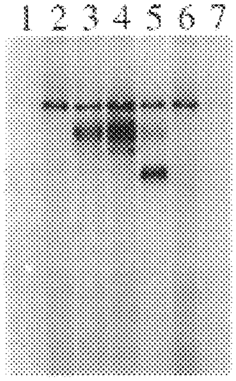
FIG. 1B is an autoradiographic image of a SDS-polyacrylamide gel showing proteins isolated from metabolically labeled lysates of primary duck hepatocytes using GST fusion proteins as probes.

Using the DHBV pre-S/S protein fused to GST as a probe, a 170 kd glycoprotein was identified in $^{35}S$ methionine labeled duck hepatocyte lysates that interacted with the DHBV pre-S domain (FIG. 1B, lane 3). In FIG. 1B, $^{35}S$ labeled primary duck hepatocyte lysates were precleared with Sepharose™ beads and GST-bound beads (lane 1), and then incubated with different GST fusion proteins immobilized on Sepharose™ beads. FIG. 1B shows the proteins isolated by binding to the following GST fusion protein: GST-DHBV pre-S/S protein (lane 3); GST-DHBV pre-S domain (lane 4), and GST-HBV pre-S domain (lane 2). The bound liver proteins were separated on SDS-PAGE and identified by fluorography. In a separate experiment, hepatocytes were metabolically labeled in the presence of tunicamycin. After preclearing (lane 7), the lysates were reacted with GST fusion proteins of the DHBV pre-S domain (lane 5) or the HBV pre-S domain (lane 6). Since the p170 protein was not retained by GST alone (lane 1), it appeared specific for DHBV sequences. The p170 protein was also retained by GST-pre-S fusion protein (lane 4), suggesting that the S domain was not essential for binding activity. Failure of a similar pre-S fusion protein derived from HBV to bind duck hepatocyte p170 (lane 2) as a control is consistent with a species specificity of the p170-pre-S interaction.

To determine whether p170 is glycosylated, duck hepatocytes were labeled in the presence of tunicamycin (2 μg/ml). Under these conditions, a protein of approximately 145 kd was detected (lane 5).

The p170 receptor is located on the cell surface of hepatocytes. To show this, cell surface proteins of primary duck hepatocytes were labeled with $^{125}I$ using the lactoperoxidase reaction technique. The $^{125}I$ surface labeled lysates were precleared (lane 6) and incubated with GST fusion proteins of the whole DHBV pre-S domain (lane 1) or of various deletion mutants of the DHBV pre-S domain fused to GST: GST-pre-S(25–102) (lane 2), GST-pre-S(80–104) (lane 3), GST-pre-S(80–102) (lane 4), or GST-pre-S (92–161) (lane 5).

Figure 1C:
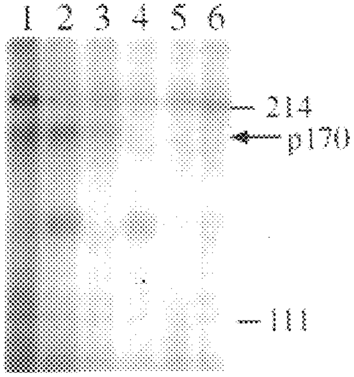
FIG. 1C is an autoradiographic image of a SDS-polyacrylamide gel showing the detection of p170 on the cell surface. For FIG. 1B and FIG. 1C, the positions of p170 and protein size markers are shown to the right.
Figure 2:
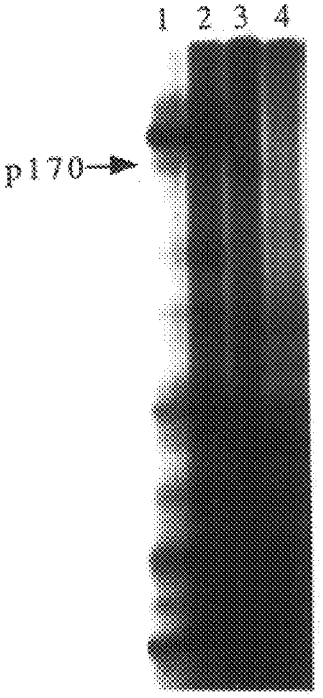
FIG. 2 is an autoradiographic image of cell surface proteins run on a SDS-polyacrylamide gel, comparing the specificity of labeling with lactoperoxidase versus the specificity of labeling with the iodogen method.

A control experiment was performed to show the specificity of cell surface labeling by lactoperoxidase. In FIG. 2, lanes 1 and 2 show cell surface proteins labeled with $^{125}I$ by lactoperoxidase. Lanes 3 and 4 show lysates of liver tissue labeled with $^{125}I$ by iodogen. After a brief preclearing, $^{125}I$ labeled lysates were incubated with GST fused DHBV pre-S domain (lanes 1 and 3) or a deletion mutant D80–102, which did not bind p170 (lanes 2 and 4). Note that proteins that were nonspecifically bound to Sepharose™ beads were different using the two labeling methods. Compared to direct $^{125}I$ labeling of unfractionated liver tissues by the iodogen method, cell surface labeling with lactoperoxidase produced a different pattern of nonspecific binding proteins (FIG. 2, compare lanes 1, 2 with 3, 4). A 170 kd molecule reacting specifically with GST-pre-S protein was nevertheless detected under both labeling conditions (FIG. 2, lanes 1 and 3; FIG. 1C, lane 1).

Reactivity of this molecule with several pre-S deletion mutants confirmed it to be the same p170 as detected in metabolically labeled lysates. Mutants pre-S(25–102) and pre-S(80–104), which bound to and retained p170 from $^{35}S$ labeled lysates (see below), also retained the 170 kd protein from surface labeled lysates (FIG. 1C, lanes 2 and 3). On the other hand, mutants 80–102 and 92–161, which failed to bind p170 in $^{35}S$ labeled lysates, were also unable to bind the 170 kd cell surface protein (lanes 4 and 5). Thus, p170 appears to be present on the cell surface of hepatocytes.

Figure 3A:
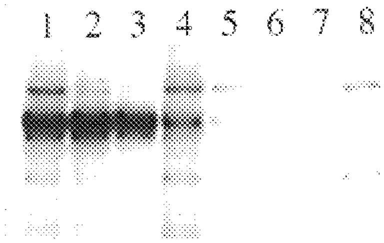
FIG. 3A is an autoradiographic image of an SDS-polyacrylamide gel showing competition of p170 binding by added DHBV particles.
Figure 3B:
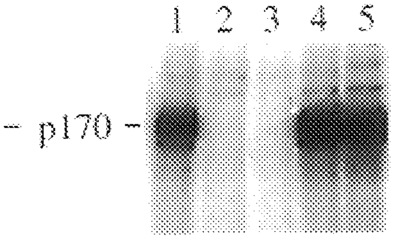
FIG. 3B is an autoradiographic image of an SDS-polyacrylamide gel showing reduced expression or inaccessibility of p170 in DHBV-infected hepatocytes.

Interaction of DHBV particles with p170 in vitro and in vivo. Since it was possible that the fusion proteins expressed in *E. coli* may not have had the same conformation as the corresponding native viral particles, it was important to determine whether p170 could bind to native viral particles. A competition experiment was performed between native DHBV particles and GST-pre-S/S fusion protein by adding highly viremic duck serum into the incubation reaction (FIG. 3A, FIG. 3B). Three ml of $^{35}S$ labeled lysates were precleared (lane 8). An equal volume of each lysate was incubated with 5 μg of GST-DHBV pre-S/S fusion protein in the absence of duck sera (lane 1), or in the presence of 60 μl (lane 2) or 200 μl (lane 3) of DHBV-free duck sera, or in the presence of 5 μl (lane 4), 20 μl (lane 5), 60 μl (lane 6), or 200 μl (lane 7) of DHBV viremic sera. Bound proteins were revealed by SDS-PAGE and fluorography. Incubation of $^{35}S$ labeled hepatocyte lysates with 5 μg of GST-pre-S/S fusion protein gave rise to a strong band of p170 (FIG. 3A, lane 1). Addition of 60 μl (lane 2) or 200 μl (lane 3) DHBV-free duck serum to the incubation mixture had little effect on binding to p170. In contrast, as little as 5 μl of DHBV positive serum strongly inhibited p170 binding (lane 4). Increasing the volumes of the DHBV positive sera diminished the p170 band in a dose-dependent manner (lanes 5, 6, and 7). With an incubation of 200 μl of viremic serum, virtually no p170 binding was observed (lane 7). A similar inhibitory effect was shown when DHBV particles purified through successive sucrose gradient centrifugation were applied. These results demonstrate that p170 is recognized by virion particles through the pre-S domain.

If DHBV particles bind p170 in vitro, they might also do so in vivo during natural "wild-type" viral infection. Three 100 mm dishes of primary duck hepatocytes were prepared from a DHBV-free duckling. One dish served as a control while the other two dishes were infected overnight with 30 μl and 300 μl of DHBV viremic serum, respectively. Nine days post-infections, cells were metabolically labeled and lysed. In FIG. 3B, precleared lysates were incubated with GST-pre-S fusion protein. Lane 1: noninfected cells; lane 2: cells infected with 30 μl viremic serum; lane 3: cells infected with 300 μl viremic serum. Lanes 4 and 5: comparison of p170 expression in duck hepatocytes (lane 4) and fibroblast-like cells derived from duck hepatocytes (lane 5). Hepatocytes were cultured in L-15 medium supplemented with 1% DMSO (lane 4) or 5% fetal calf serum (lane 5) for 10 days before labeling with $^{35}S$ methionine. Lysates, prepared from these hepatocytes were reacted with GST-pre-S fusion protein.

Although p170 was detected as a strong band in uninfected hepatocytes (FIG. 3B, lane 1), it was not detected in the two infected dishes (lanes 2, 3). Similar results were obtained with $^{125}I$-labeled cell surface protein lysates. Thus, either newly synthesized p170 was masked by binding to endogenous DHBV envelope protein or de novo synthesis of p170 was severely inhibited during infection.

Figure 4:
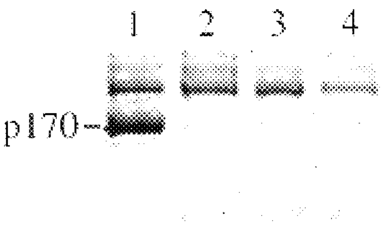
FIG. 4 is an autoradiographic image of an SDS-polyacrylamide gel showing a reduced level of p170 when detected by a GST-pre-S protein in DHBV-infected liver tissue.

To compare the steady-state levels of p170 between infected and noninfected duck livers, unlabeled liver tissues from two-week-old ducklings were studied. One duckling was DHBV-free, while the other was naturally infected. Liver tissues were homogenized in lysis buffer and precleared twice with empty Sepharose™ beads. After incubation with GST-pre-S fusion protein immobilized to Sepharose™ beads, bound proteins were visualized by SDS-PAGE and Coomassie blue staining of the gel. The results are shown in FIG. 4 (lane 1: 2 g of DHBV-free liver; lane 2: 2 g of infected liver; lane 3: 2 g of DHBV-free liver mixed with 1 ml of DHBV+serum from the infected duck; lane 4:

1 g of DHBV-free liver mixed with 1 g of infected liver). When the same amount of tissue was used, p170 was readily detected in uninfected liver but barely visible in infected liver (lanes 1 and 2). Adding either DHBV-positive duck serum or lysates of the infected liver masked p170 from DHBV-free duckling (lanes 3 and 4). Thus, p170, even if present at normal levels, would be rendered undetectable by a large number of virus particles.

Tissue distribution of p170. To examine whether expression of p170 is dependent on the differentiated status of duck hepatocytes, hepatocytes were cultured either in serum-free, DMSO-containing L-15 medium as described, or in L-15 medium supplemented with 5% calf serum instead of DMSO. Incubation in the L-15 medium causes rapid loss of both hepatocyte morphology and susceptibility to DHBV infection (Pugh et al., supra). After ten days of culture, hepatocytes maintained with calf serum became largely elongated so as to resemble fibroblasts. However, when cells were metabolically labeled and then cell lysates were incubated with pre-S fusion protein, the intensity of the p170 band was virtually unaffected (FIG. 3B, compare lanes 4 and 5). Thus, expression of p170 does not depend on differentiation of the hepatocyte.

Figure 5A:
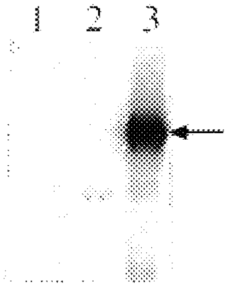
FIG. 5A is an autoradiographic image of an SDS-polyacrylamide gel showing the elution profile of p170 through a DEAE-cellulose column.

To study further the tissue specificity of p170 expression, a two-step purification procedure involving anion exchange column and affinity chromatography was developed. $^{35}S$ labeled hepatocyte lysates were run through a DEAE-cellulose column. The flowthrough fraction and eluent fractions (100 or 200 mM NaCl) (200 mM NaCl) were incubated with GST-pre-S fusion protein. Bound proteins were revealed by SDS-PAGE and fluorography. The results are shown in FIG. 5A (lane 1: flowthrough fraction; lane 2: 100 mM NaCl eluent; lane 3: 200 mM NaCl eluent). The position of p170 is shown by an arrow. These experiments showed that p170 was eluted with 200 mM NaCl from a DEAE-cellulose column (FIG. 5A, lane 3). This fractionation procedure removed the majority of nonspecific binding proteins.

Figure 5B:
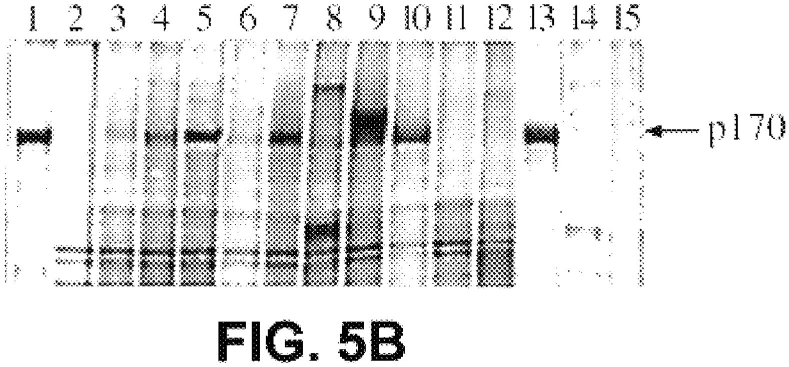
FIG. 5B is an autoradiographic image of an SDS-polyacrylamide gel showing the tissue distribution of p170 in various duck tissues.

To study the tissue distribution of the p170 protein, 0.6–1.2 g of either tissue lysates or serum derived from DHBV-free ducklings were passed through a DEAE-cellulose column. The 200 mM NaCl eluents were precleared with Sepharose™ beads. Seven mg of protein (7 mg for lysates and 70 mg for serum) were incubated with immobilized pre-S fusion protein. Bound proteins were separated by 8% SDS-PAGE and detected with a Gelgold™ silver staining kit (FIG. 5B). The lanes of FIG. 5B are: lane 1: 2 $\mu$g of the 170-kd molecular size marker $\alpha$2-macroglobulin; lane 2: GST-pre-S fusion protein (the same amount as used in purifying p170 from each tissue); lanes 3–13: purification and detection of p170 in heart (3), lung (4), liver (5), muscle (6), spleen (7), stomach (8), gall bladder (9), kidney (10), 7 mg serum protein (11), 70 mg serum protein (12), pancreas (13). Lanes 14 and 15 contain the second preclearing reaction for stomach (14) and gall bladder (15). Lanes 13–15 were derived from a separate SDS-PAGE and staining.

Figure 6:
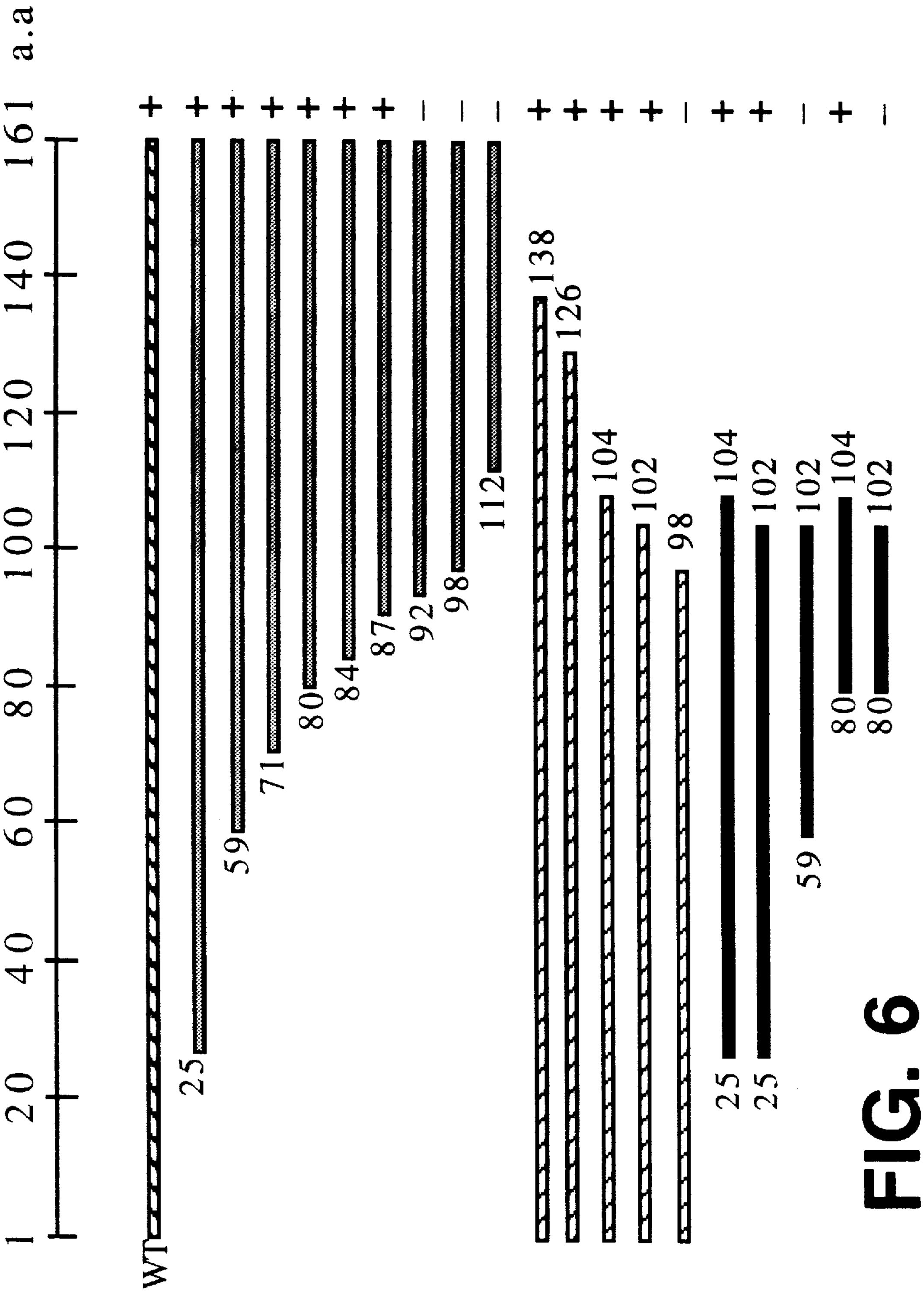
FIG. 6 is a schematic representation of pre-S deletion mutants and their binding results.

SDS-PAGE and silver staining revealed that p170 was highly expressed in pancreas, liver, kidney, and spleen (FIG. 5B, lanes 13, 5, 10, and 7, respectively). These are the same tissues in which DHBV replication has been reported. The p170 receptor was also found in lung, heart, and, to a less extent, in stomach and muscle tissue (lanes 4, 3, 8, and 6, respectively). In gall bladder, the major binding protein for the pre-S protein had a molecular size of around 180 kd, and was very abundant (lane 9). This 180 kd band was not seen in the preclearing reaction (lane 15). The p170 receptor was not detected in serum (lane 11), even when a 10-fold excess concentration of proteins was applied to the gel lane (lane 12). Thus, p170 does not appear to be a secreted protein.

p170 binds to a major neutralizing epitope of the DHBV pre-S domain. In order to define the region of the pre-S protein that is essential for binding to p170, nine progressive aminoterminal and five carboxylterminal deletion mutants were made and expressed as GST fusion proteins (FIG. 6). FIG. 6 shows the 161 amino acid residues of DHBV pre-S domain. Positions are given for the first amino acid residues in the aminoterminal deletion mutants, the last residues in the carboxylterminal deletion mutants, and both terminal residues in the double deletion mutants. Positive (+) or negative (−) binding results with p170 are shown to the right of each mutant. For both FIG. 7A and FIG. 7B, lanes 1 through 21 correspond to the intact pre-S domain (1), or to the deletion mutants 25–161 (2), 59–161 (3), 71–161 (4), 80–161 (5), 84–161 (6), 87–161 (7), 92–161 (8), 98–161 (9), 112–161 (10), 1–98 (11), 1–102 (12), 1–104 (13), 1–126 (14), 1–138 (15), intact pre-S (16), 25–104 (17), 25–102 (18), 59–102 (19), 80–102 (20), and 80–104 (21). Lane 22 in FIG. 4B shows the intact GST protein.

Figure 7B:
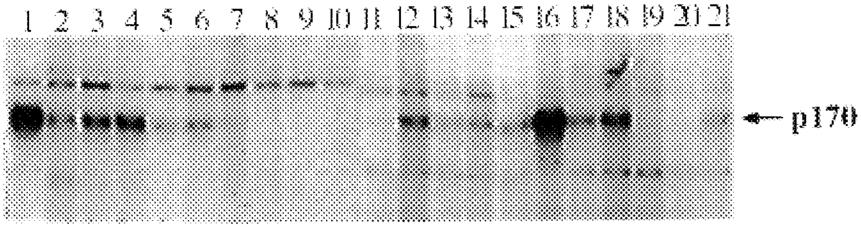
FIG. 7B is an autoradiographic image of an SDS-polyacrylamide gel showing the binding of p170 to GST-pre-S deletion mutants.

All of the fourteen deletion mutants expressed GST fusion proteins of the expected sizes as judged by SDS-PAGE (FIG. 7A). Removal of up to 86 amino acid residues in the aminoterminus reduced, but did not abolish, binding (mutant 87–161; FIG. 7B, lane 7). Deleting five additional amino acid residues abolished binding (92–161; lane 8). A mutant with a carboxylterminal deletion of up to 59 residues retained strong binding capacity (1–102; lane 12), while further deletion to amino acid 98 abolished binding (1–98; lane 11). Therefore, the pre-S sequence critical for p170 binding was localized to the 16 amino acid sequence between residues 87 and 102.

Figure 8:
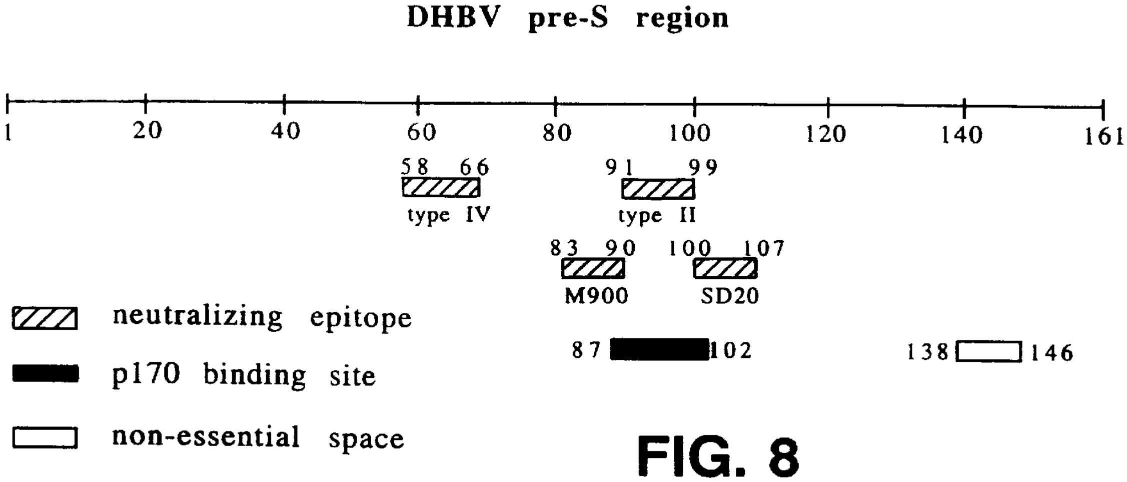
FIG. 8 is a schematic illustration that the p170 binding site coincides with a neutralizing epitope of the pre-S domain.

This sequence covers a known virus-neutralizing epitope (type II) that maps to amino acids 91–99 (Yuasa et al., *Virology* 181:14–21, 1991) and overlaps with two additional neutralizing epitopes located at amino acids 83–90, and 100–107, respectively (FIG. 8). The locations of type II and IV epitopes indicated in FIG. 8 are according to Yuasa et al, supra; the location M-900 and SD20 epitopes are according to Chassot et al., supra. The location of a sequence nonessential for viral infectivity is according to Li et al., supra.)

To test whether the minimum binding sequence functions independently of other pre-S amino acid regions, five double deletion mutants were constructed (FIG. 6 and FIG. 7A). Of the three double deletion mutants terminating at amino acid 102, only the one with a limited (24 amino acid) aminoterminal deletion bound p170 (25–102; FIG. 7B, lane 18). On the other hand, both mutants terminating at amino acid 104 were able to bind p170 (lanes 17 and 21). The shortest double deletion mutant capable of binding p170 was the construct 80–104, which contained only a 25 amino acid sequence (lane 21).

Figure 9:
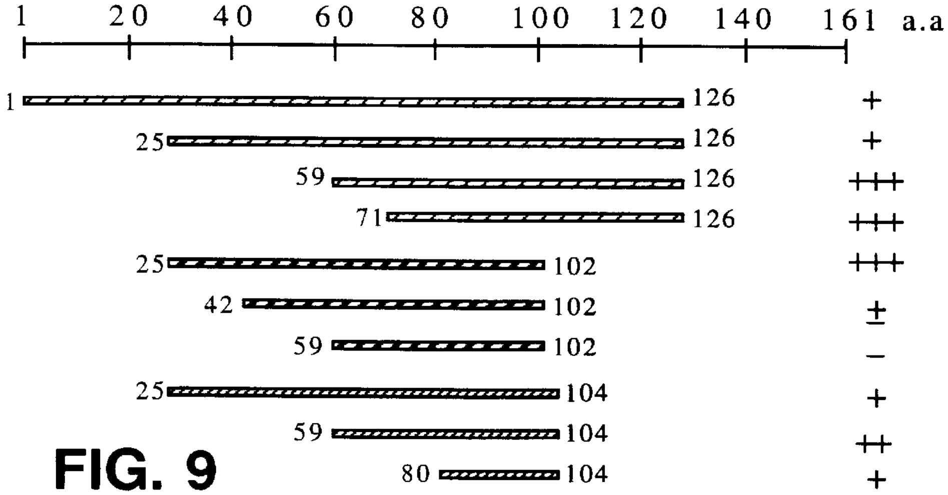
FIG. 9 is a schematic illustration showing which residues of the pre-S domain are required for p170 binding.

To further test the role of the pre-S amino acid sequence around the type IV epitope in the p170 interaction, five additional double deletion mutants were constructed: pre-S (25–126), pre-S(59–126), pre-S(71–126), pre-S(42–102), and pre-S(59–104) (FIG. 9). FIG. 6B is an autoradiograph showing the retention of p170 by different mutants (lane 1: preclearing reaction; Lanes 2–5: mutants terminating at residue 126; lane 2: 1–126; lane 3: 25–126; lane 4: 59–126; lane 5: 71–126; Lanes 6–8: mutants terminating at residue 102: lane 6: 25–102; lane 7: 42–102; lane 8: 59–102. Lanes 9–11: mutants terminating at residue 104; lane 9: 25–104; lane 10: 59–104; and lane 11: 80–104).

Figure 10:
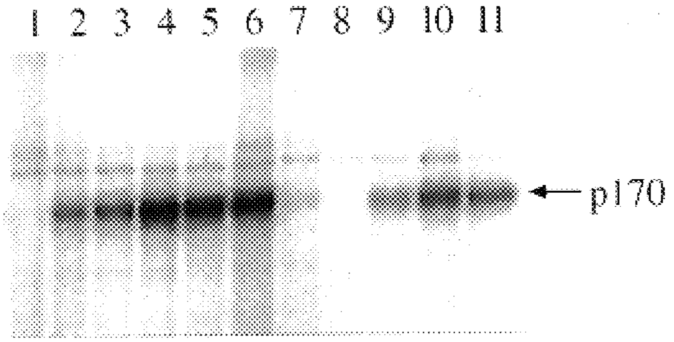
FIG. 10 is an autoradiographic image of a SDS-polyacrylamide gel showing the retention of p170 by different mutants.

Of the four mutants sharing an identical carboxylterminus at residue 126, but differing in their aminotermini (residues 1, 25, 59, and 71, respectively), p170 retention was not reduced, but rather increased, by successive aminoterminal truncations (FIG. 10, lanes 2–5). For the three double deletion mutants terminating at amino acid 104, moving the amino terminal end from amino acids 25 to 59 to 80 likewise did not reduce p170 binding (lanes 9, 10, and 11). Only for the mutants with a carboxylterminus at amino acid 102 did a change in the N-terminus from amino acid 25 to amino acid 42 greatly reduce p170 binding (lanes 6 and 7). Moving the aminoterminus further down to amino acid 59 completely abolished binding (lane 8), as shown in FIGS. 6, 7A, and 7B.

The p170 binding site in the human HBV pre-S protein. FIG. 20 shows the correspondence between the p170 binding site in the DHBV pre-S protein and a predicted p170 binding site in the human HBV pre-S protein. When pre-S residues 71–118 of HBV were aligned against residues 69–116 of DHBV, there were numerous identical residues (shown by asterisks) and no gaps in the sequence alignment. Thus, the p170 binding site at residues 87–102 of DHBV corresponds to a predicted p170 binding site at residues 89–104 of HBV. The arginine residue at position 97 of DHBV, which is critical for p170 binding, is conserved in HBV at HBV pre-S residue 99.

Figure 11:
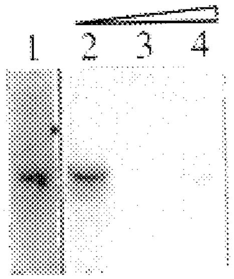
FIG. 11 is an autoradiographic image of a SDS-polyacrylamide gel showing inhibition of DHEV infection by a pre-S polypeptide containing a p170 binding site.

A pre-S polypeptide covering the p170 binding site inhibits DHBV infectivity. The coincidence of the location of the p170 binding site with the major pre-S neutralizing epitopes raises the possibility that p170 is the primary DHBV receptor required for viral entry into hepatocytes. However, the affect of neutralizing antibodies could be caused by steric hindrance or conformational change instead of by direct attachment to the receptor binding site. To directly test the importance of p170 binding by the pre-S domain on viral infectivity, an infection inhibition experiment was performed. The pre-S polypeptides were expressed as GST fusion proteins as described above, and the GST domain was removed by thrombin cleavage. Primary duck hepatocytes were preincubated at room temperature for 30 minutes with three different concentrations of pre-S polypeptides pre-S (59–104) or pre-S(59–102), which when expressed as GST fusion proteins are capable of binding the p170 receptor. Cells were then infected at 37° C. for 3 hours with 2 $\mu$l of viremic duck serum. Unattached virions were washed away and any secondary round of viral infection was prevented by the constant presence of rabbit anti-pre-S neutralizing serum. Viral DNA in hepatocytes was analyzed by Southern blot one week post-infection. The results are shown in FIG. 11 (Lane 1: Control hepatocytes infected in the absence of pre-S polypeptide; lanes 2–4: peptide 59–104 at 10 $\mu$g/ml (1), 100 $\mu$g/ml (2), and 1 mg/ml (3)). Peptide pre-S(59–104), whose GST-fusion protein binds p170, inhibited DHBV infection at 100 $\mu$g/ml and 1 mg/ml concentrations. These results demonstrate that the p170 binding site is a viral receptor binding site.

Effect of single amino acid changes in the major pre-S neutralizing epitope region on p170 binding. In order to define the individual amino acid residues critical for p170 binding, site-directed mutagenesis experiments were carried out on amino acids 88 through 102 of the pre-S domain. Eleven single amino acid substitution mutants involving nine amino acid residues were constructed. FIG. 12 shows the nature and location of amino acid changes in these mutants. Amino acid sequences from position 87 through 102 are shown for wild-type DHBV. Underlines denote amino acid residues that are variable in a goose hepatitis B virus strain (Shi et al., GenBank accession number M95589). Bold-face letters denote residues conserved in a comparison with heron hepatitis B virus (Sprengel et al., *J. Virol.* 62:3832–3839, 1988).

Figure 13A:
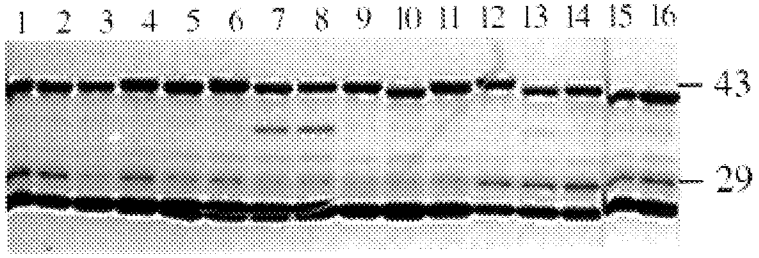
FIG. 13A is an autoradiographic image of a SDS-polyacrylamide gel showing expression of GST-pre-S fusion proteins from pre-S mutant constructs.
Figure 13B:
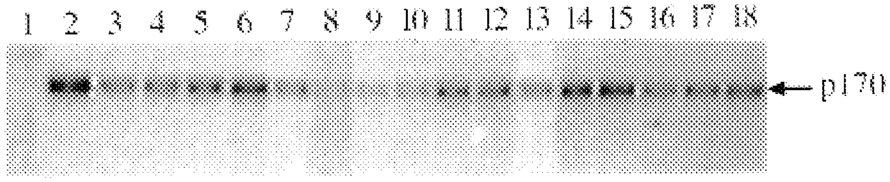
FIG. 13B is an autoradiographic image of SDS-polyacrylamide gel showing the binding capacity of pre-S mutants for p170.
Figure 17:
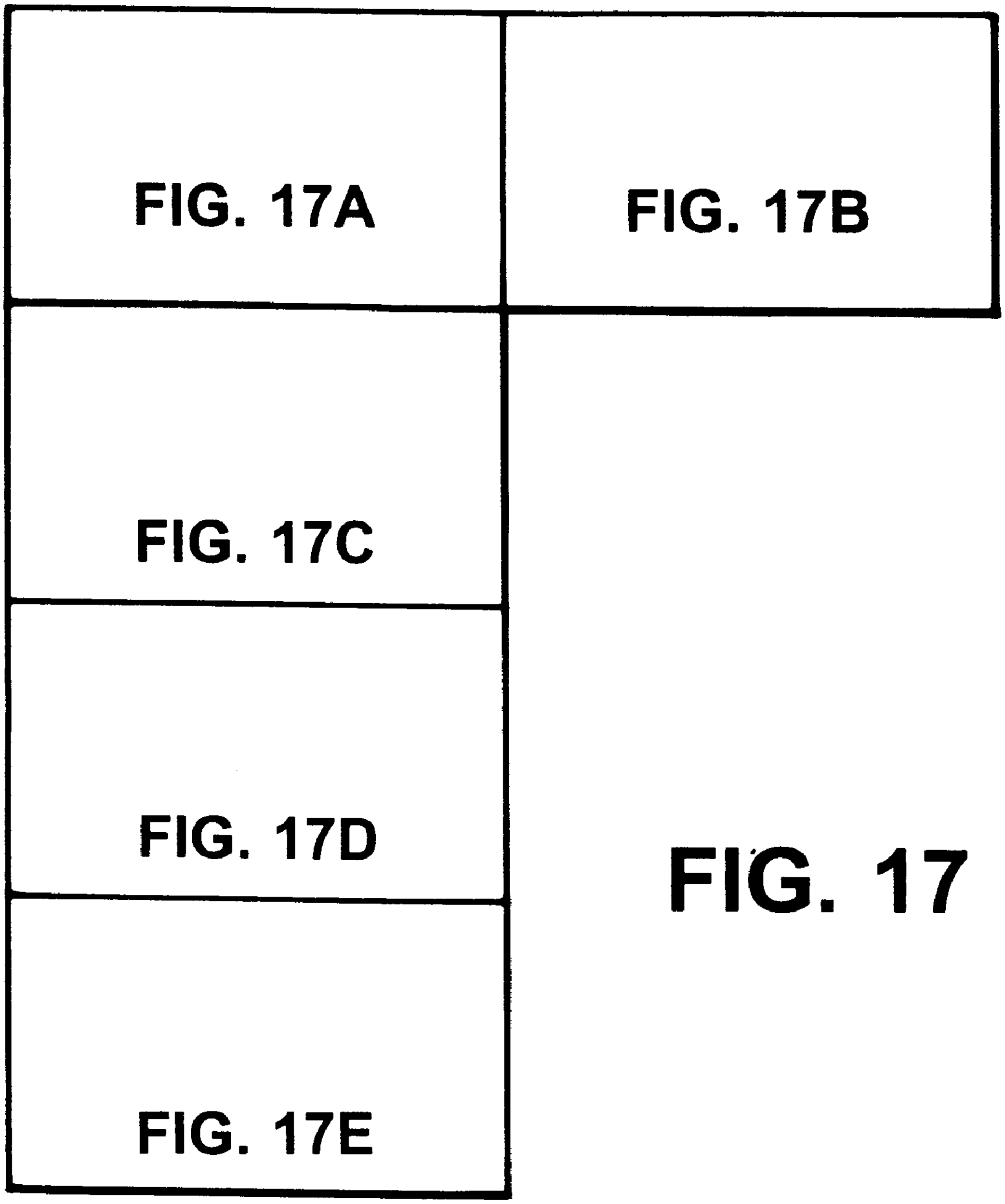
FIGS. 17A–E is an illustration of the nucleic acid sequence of the HBV pre-S gene and the corresponding translated amino acid sequence (SEQ ID NO:35–62).
Figure 17B:
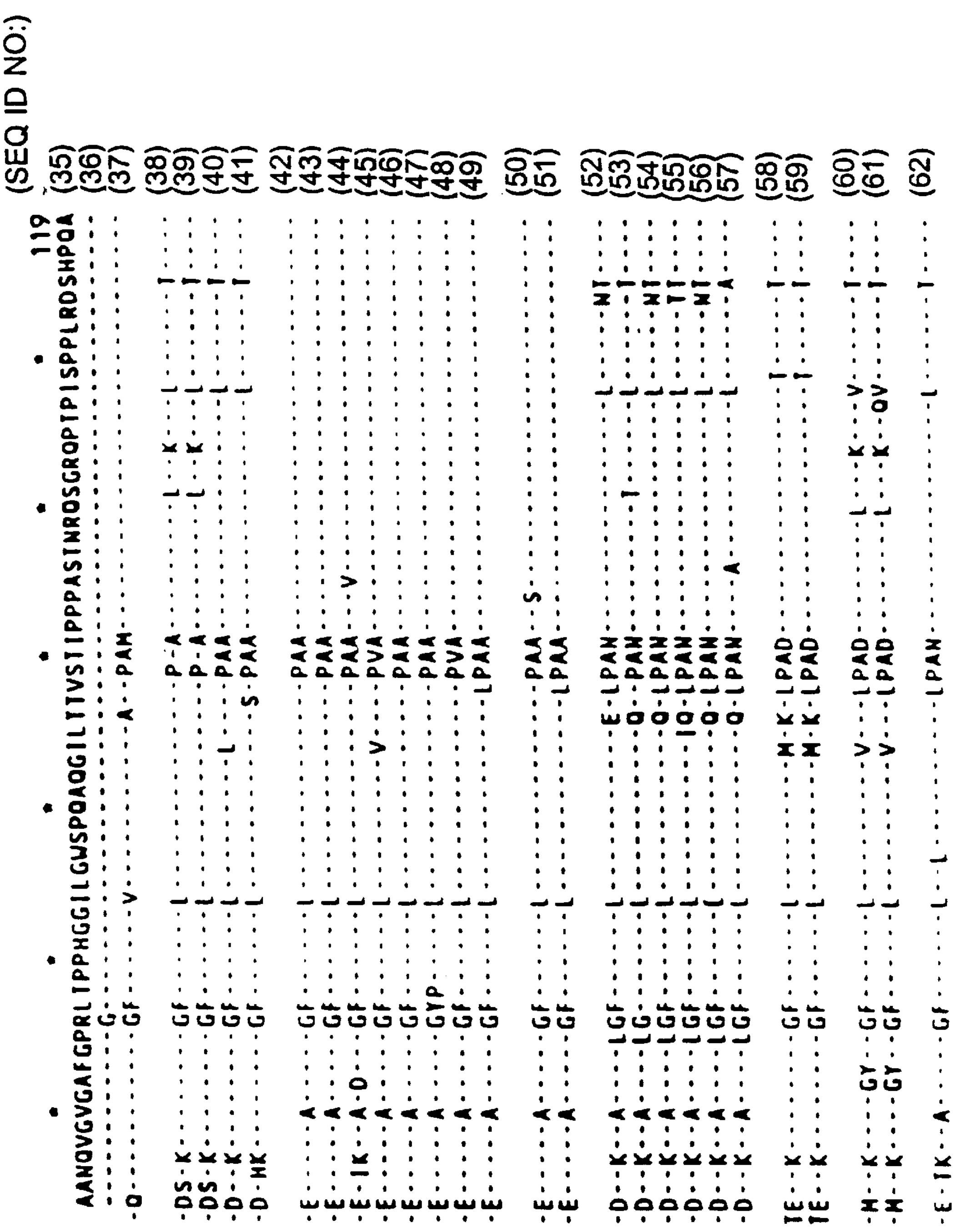
Figure 17D:
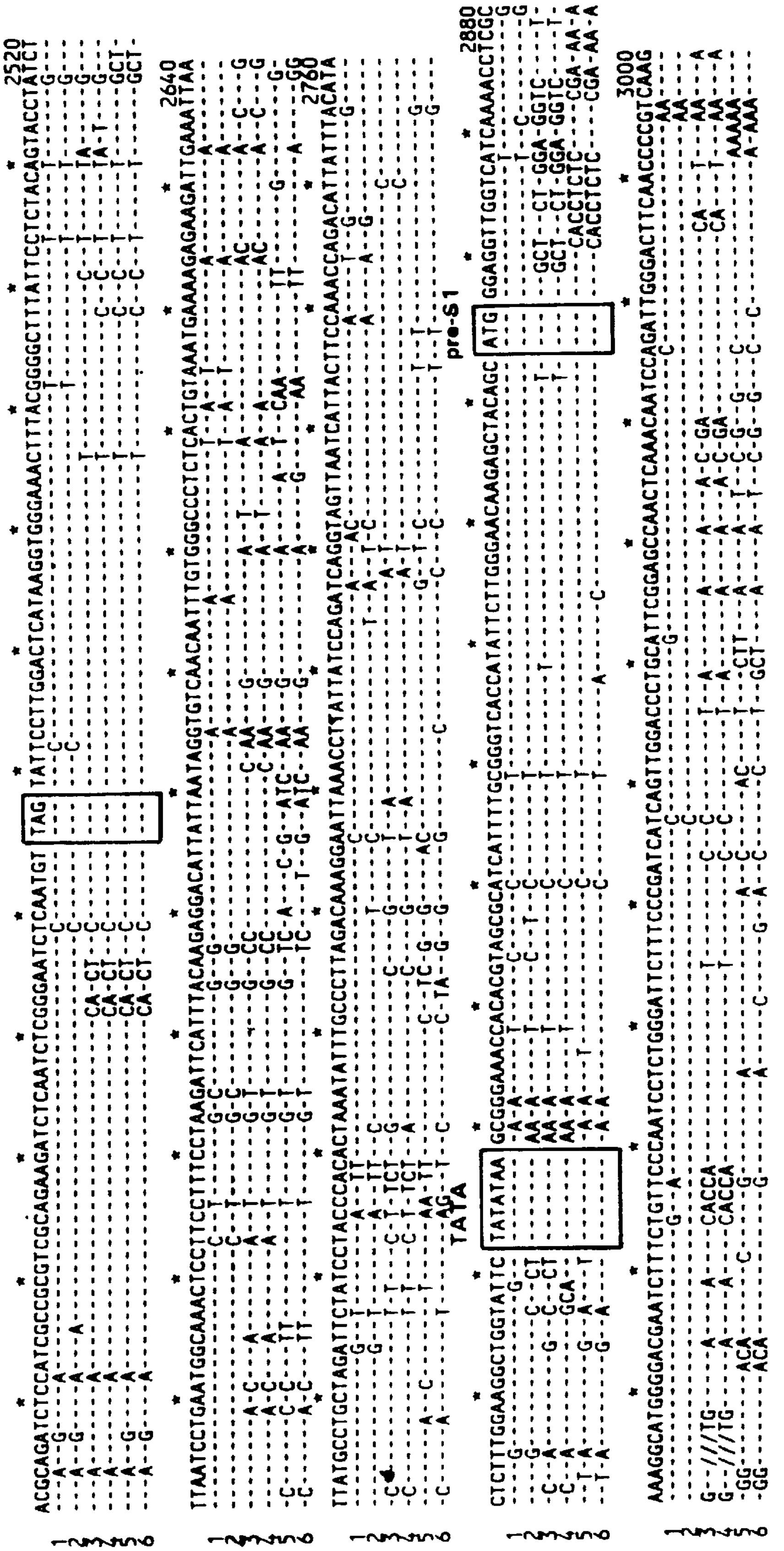
Figure 17E:
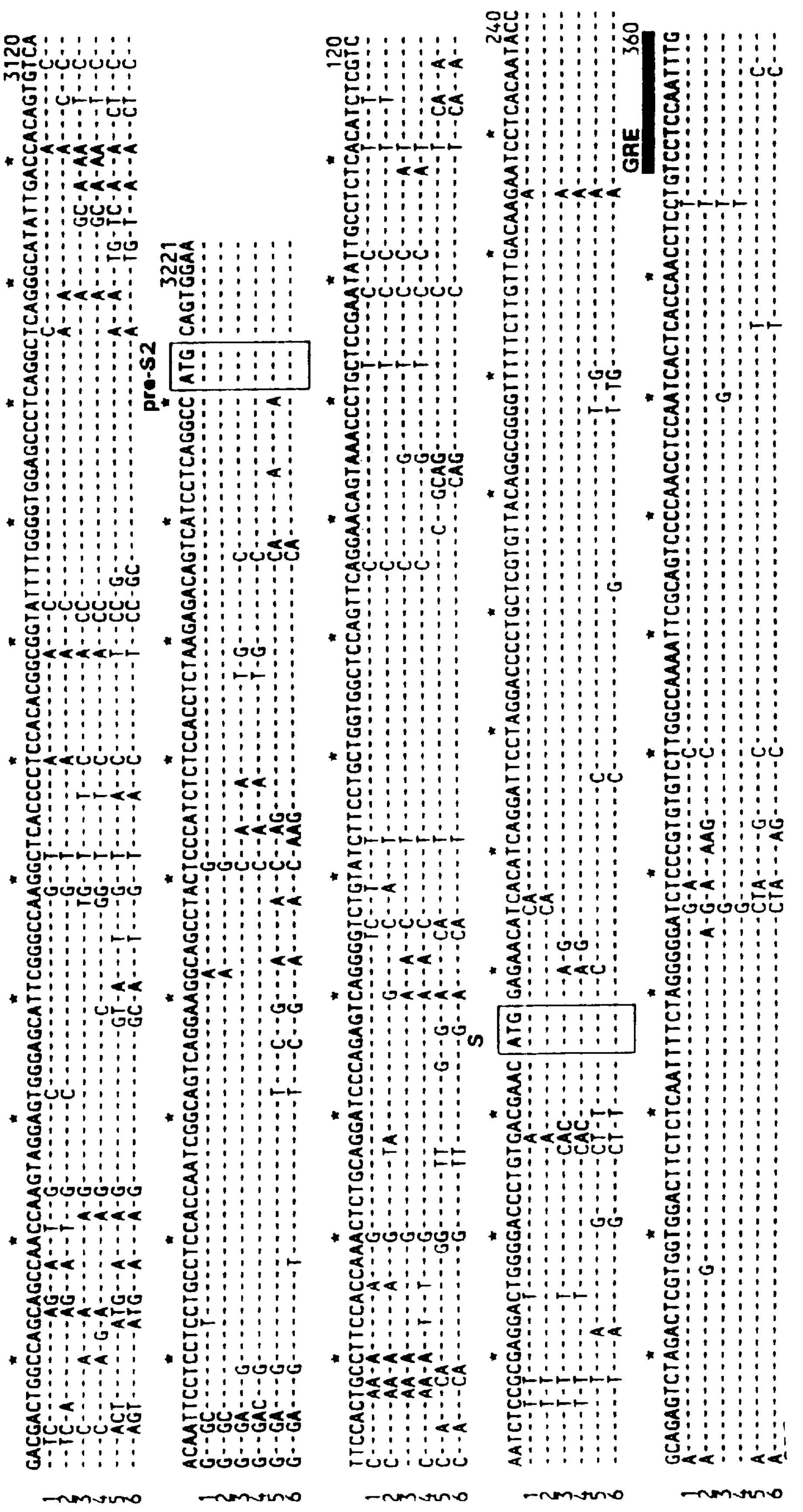
Figure 21A:
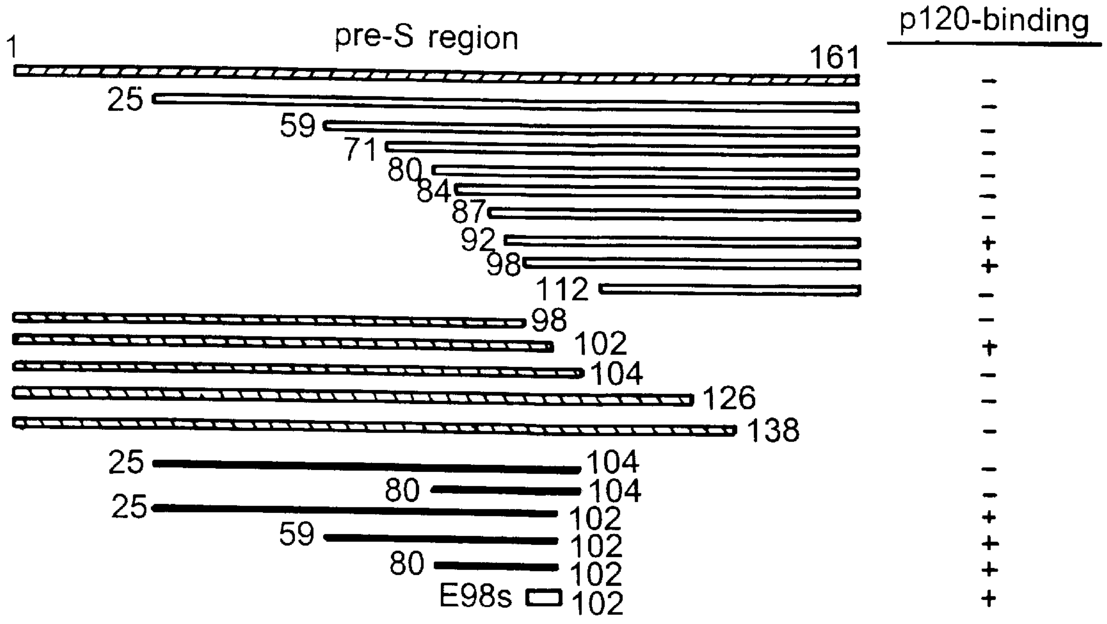
FIGS. 21A and B is a pair of panels illustrating the recognition of a 120-kDa duck hepatocyte protein by several truncated forms of DHBV pre-S protein. The pre-S part of DHBV large envelope protein and its truncated forms (N-, C-, double-deletions) were expressed as GST fusion proteins and purified on glutathione-Sepharose beads. They were incubated at 40C. with 35S labeled primary duck hepatocyte lysates which had been precleared with Sepharose beads. After extensive washing with the lysis buffer, bound proteins were fractionated by reducing SDS-8% PAGE gel. 35S labeled proteins were revealed by fluorography. A) Schematic representation of the pre-S constructs and their affinities for p120. B) Fluorograph. Molecular markers are shown at left and positions of p170 and p120 indicated.
Figure 22:
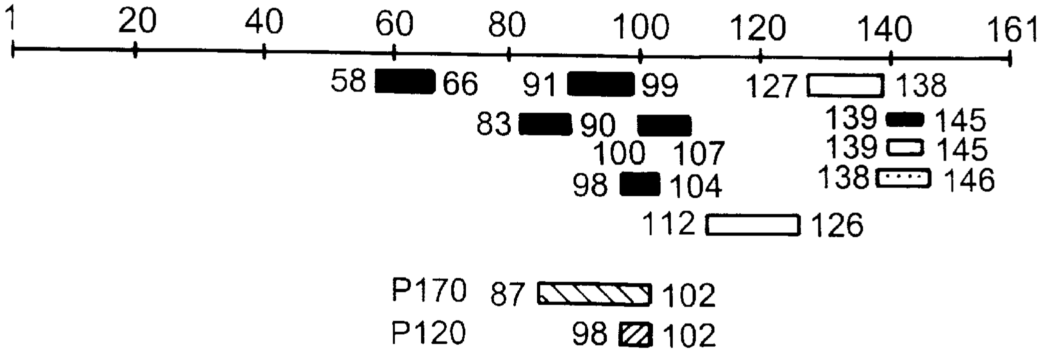
FIG. 22 is a schematic diagram illustrating co-localization of p120/p170 binding sites and clustered neutralizing epitopes. The pre-S region is schematically shown at the top (a.a. 1–161). p170/p120 binding sites and the epitopes recognized by neutralizing (black bar) and non-neutralizing (white bar) mAbs are indicated. The epitopes 58–66, 91–99, 127–138, 139–145 are according to Yuasa et al. (1991) Virology 181: 14–21, 83–90, and 100–107 according to Chassot et al. infra. A nonessential region for viral infectivity is shown as a dotted bar.
Figure 21B:
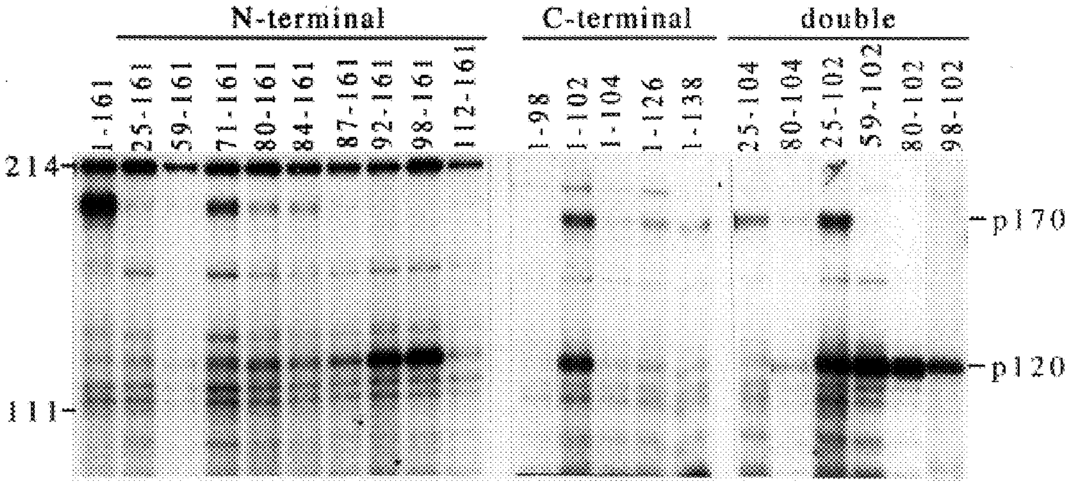

The affinity of the pre-S mutants for p170 binding was compared with that of the "wild-type" fusion protein (FIG. 12 and FIGS. 13A and 13B). FIG. 13A shows the level of expression of GST-pre-S fusion proteins from the mutants. Proteins purified from equal amounts of bacterial culture were applied to 12k SDS-PAGE. Mutants were arranged in the following order: E91G (lane 1), E92V (2), D93F (3), K95S (4), R97L (5), R97C (6), E98A (7), E98V (8), W88S (9), P9OL (10), R102G (11), K95S/R97C (12), K95S/R97L/E98A (13), K95S/A96T (14), E91G/K95S (15), E91G/R97C (16). Protein size markers are shown to the right of the figure. The levels of pre-S fusion proteins produced by the mutant constructs were similar (FIG. 13A) and equal amounts of the fusion proteins were used for binding experiments.

FIG. 13B shows the binding capacities of each pre-S substitution mutant for p170. Lanes 1 through 18 are: second preclearing (1), wild-type pre-S fusion protein (2), W88S (3), P9OL (4), E91G (5), E92V (6), D93F (7), K95S (8), R97L (9), R97C (10), E98A (11), E98V (12), R102G (13), E91G/K95S (14), E91G/R97C (15), K95S/A96T (16), K95S/Rp7L/E98A (18) While all of the mutants exhibited reduced retention of p170, mutants R97L and R97C consistently showed the lowest binding activity in several independent experiments. Mutant K95S also had greatly reduced binding capacity (lane 8). These results show that these two basic amino acid residues are important in the interaction of the pre-S domain with p170. However, when different amino acid substitutions were combined to produce double or triple amino acid changes (FIG. 12 and FIG. 13A), none showed a further decrease in p170 binding, even for double mutations at both residues 95 and 97 (K95S/R97C and K95S/R97L/E98A; FIG. 13B, lanes 17, 18).

p170 is structurally related to carboxypeptidases. To gain insight into the molecular identity of p170 and to provide essential peptide sequence for cloning the p170 cDNA, p170 receptor was purified from DHBV-free duck liver using a combination of ion-exchange chromatography and affinity chromatography. Purified proteins were separated by SDS-PAGE and transferred to PVDF membranes. The 170 kd protein band was digested with lyase C, and selected peptides were sequenced. Four examples of p170 peptide sequences are shown in FIG. 14A. A search of a computerized data base for peptides 3 and 4 did not reveal any significant degree of similarity to any known protein. However, peptides 1 and 2 are similar to mammalian carboxypeptidases H, N, and M, the strongest binding being to carboxypeptidase H. FIG. 14B shows the similarity of peptide 1 to basic carboxypeptidases. FIG. 14C shows the similarity of peptide 2 to basic carboxypeptidases. The dots denote residues identical to the peptide sequence. The acronyms shown in FIGS. 14B and 14C are: CPH (carboxypeptidase H); CPM (carboxypeptidase M); CPN (carboxypeptidase N); and AEBP1 (a mouse transcriptional repressor with carboxypeptidase activity). The nucleotide and amino acid sequence of each carboxypeptidase is known: bovine CPH (Fricker et al., *Nature,* 323:461–64, 1986); human CPH (Manser et al., 267:517–525, 1990); human CPM (Tan et al., *M. J. Biol. Chem.* 264:13165–13170, 1989); human CPN (Gebhard et al., *Eur. J. Biochem.,* 178:603–07); and AEBP1 gene (GenBank accession number X80478).

Cloning of p170 cDNA. Degenerate PCR primers were synthesized to amplify the middle portion of coding sequences for peptides 1 and 3, respectively (see Materials and Methods).

Sequencing of the PCR products unveiled the coding sequences for residues 12–18 of peptide 1 and residues 9–15 of peptide 3 (ATGAAACAGACACTGAAGAA) (SEQ ID NO:10) (FIG. 15). This information enabled synthesis of unique PCR primers to amplify the region between these two peptides. With a sense primer derived from peptide 1 (SEQ ID NO:11) (ATGGAGATCTCGGACGGCCC-3') and an antisense primer from peptide 3 (5'-TTCTTCAGTGTCTGTTTCAT-3') (SEQ ID NO:12), a 2.5 kb cDNA was amplified from randomly primed duck liver cDNAs. Sequencing the 5' end of PCR clones revealed nucleotides coding for residues 16–27 of peptide 1. Sequencing the 3' end identified coding sequence for residues 1–9 of peptide 3 (FIG. 15). These results are compatible with the 2.5 kb cDNA being part of the p170 cDNA.

FIGS. 18 and 19 show the partial nucleotide and deduced amino acid sequences of the 2.5 kb p170 cDNA. The sequence of FIG. 18 corresponds to 1.1 kb of nucleotide sequence at the 5' end of the 2.5 kb p170 cDNA. The peptide 1 amino acid sequence corresponds to amino acid residues 1–12 of the sequence of FIG. 18. The peptide 4 amino acid sequence corresponds to residues 337–349 of the sequence of FIG. 18. The presence of the peptide 4 coding sequence in the 2.5 p170 cDNA confirms it as the authentic cDNA for the p170 receptor. The sequence of FIG. 19 corresponds to 460 bp at the 3' end of the 2.5 kb p170 cDNA. The sequence of peptide 3 corresponds to the carboxylterminal 15 amino acid residues of the sequence of FIG. 19.

The 2.5 kb cDNA was blunt-ended and cloned into plasmid pUC18 cut with SmaI. The plasmid was transformed into *E.coli* strain DH5a. After overnight growth on LB plates supplemented with ampicillin, IPTG, and X-gal, several white colonies were isolated and grown in liquid LB medium supplemented with ampicillin. A positive clone harboring a plasmid containing a 2.5 kb insert was named Ep170pUC and deposited with the ATCC with designation No. 69869.

Pre-S Fusion Protein Constructs Leading to Identification of p120

As described above, to facilitate the identification of binding proteins for the DHBV pre-S molecule and mapping of the binding site, full-length and truncated forms of pre-S protein were expressed as fusion constructs with glutathione S transferase (GST) and immobilized on glutathione-Sepharose beads. Radiolabeled liver proteins which bound to the pre-S protein were retained on the beads and could be subsequently visualized by SDS-PAGE and fluorography. Some of the truncated pre-S constructs used to identify p120 are described in detail above in connection with p170. Additional deletional mutants were generated by twenty cycles of PCR amplification of a DHBV clone 16 and inserted into the BamHI-EcoRI sites of pGEX 2TK vector (Pharmacia). A stop codon was incorporated into each antisense primer to ensure a pre-determined C-terminus. Deletion mutants were named by positions of the first and last aa residues of the pre-S sequences.

To generate mutant E98S-102, plasmid DNA of mutant 25–102 cloned in 2TK was double digested with BamHI (cut at the 5' end of pre-S insert) and HindIII (cut at sequence coding for pre-S residue 98) to remove 0.2-kb coding sequence. After filling the cohesive ends with Klenow fragment and DNTP, the plasmid DNA was recircularized. To introduce single amino acid substitutions into residues 98–102 in the construct 80–102, specific mutagenic antisense primers were used in the PCR. Incorporation of point mutations into construct 92–161 required two steps. Mutation was first introduced into a 1.4-kb EcoRI-BamHI fragment of DHBV genome cloned into the pALTER-II mutagenesis vector (Promega). DNA fragments coding for residues 92–161 were then amplified by 20 cycles of PCR and cloned into pGEX-2TK vector.

Detection of pre-S Binding Proteins

Preparation of primary duck hepatocytes, metabolic labeling, and detection of pre-S binding proteins leading to identification of p120 were carried out as described above in connection with p170. To examine the availability of p120 on cell surface, plated hepatocytes on petri dishes were washed three times with PBS, incubated at room temperature (RT) for 30 minutes with 1 mM sulfo-LC-biotin (Pierce) in PBS, and washed again three times with PBS before lysis of cells. The precleared lysates were incubated with various constructs of pre-S fusion protein immobilized on Sepharose beads and retained materials were separated on SDS-PAGE. Proteins were transferred to nitrocellulose membrane and nonspecific binding sites blocked at RT for 1 hr with 5% BSA in PBS-0.05% Tween 20 (PBST).

After incubation at RT for 1 hr with a 1:2000 dilution of streptavidin conjugated with horse radish peroxidase (HRP; Pierce), biotinylated proteins were visualized by enhanced chemiluminesence (ECL). As a negative control, immunoprecipitation of a cytoplasmic protein (Golgi b-COP) was performed on both surface labeled hepatocyte lysate and labeled total liver proteins. For biotinylation of total liver proteins, 1 ml of liver tissue lysate (corresponding to 100 mg liver tissue) was incubated with 2.5 mg sulfo-LC-biotin for 1 hour at 40° C. The reaction was terminated by addition of glycine to 100 mM followed by further incubation for 3 hr. 6 mg of surface or total labeled liver proteins was incubated with 1:50 dilution of a monoclonal antibody against Golgi b-COP protein (M3A5, Sigma) for 2 hr at 4° C. After addition of 100 ml protein G-Sepharose beads (50% slurry), samples were incubated overnight. The retained proteins were analyzed as described above.

To study the tissue distribution of p120 by means of its affinity with truncated pre-S protein, 0.5 gm of frozen tissue was homogenized in 10 ml of lysis buffer, precleared twice with Sepharose-GST beads, and then incubated with 2 mg of immobilized GST fusion protein of pre-S construct 80–102. After separation of bound proteins with a SDS-6% PAGE minigel (BioRad), protein bands were visualized by staining with Coomassie blue. To detect small amount of p120 retained by the intact pre-S protein (1–161), bound proteins separated by SDS-8% PAGE were transferred to nitrocellulose filter. The blot was incubated successively with 1:1000 dilution of a rabbit polyclonal anti-p120 antiserum (16a) in PBST and 1:1000 dilution of a donkey anti-rabbit Ig conjugated with HRP, and positive bands revealed with Sigma Fast DAB (3,3'-Diaminobenzidine) tablets dissolved in water.

To detect p120 in duck tissues by direct Western blot, 50 mg of protein was separated by 6% SDS-PAGE and transferred to nitrocellulose filter. The filter was blocked with 3% BSA in PBST, and incubated with a 1:1000 dilution of a rabbit polyclonal anti-p120 antibody at RT overnight. After a thorough wash, the filter was incubated with 1:1000 dilution of a donkey anti-rabbit Ig conjugated with HRP, and positive bands revealed with Sigma Fast DAB.

Inhibition of DHBV Infectivity by Pre-S p120 Peptides

Primary duck hepatocytes were seeded at a density of 3x105 cells/well into 12-well plates. The experiments were performed within one week after plating. Pre-S polypeptides 80–102 and 80–104 expressed as GST fusion proteins were purified onto Sepharose beads. The GST portion was removed by digestion with thrombin (Sigma) and centrifugation. Thrombin (MW 55 kDa) was not removed in initial experiments but removed in repeat experiments through centricon 30 filter (cut-off 30 kDa), and similar results were obtained. Because of the nature of gene fusion with the 2TK vector, all the peptides contained at their N-terminus nine irrelevant aa residues (GSRRASVGS) (SEQ ID NO:13) contributed by thrombin recognition site, protein kinase domain, and BamHI site.

Hepatocytes in the plates were first incubated with the peptides at three different concentrations at RT for 1 hr, followed by addition of μl=|l viremic serum and a further incubation for 3 hrs. After extensive wash, cells were maintained in L15–1% DMSO medium supplemented with a neutralizing rabbit polyclonal anti-pre-S antiserum (16a) to suppress virus spread. Cells were harvested at day 8 post-infection. The experiments were performed in duplicate and harvested cells pooled for hybridization experiments.

Transfection and Infection With p120 Substitution Mutants pDHBV3.5 was constructed to contain a 3.5-kb over-length DHBV genome (NcoI-NsiI fragment of DHBV clone 16; reference 19) inserted between the EcoRI and PstI sites of pUC18 vector. This construct contained the coding sequence for viral pregenomic RNA and therefore produced infectious DHBV particles when transfected into LMH cells. Mutagenesis was performed on the 1.4-kb EcoRI-BamHI fragment of DHBV as described above and mutations were confirmed by DNA sequencing. The 0.8-kb BglII-XhoI fragment was excised from the mutagenesis vector to replace the corresponding fragment in the wild-type pDHBV3.5. Plasmid DNA used for transfection experiments were isolated from bacterial culture by the Promega Max-iprep columns and further purified by ultracentrifugation through CsCl gradient. DNA (20 mg) was transfected into a 100-mm dish of LMH cells by the calcium phosphate method. The cells were maintained in 1:1 ratio of DMEM/F12 medium supplemented with 10% fetal bovine serum. Each mutant construct was transfected in duplicate and materials pooled from the two dishes were used for hybridization. Cells were harvested at day 7 post-transfection and levels of DHBV ccc DNA, total and core RNA, and core DNA were detected by Northern and Southern blot analyses. Secreted core particles and virion particles were concentrated from culture medium by centrifugation through a 10–20% sucrose gradient or by precipitation with polyethyl glycine (PEG 8000, final concentration 10%). After successive digestion with DNase I, proteinase K followed by phenol/chloroform extraction, amounts of DHBV DNA was determined by Southern Blot. To selectively detect virion particles, the pelleted material was digested with Pronase and DNase I.

Virion particles concentrated from to 3 to 6 ml of culture medium were used to infect primary duck hepatocytes cultured in 6-well plates. After incubation at 37° C. for 6.5 hr, cells were washed and cultured for additional 7 days before extraction of total cellular DNA for Southern blot analysis.

Purification of p120 From Duck Liver

A total of forty grams of frozen liver from two-week-old Pekin ducklings were homogenized in 300 ml lysis buffer (50 mM Tris-HCl, pH 7.5, 150 mM NaCl, 1% Triton X-100, 1% sodium deoxycholate) using a Polytron homogenizer. The homogenate was clarified by low speed spinning followed by 10 min centrifugation at 14000 rpm in a Sorval SS34 rotor. The supernatant was filtered through 0.45 μm filter units and each 50 ml aliquot was precleared once with 80 μl (10% v/v) killed Staphylococci aureus positive for protein A (Boehringer Mannheim), and once with a mixture of 100 μl bed volume (b.v.) glutathione Sepharose beads and 5 ml b.v. Sepharose beads conjugated with GST protein, at 4° C. for 8 hr to overnight. Proteins bound to the Staphylococci or Sepharose beads were removed by low speed centrifugation, and the precleared lysate was incubated with DHBV pre-S peptide (amino acids 80–102) immobilized on Sepharose beads via the GST tag (40 μl b.v. beads, circa 80 μg fusion protein) at 4° C. overnight. After three times washing with the lysis buffer, the retained proteins were separated by 6% SDS-PAGE gel and blotted onto polyvinylidene difluoride (PVDF, Bio-Rad) membranes. Protein bands were revealed by staining with 0.1% Ponceau S and the 120-kDa band was cut out. An estimated 28 μg (equivalent to 20 pmol) of p120 protein was obtained from 40 gm duck liver.

Protein Microsecuencing of p120

The p120 blotted to PVDF membrane was sent to Harvard Microchemistry Facility for customerized protein microsequencing analysis. Briefly, p120 was digested with trypsin, and digested fragments were separated by high-pressure liquid chromatography (HPLC). Selected peptides were sequenced by the Edman degradation method.

Construction of Duck Liver cDNA Libraries

RNA was extracted from frozen Pekin duck liver with guanidinium thiocyanate (RNA isolation kit, Stratagene), and mRNA purified through an oligo dT column (Poly(A) Quik mRNA purification kit, Stratagene). Oligo dT primed and random primed lamda expression libraries were constructed using ZAP-cDNA synthesis kit and ZAP Express cDNA synthesis kit, respectively (Stratagene). For directional cloning, 1st strand cDNA synthesis was primed with oligo-dT (the primer also contains an XhoI site) using Moloney murine leukemia virus (M-MuLV) reverse transcriptase. After 2nd strand synthesis and addition of an EcoRI adaptor, the cDNAs were digested with XhoI and size-fractionated with Sephacryl S-400 column. Fractions 4 and 5 were combined and further electrophoresed in 1k agarose gel to isolate cDNAs greater than 1 kb in size. The purified cDNAs were ligated to EcoRI/XhoI double digested Lambda ZAP II vector. The ligation product was packaged into Gigapack II Gold packaging extract (Strategene), then plated in XL1-Blue MRF' host cells. The primary library was estimated to contain 6×106 independent recombinants and has an average insert size of 1.9 kb. This oligo dT primed library was amplified once and stored in aliquots at 4° C. (in chloroform) or −70° C. (in DMSO). For construction of random primed library, 1st strand cDNA systhesis was primed by random hexameric oligonucleotides. The cDNAs were ligated with EcoRI adaptor, size fractionated with Sephacryl S-400 column, and cloned into EcoRI degested ZAP express vector (Stratagene). This random primed library has $6\times10^6$ independent recombinants and an average insert size of 1.6 kb.

Cloning of p120 cDNA

Since amino acid sequences of all four p120 peptides perfectly matched chicken and human glycine decarboxylase gene, duck cDNA for p120 was isolated by a cDNA fragment of the chicken glycine decarboxylase. Chicken liver mRNA was reverse transcribed by random hexamers and superscript II reverse transcriptase (Gibco/BRL) at 42° C. The RNA template was removed by treatment with RNase H. The 1st strand cDNA was used as template for PCR amplification of the partial coding sequence for chicken glycine decarboxylase. The primers used were based on published sequence (Kume et al., 1991) and had the sequence

5'-ATCACTGAGCTCAAATTACCCCATGAGATG-3'

(SEQ ID NO:14) (sense primer, positions 679–701) and 5'-GGAAACTCGAGCTGGAAGCAGTGTTATGAA-3' (SEQ ID NO:15) (antisense primer, positions 3038–3009). After 35 cycles of amplification using Vent DNA polymerase the product (2.3 kb) was purified from the agarose gel and labeled with 32P-dCTP using random DNA labeling kit (Amersham). To screen for p120 cDNAs, oligo dT primed duck liver library was plated onto NZY plates at a density of $5\times10^4$ pfu/150 mm plate and cultured at 30° C. overnight. The plaques were transferred onto duplicate nitrocellulose filters. The filters were hybridized with the $^{32}P$ labeled chicken cDNA fragment, washed and exposed to X-ray films. The final wash consisted of 0.5×SSC/0.1% SDS at 50° C. For secondary screening, areas of NZY agar plates corresponding to positive hybridization signals were cut out and immersed in SM buffer to elute the phages. The phages were used to infect XL1 Blue MRF' cells and plated onto NZY plates at low density to prevent individual plaques from merging with each other. The duplicate filters were rescreened with the chicken cDNA probe and positive plaques identified and isolated.

p120 DNA Sequencing

After the secondary screening, the pBluescript SK plasmids containing the inserts were excised from the p120 positive Lambda phages using a protocol provided by the manufacturer. DNA sequences at the ends of the inserts were determined with the aid of sequencing primers annealing to the 5' end (T3 transcription primer) or 3' end (pUC/M13 −40 primer) of pBluscript vector. For systemic sequencing of the longest insert, deletional constructs were generated using exonuclease Bal 31. To generate clones with deletions at the 5' end, the recombinant plasmid was linearized with BamHI, and treated with Bal 31. Aliquots were taken out at different time points after digestion and exonuclease activity terminated by phenol/chloroform extraction. DNA in each aliquot was digested with KpnI and cloned into KpnI/Hind II digested M13mp18. For deletions at 3' end of the insert, the recombinant plasmid was linearized with XhoI, and treated with Bal 31. DNA aliquots at different time points of exonuclease digestion were further digested with BamHI and cloned into BamHI/HincII digested M13mp18 DNA. Recombinant M13 phages were identified by DNA hybridization. Sequencing was performed on single stranded phage DNA using the universal pUC −40 sequencing primer. A few regions were not covered by the deletions and were sequenced using internal primers. Gel compressions were resolved by sequencing the opposite strand and by using dITP reagents.

Cell-Free Translation of p120 cDNA and Recapitulation of Pre-S Binding Capacity

The longest p120 cDNA clone, by analogy with chicken and human glycine decarboxylases, is expected to contain nearly complete coding sequence for the mature form of p120. For cell-free expression of p120 from this clone, an in-frame ATG codon surrounded by optimal Kozak sequence is attached to its 5' end via 20 cycles of PCR, using the sense primer 5'-atggtaccatgGAGGCGGCGCGGTGCATCGAGC-3' (SEQ ID NO:16) and antisense primer 5'-ATCTCGAGATATTAACATTAGCAATGTTACT-3' (SEQ ID NO:17) (small letters: nontemplated sequences; underlined: restriction sites; boldface: translational initiation codon). The PCR product was digested with KpnI and XhoI and cloned into the KpnI/XhoI sites of pBluscript vector. Coupled in vitro transcription/translation was carried out with T7 RNA polymerase, rabbit reticulocyte lysate and $^{35}S$ methionine using a kit purchased from Promega (TnT transcription/translation system). For pre-S binding assay, a fraction of translation product (5–10 $\mu$l) was incubated with 2–4 mg of various forms of DHBV pre-S protein expressed as GST fusion proteins and immobilized on Sepharose beads. The incubation was carried out in lysis buffer at 40° C. for a few hrs to overnight. After vigorous wash with lysis buffer, bound p120 was revealed by SDS-PAGE followed by fluorography.

High Affinity for Truncated Forms of Pre-S Protein p120 is not a glycosylated protein since labeling primary duck hepatocytes in the presence of tunicamycin (1 =|g/ml) did not modify the mobility of the binding protein. The three p120 binding constructs contained pre-S sequences 92–161, 98–161, and 1–102, respectively. These results suggest that p120 binding motif is normally hidden by the surrounding pre-S sequences but can be made accessible by substantial truncation at either N- or C-terminus. Further deletion removed p120 binding motif, abrogating p120 binding. Thus the sequence bracketed by residues 98 and 102 is the putative p120 binding motif. Consistent with this interpretation, p120 binding capacity was maintained in the three double deletion constructs with a fixed C-terminus at residue 102 but different N-termini at residues 25, 59, and 80. Construct 80–102, which retained only 23-aa residues of the pre-S region, bound p120 at least as efficiently as the longer construct 1–102. To test whether residues 98–102 can bind p120 in the absence of any surrounding DHBV sequence, mutant E98S-102 was constructed (residue 98 in this construct was converted from glutamic acid to serine due to the enzymatic manipulation). This construct, as predicted, was able to bind p120 efficiently.

The p120 binding site overlaps extensively with the binding site (residues 100–107) of a virus-neutralizing monoclonal antibody, SD20 (Chassot et al. (1993) Virology 192:217–223). This neutralizing epitope is one of the three clustered neutralizing epitopes.

We also isolated a monoclonal antibody which at a 1:200 dilution of the hybridoma culture supernatant inhibited DHBV infection in primary duck hepatocytes by more than 90%. With the use of GST tagged deletion mutants, the binding site of this neutralizing monoclonal was mapped to pre-S residues 98–104, which entirely covers the p120 binding site. Unlike p120, the monoclonal antibody requires pre-S residues 103 and 104 for binding.

Retention of Low Level p120 By Intact Pre-S Construct

The fact that intact pre-S protein failed to retain p120 raised the issue of the significance of p120-pre-S interaction. To test the possibility that intact pre-S protein can immobilize small amounts of p120, we used to a more sensitive detection method. Unlabeled liver proteins from 0.5 gm tissue were incubated with the GST fused intact pre-S protein (1–161) and bound p120 protein was identified by Western blot analysis with a rabbit polyclonal antiserum raised against gel-purified p120. With this improved sensitivity detection system, p120 was found in the retained material, though much less efficiently than retention by construct 80–102. p120 retention by the intact pre-S protein seems independent of p170, since it occurs in DHBV-infected liver in which p170 binding is sequestered by endogenous viral pre-S protein.

Efficient p120 Binding Requires Precise Truncation at the Pre-S C-Terminus

While all constructs terminating at residue 102 (1–102, 25–102, 59–102, 80–102) bound large amounts of p120, those ending at residue 104 (1–104, 25–104, 80–104) did not (FIG. 1). To further define the boundary between p120-binding and nonbinding C-terminal deletion constructs, three additional constructs with fixed N-terminus at residue 80 but different C-termini at residues 103, 101, and 100 were constructed. p120 did not bind the mutant truncated at aa 104, but could bind mutants terminating at either residue 103 or 102. Further truncation to residue 101 or 100 abrogated binding. Therefore, C-terminal truncation has to occur at residue 102 (with a C-terminus Phe-Arg-Arg) or 103 (with a C-terminus Arg-Arg-Gln) in order to gain affinity for p120.

p120 Binding Motif is Composed of a Tripeptide Sequence of Phe-Arg-Arg

To further elucidate the contribution of individual aa residues to p120 binding, site-directed mutagenesis was carried out for residues 97 through 102. Most mutants were generated in the 80–102 construct, because of its strong reactivity with p120 in wild-type sequence as well as for simplicity in the construction of mutations. The binding results of the pre-S mutants in the construct 80–102 are shown in the left panel of FIG. 23. Mutating glutamic acid at position 98 to valine maintained, and increased, binding. Changing alanine at position 99 to aspartic acid also retained reactivity towards p120 (A99D). This residue is not conserved in nature as it was found to be changed to tyrosine in a goose hepatitis B virus strain which can infect ducks (Shi et al., GenBank Accession No. M95589). As to the phenylalanine residue at position 100, substitution by either valine or leucine abolished binding (F100V, F100L), while mutation to another aromatic aa such as tryptophan was tolerated (F100W). For the penultimate arginine, mutation to neither leucine nor histidine was tolerated (R101L, R100H), but substitution by lysine (R101K) retained residual binding capacity. Most stringent for p120 binding was the terminal arginine residue, for which substitutions by glycine, histidine, and even by lysine, totally abolished p120 binding (R102G, R102H, R102K). Therefore, the triplex of Phe-Arg-Arg residues at positions 100–102 are critical for p120 binding and very likely constitute the p120 contact site. These three residues are conserved in all DHBV strains (and a goose hepatitis B virus strain) sequenced.

Figures 27A, 27B, 27C, 27D:
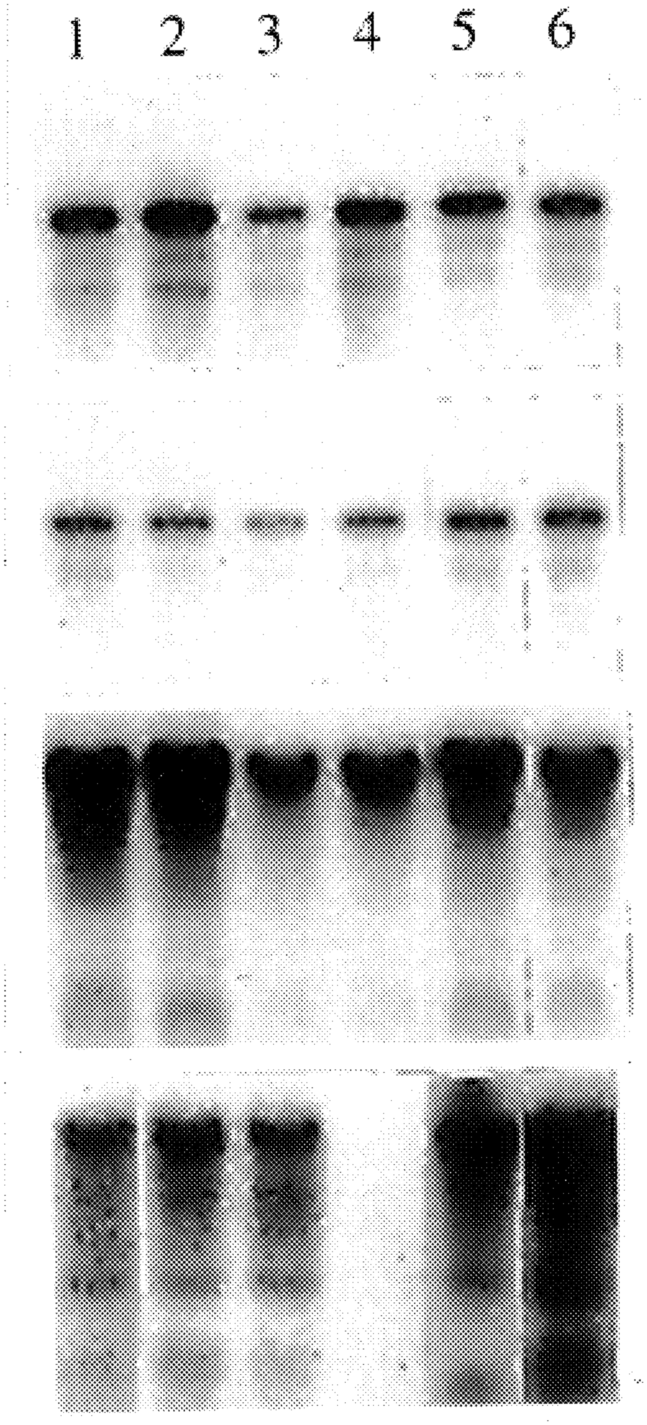
FIGS. 27A–D is a gel showing impairment of DHBV infectivity by mutations at p120 binding site. Various DHBV mutants in an overlength DHBV genome were transfected into LMH cells in duplicate. DHBV particles were concentrated from pooled medium and equal amounts of virion particles were used to infect primary duck hepatocyte cultures for 6.5 hrs. Cells were harvested at day 7 post-infection. A) Southern blot analysis of viral particles secreted to LMH culture medium at day 3 post-transfection. B) Southern blot analysis of another aliquot of day 3 viral particles pre-treated with Pronase and DNase I. C) DHBV DNA associated with intracellular core particles at day 7 post-transfection. D) Intracellular DHBV DNA in primary duck hepatocytes infected for 6.5 hr with virus particles produced in LMH cells. Lane 1: R101I/R102D; 2: R101L/R102L; 3: F100V/R101L; 4: Y103C/Q104F; 5: K95S/R97L/E98A; 6: wild-type.
Figure 28:
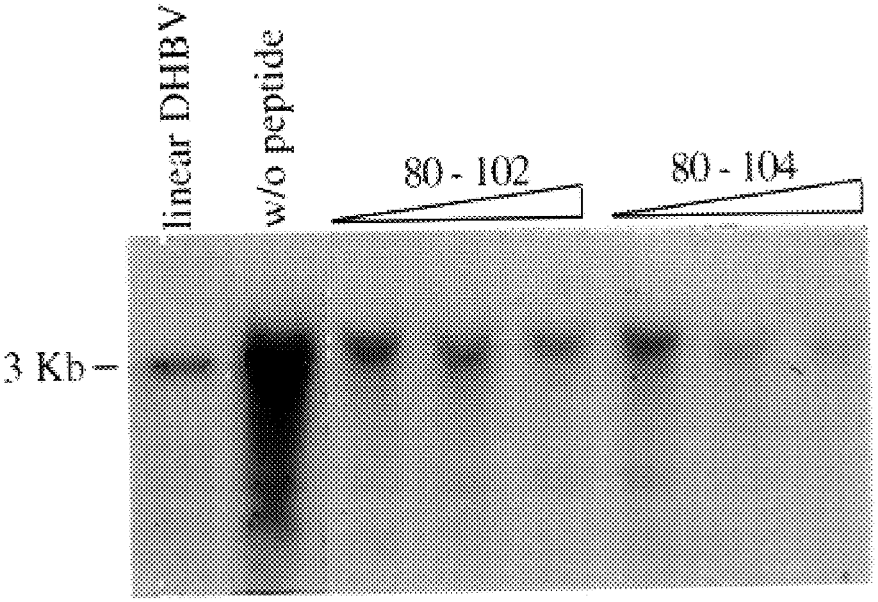
FIG. 28 is a Southern blot illustrating the inhibition of DHBV infection of primary duck hepatocytes by short pre-S peptides. The pre-S peptides 80–102 and 80–104 were mass produced as GST fusion proteins and removed from the GST partner by thrombin cleavage. They were incubated at RT for 1 hr with primary duck hepatocytes at three different concentrations: 10 $\mu$g/ml, 100 $\mu$g/ml, and 1 mg/ml. DHBV positive duck serum (1 $\mu$l) was then added and incubation continued for three additional hrs. Cells were harvested at day 8 post-infection and intracellular DHBV DNA studied by Southern blot analysis. w/o peptide: without peptide.

Residues 100–102 are positioned at the C-terminus in the construct 80–102. To rule out the possibility that the importance of these residues was merely a result of positional effect, three mutants of these residues, F100V, R101L, R102G, and three mutants of residues 97 and 98, R97C, E98A and E98V, were introduced into another p120 binding construct 92–161 and the affinity for p120 was tested. All the three mutants of residues 100–102 failed to retain p120 while mutants of residues 97 and 98 could bind to the protein (FIG. 27, right panel).

p120 is Detectable on the Hepatocyte Cell Surface

Figure 26:
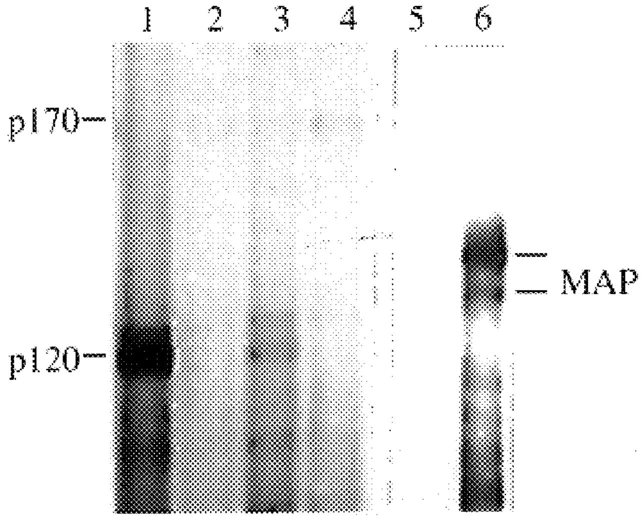
FIG. 26 is a gel showing detection of p120 in lysates of cell-surface biotinylated primary duck hepatocytes. Primary duck hepatocytes cultured for two days in Petri dishes were labeled with sulfo-LC-biotin. Cells were washed three times with PBS before and after labeling. The cell lysates were incubated with the following pre-S constructs: 80–102 (1); 80–104 (2); 25–102 (3); 1–161 (4). Positions of p120 and p170 are indicated. As a negative control, 6 mg of either surface (lane 5) or total biotinylated liver proteins (lane 6) was immunoprecipitated with a mAb M3A5 which recognizes an epitope shared by Golgi b-COP, a golgi membrane protein and microtubule-associated protein (MAP). The position of MAP doublet is indicated.

If p120 is (or part of the) DHBV receptor, it should be expressed on the cell surface. The possible cell surface distribution of p120 was examined by labeling primary duck hepatocytes with sulfo-LC-biotin, which is too bulky to penetrate the surface of viable cells. Since labeling was carried out on hepatocytes attached to dishes, dead cells could be removed by the successive PBS washing prior to and following labeling. Incubation of the biotinylated lysates with several pre-S constructs revealed availability of p120 on the cell surface (FIG. 26). It was detected very efficiently by the construct 80–102 (lane 1) and weakly by construct 25–102 (lane 3), but not by constructs 80–104 (lane 2) and 1–161 (lane 4). The much stronger intensity of p120 retained by 80–102 versus 25–102 probably reflects non-linearity of signal amplification by ECL. Under the same conditions p170 was retained by constructs 1–161 and 80–104, though the signal obtained was weaker. To rule out the possibility that the p120 and p170 detected were derived from a small amount of intracellular protein leaked from dead cells, immunoprecipitation of Golgi b-COP, a Golgi microtubule-associated protein was performed using monoclonal antibody M3A5. This mAb recognizes an epitope shared by the Golgi b-COP protein (110 kd) and a high MW doublet of microtubule-associated protein (MAP). Both 110 kd protein band (not shown) and a doublet high MW band (~300 kd) were precipitated only from total labeled duck liver lysate (FIG. 26, lane 6), but not from surface labeled lysate (lane 5), suggesting that contamination by cytoplasmic proteins was insignificant in these experiments. Disruption of D120 binding motif reduces DHBV infectivity The crucial role of pre-S residues 100–102 in mediating p120 interaction enabled us to test the significance of p120 in the DHBV life cycle by genetic approaches. Double amino acid substitutions were introduced into p120-binding residues 100–102 and succeeding residues 103–104 of the replication competent DHBV genome pDHBV3.5: F100V/R101L, R101I/R102D, R101L/R102L, and Y103C/Q104F. As a control, a mutant with triple aa substitutions, K95S/R97L/E98A, was used (the mutations cover the p170 binding site but do not abolish p170 binding). Although some of the mutations caused aa changes in the overlapping polymerase gene (R101I/R102D: S311Y/P312R; F100V/R101L: F310C; Y103C/Q104F: S314F; K95S/R97L/E98A: S306C), this portion of the polymerase is a spacer region tolerant of substantial sequence alterations. After the mutants were transfected into LMH cells, secretion of pelletable particles into culture medium at different time points were measured. In general, no major variation in secretion of virion/core particles was found except that mutant Y103C/Q104F produced fewer particles at day 7 post-transfection. All the mutants displayed similar ratio of virion/core particles, since removal of core particles by Pronase/DNaseI decreased hybridization signal similarly for all the mutants (FIG. 27). No major difference in levels of ccc DNA, total and core DHBV RNA, and core DNA could be detected at day 7 post-transfection.

Equal amounts of virion particles concentrated from culture medium were used to infect primary duck hepatocytes for 6.5 hr. The infectivity was measured by Southern blot hybridization of intracellular DHBV DNA at day 8 post-infection. All the mutants except the triple mutant K95S/R97L/E98A exhibited significantly reduced amount of viral DNA in infected cells. According to results from four independent transfection/infection experiments, the degree in reduction of infectivity follows the order Y103C/Q104F>F100V/R101L and R101I/R102D>R101L/R102L. Immunofluorescence staining of infected cells with an anti-pre-S antibody revealed a corresponding reduction in the number of cells infected, though the intensities of fluorescence in the positive cells were not significantly different between cells infected with wild-type virus and mutants.

Synthetic Pre-S Peptides Covering the p170/p120 Binding Sites Interfere With DHBV Infectivity The p170 binding site entirely covers the three clustered neutralizing epitopes, and p120 binding site overlaps the C-terminal epitope. If the clustered epitopes are part of receptor binding site, then pre-S peptides covering this region might compete for receptor binding and interfere with DHBV infection. Two pre-S peptides were used for this experiment: 80–102 and 80–104. The GST fusion protein of peptide 80–102 binds p120 (but not p170) efficiently, while peptide 80–104 binds p170 (but not p120) with low efficiency. The two pre-S peptides were purified from GST by thrombin cleavage. Peptides were pre-incubated with hepatocyte monolayers for 1 hour before infection with 1 =|l of viremic duck serum. As a result, both peptides reduced DHBV infectivity. At the concentration of 10 mg/ml, peptides 80–102 and 80–104 reduced DHBV infectivity to similar degrees. Increasing the peptide concentration to 1 mg/ml enhanced inhibitory effect significantly for peptide 80–104 but only slightly for peptide 80–102. The strong inhibitory effect of peptide 80–104 lends support to the hypothesis that the clustered neutralizing epitopes are a contact site of DHBV receptor.

p120 Expression is Restricted to DHBV Infectible Tissues

Figure 29A:
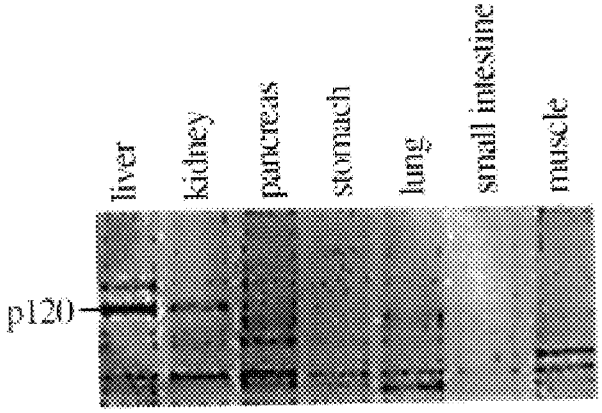
FIGS. 29(A and B) is a pair of blots showing tissue distribution of p120. A) Detection by the pre-S construct. About 0.5 gm of tissue was homogenized in lysis buffer, precleared and incubated with 2 $\mu$g GST fusion protein of 80–102 immobilized on Sepharose beads. Bound proteins were separated by SDS-6% PAGE minigel and visualized by Coomassie blue staining. Position of the p120 band is indicated. B) Detection by direct Western blot. 50 $\mu$g of protein was separated by SDS-PAGE and transferred to nitrocellulose filter. The blot was incubated with a rabbit polyclonal anti-p120 antibody and positive signal revealed by HRP-conjugated anti-rabbit serum and DAB.
Figure 29B:
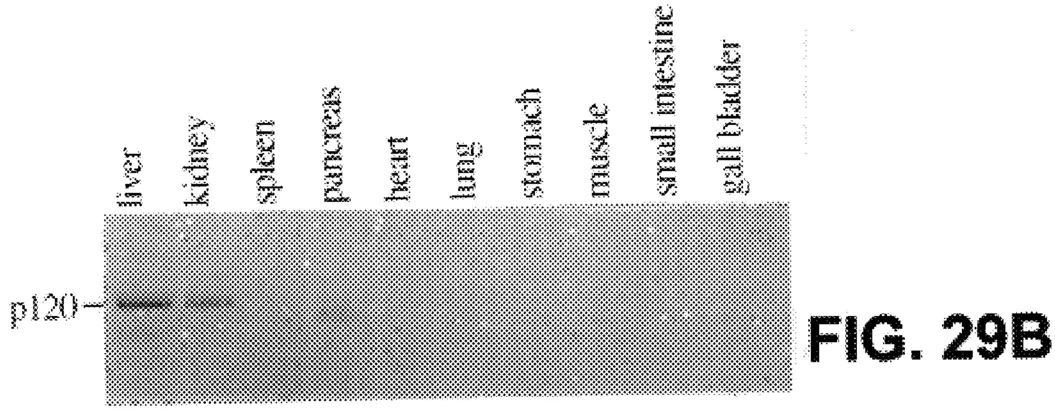

To study the tissue distribution of p120, tissue lysates were precleared and incubated with the construct 80–102, and retained proteins revealed by SDS-PAGE minigel followed by Coomassie blue staining. p120 was clearly found in the liver and kidney (FIG. 29). It was weakly detected in pancreas but not in other tissues examined, including stomach, lung, small intestine, skeletal muscle, and spleen, heart, gall bladder. As an independent confirmation of this result, a direct Western blot detection method for p120 was developed. In accordance with the affinity approach, p120 was found most abundantly in the liver followed by kidney, but weakly in pancreas (FIG. 29). No p120 was found in other tissues tested. This pattern of tissue specific distribution of p120-coincides with the known tissue tropism of DHBV infection.

Four peptide sequences of p120 were obtained (FIG. 30). Data base search revealed complete homology of all the peptides with chicken and human glycine decarboxylase. This result suggests that the p120 pre-S binding protein is actually the duck form of glycine decarboxylase. Based on this assumption, p120 cDNAs were cloned from duck liver cDNA libraries by cross-hybridization with a 2.3 kb fragment of the chicken glycine decarboxylase cDNA. Several cDNA molecules were obtained from oligo-dT primed library. The longest clone was studied in detail. The complete nucleotide and deduced amino acid sequences of the coding sequence of this clone are shown in FIG. 31. The clone contains 2922 nucleotides encoding 973 amino acid residues. All four peptide sequences obtained from. microsequencing could be found within this coding region. Compared to chicken glycine decarboxylase, the sequence homology at amino acid level is 98% (950/973) and there is a 6-a.a insetion at the N-terminal region of the duck protein.

Figure 24:
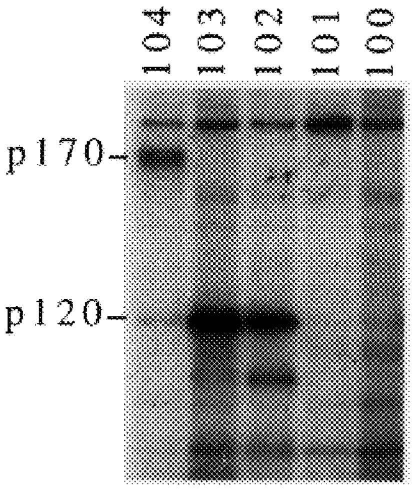
FIG. 24 is a gel showing that p120 retention by the C-terminal deletion constructs of pre-S protein requires an exact truncation at residue 102 or 103. The five constructs used had common N-terminus at residue 80 but different C-terminus at residues 104, 103, 102, 101, and 100, respectively. Detection of p120 from 35S labeled primary duck hepatocyte lysates was performed as described in the legend to FIG. 21. Positions of p170 and p120 are indicated.
Figure 25B:
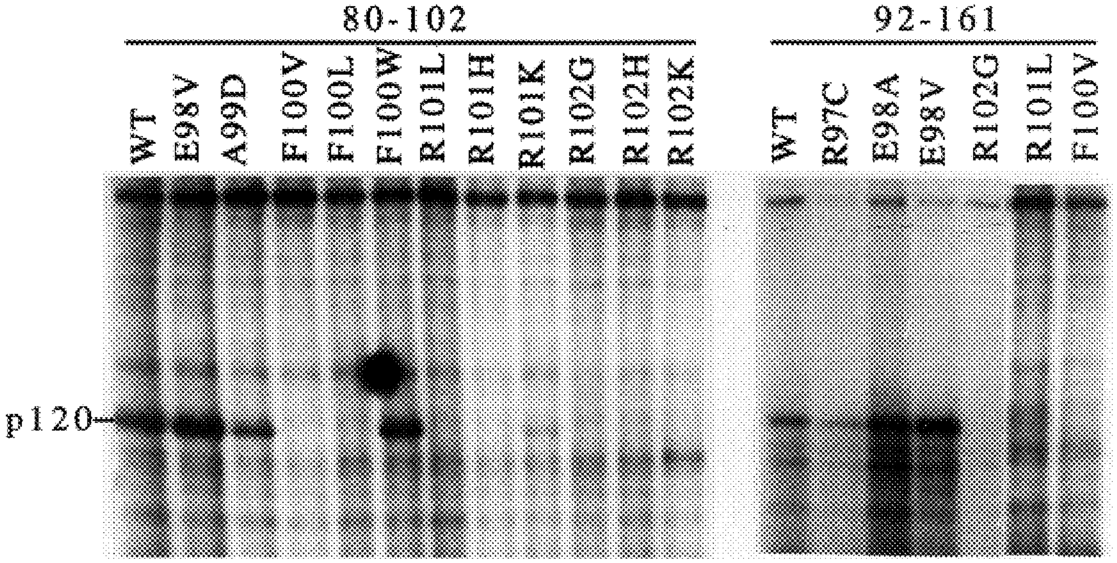
FIGS. 25A and B are a table and a fluorograph illustrating the critical role of Pre-S residues 100–102 in p120 binding. Single aa substitutions were introduced into either construct 80–102 or construct 92–161 and effects on p120 binding examined with 35S labeled primary duck hepatocyte lysates. A) Schematic representation of the mutants and binding results. B) The fluorograph showing binding results of mutants in the construct 80–102 (left) or 92–161 (right). WT: wild-type (SEQ ID NO:69). Position of p120 band is indicated.

To test whether the duck glycine decarboxylase is indeed the pre-S binding protein we characterized, the coding region of this clone was subcloned into pBluscript vector and encoded protein translated in vitro in rabbit reticulocyte lysate. Although this clone lacks 37 N-terminal amino acid residues compared with the putative precursor protein of the chicken gene, it misses only three amino acid residues as compared with the mature form of the chicken protein. The in vitro translated protein had molecular mass about 120 kD, close to the size observed for the pre-S binding protein detected in duck liver. When incubated with various forms of GST-DHBV pre-S proteins, the radiolabeled protein could be retained only by pre-S protein with either C-terminal truncation at a 102 or N-terminal truncation at 92 (FIG. 24, lanes 2 and 4). It could not be retained by the intact pre-S protein nor by a construct with C-terminal truncation at 104 (FIG. 24, lanes 1 and 3). Moreover, single point mutation in residue 101 or 102, which form part of p120 contact site, abolished retention of the in vitro translated duck glycine decarboxylase protein (FIG. 24, lane 5, 6). This pattern of selective binding to a few truncated forms of pre-S protein through a critical contact site is in complete accordance with results obtained with p120 from duck liver, confirming-that the p120 pre-S binding protein is indeed glycine decarboxylase.

Properties of p120

Compared with p170, p120 exhibits remarkable tissue specific expression in the liver and the kidney, the major sites of DHBV replication. The data indicating that p120 is a candidate DHBV binding protein of a putative receptor complex is supported by: 1) restricted tissue distribution coincident with the tissue tropism of DHBV replication; 2) co-localization of the binding site with virus-neutralizing epitopes; 3) interference of DHBV infection by short pre-S peptides covering its (and p170's) binding site; 4) reduced infectivity of DHBV mutants with a disrupted p120 binding motif; 5) cell surface localization on primary duck hepatocytes.

p120 is not exclusively a cell-surface protein. Although we could detect p120 by cell surface labeling with sulfo-LC-biotin, the protein is also located within the hepatocytes. Whether the amount of p120 present on cell surface is sufficient to allow viral entry is not presently known. Alternatively, p120 could play a role in the intracellular trafficking of internalized DHBV particles and if this proves to be-the case, it does not need to be located principally on the cell surface. It was determined that a homologous binding protein was detectable in DHBV non-infectible hosts. Using the pre-S construct 80–102, we could detect p120-related proteins in chicken and human liver. If the host and tissue specificities of DHBV infection are determined at the receptor level, the double specificities may be explained by postulating that p170 and p120 proteins are part of a DHBV receptor complex.

The p120 reactive peptide 80–102 does not inhibit DHBV replication to as great an extent as p170 reactive peptide 80–104. A possible explanation for this phenomenon is that DHBV-hepatocyte interaction is initiated by binding to p170, followed by binding to p120. A peptide that inhibits the first stage of interaction (80–104) would potentially be a more potent inhibitor of infection than a peptide that inhibits a later stage of this interaction (80–102). As for the observation that the inhibitory effect is dose-dependent for 80–104 but not obviously for 80–102, a difference in their affinity for the respective target protein is one possible explanation. In this regard, 80–102 has a strong affinity for p120 and its maximum inhibitory effect is probably reached at the lowest peptide concentration used; whereas 80–104 has low affinity for p170 and its maximal inhibitory effect requires the highest peptide concentration.

Figure 23:
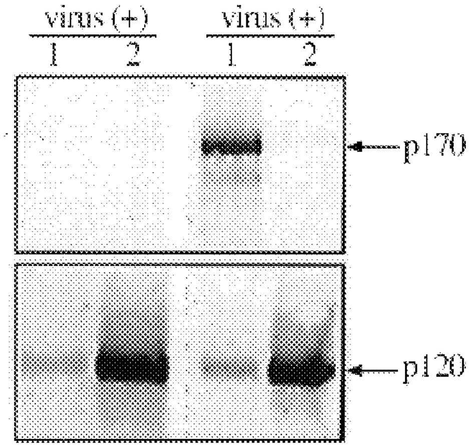
FIG. 23 is a pair of Northern blots illustrating p120 retention by the intact pre-S construct. DHBV infected (left panel or non infected (right panel) duck liver was homogenized in lysis buffer. The cell lysate was incubated with intact pre-S construct 1–161 (lane 1) or a truncation construct 80–102 (lane 2). The proteins retained on sepharose beads were separated on SDS-8% PAGE gel and blotted onto nitrocellulose filter. After incubation with a rabbit anti-p170 antibody (upper panel) (16a) or anti-p120 antibody (lower panel), the protein bands were revealed by HRP-conjugated anti-rabbit serum and DAB. The positions of p170 and p120 are indicated.

As shown in FIG. 23, intact pre-S protein expressed in *E. coli* retains only a small amount of p120. Addition of DHBV viremic duck serum into a tube containing metabolically labeled hepatocyte lysate and immobilized pre-S construct 80–102 failed to significantly reduce the amount of p120 retained to the beads, suggesting DHBV particles do not have large amount of truncated pre-S protein similar to those seen in vitro to bind p120 efficiently. However, considering the fact that residues 101 and 102 are both arginine, p120-reactive pre-S protein can be generated by proteolytic cleavage through a trypsin-like protease or an endopeptidase specific for dibasic residues (see Davey et al. (1994) EMBO J. 13:5910–5921). Proteolytic cleavage of viral envelope protein after di- or tetra-basic residues is required for infectivity of myxoviruses and retroviruses, although in these instances the cleavage: 1) occurs during virion maturation; and 2) exposes a new hydrophobic N-terminus required for virus-cell fusion. In addition, Lu and colleagues recently demonstrated that protease treatment of HBV particles enhanced its infectivity in a hepatoma cell line (Lu et al. (1996) J. Virol. 70:2277–2285), thus reinforcing the hypothesis that hepadnavirus infection may require the action of proteases.

The simplest model to account for p170 and p120 as components of DHBV receptor is as follows: virion particles are attracted onto the hepatocyte surface initially by p170. This event is followed by either direct conformational change of the pre-S protein or by proteolytic cleavage at Arg102 to activate p120 binding. p120 binding subsequently allows viral entry or participates in intracellular trafficking. Irrespective of how the p120-DHBV interaction occurs, the role of p120 in DHBV life cycle is testable by two experimental approaches: namely, whether antibody against p120 inhibits DHBV infection of primary duck hepatocytes, and/or whether transfection of p120 cDNA (together with p170 cDNA) into nonpermissive cells renders them susceptible to DHBV infection.

Activity Assays

Each such homolog can be definitively identified as a hepadnaviral receptor by any of the following assays:

1) Antibody inhibition experiment. Primary human hepatocytes can be obtained by perfusion, cultured, and infected with hepadnavirus according to the method of Gripon et al. (*Virology,* 192:534–540, 1993) and cultured. An antibody, e.g., a rabbit polyclonal antibody, is added to the culture medium during the stage when virus particles are put on cell monolayer, preferably in a 1:100 to 1:1000 dilution. After infection, cells are maintained for a week. Cellular DNA analyzed by Southern blot for the presence of HBV DNA. If the addition of antibody to the culture results in a reduced level, or complete absence, of HBV compared with the amount of HBV DNA detected in control cells infected in the absence of receptor-specific antibody, then the antibody blocks viral infectivity, and the receptor to which it specifically binds is a hepadnavirus receptor.

2) Cell Transfection Assay. To assay the ability of a hepadnavirus receptor cDNA to render a cell line susceptible to HBV infection, the cDNA is first transfected into the cells. For this purpose, the coding sequence of the receptor gene is cloned into a vector for expression in mammalian cells. An appropriate vector is one that contains a selectable marker, e.g., neomycin resistance, a variety of appropriate vectors being commercially available. Methods of transfecting cloned DNA into an established cell line is a basic technique known to those of ordinary skill in the art. The usual method is by $CaCl_2$ precipitation. After transfection, a reagent such as neomycin is applied to select for cells receiving the plasmid DNA containing the gene of interest. These cells are cloned and used for further analysis. The second step is to test whether these transfected cell lines are newly infectible with HBV. No known cell lines are susceptible to HBV infection. However, a few human hepatoma cell lines support HBV replication when HBV DNA is transfected into them. This suggests that while their intracellular machinery is compatible for the HBV life cycle, they do not allow HBV adsorption or penetration, with a defect probably at the receptor level. These cell lines include, e.g., HepG2 cells and Hhu7 cells. Thus, these cell lines should be the first choice for transfection by the cDNA of interest. To infect the cells, HBV particles are transfected into the cell line of choice. The cells are incubated for a few hours to overnight and then thoroughly washed to remove any unbound virus. After further culture for one to two weeks, cells are lysed. Cellular DNA is tested by Southern blot analysis for the presence of viral DNA. The virus stock could come from serum taken from hepatitis B patients positive for HBeAg, or it could be concentrated from medium of hepatoma cells transfected with cloned HBV DNA. Evidence of viral replication unambiguously demonstrates that the gene of interest encodes the cellular receptor specific for HBV.

Preparation of the Isolated DNAs of the Invention

Some alternative means of preparing the nucleic acids of the invention, using the information provided herein and standard techniques, are as follows:

(1) A nucleic acid fragment having a nucleotide sequence shown in FIGS. 18–19, or a nucleic acid encoding the amino acid sequence shown in FIGS. 18–19, but, owing to the degeneracy of the genetic code, having a nucleotide sequence different from that shown in the figure, may be synthesized by standard chemical means as generally applied to synthesis of oligonucleotides.

(2) An isolated DNA prepared by any of the methods outlined herein (including the methods originally used to obtain the DNAs of the invention) may be used to probe an appropriate cDNA library or genomic DNA library. Preferably, a human liver cDNA library is used, either oligo-dT primed or primed by random hexamer primers. The ideal library is derived form normal human liver rather than hepatoma or cultured hepatocyte lines, because hepatoma or hepatocyte lines are generally not infectible with HBV. The library is constructed in a lamda vector as a bacteriophage.

To screen the library, phages are grown in NZY medium at around $5\times10^4$ per plate, transferred to a nitrocellulose filter, and hybridized with a nucleic acid of the invention, e.g., the 2.5 kb p170 cDNA randomly labeled by $^{32}$p dCTP. The blots are then washed at approximately 50° C. with 2×SSC/0.1% SDS. Positive clones are sequenced to verify homology to p170. The stringency of the washing step after hybridization can be adjusted from low to high, and the clone that hybridizes with p170 at the highest. stringency is most likely to be a homolog, e.g., a human homolog, of p170. High stringency hybridization can be performed by hybridizing in 50% deionized formamide, 800 mM NaCl, 20 mM Pipes, pH 6.5, 0.4% SDS, 500 $\mu$g/ml denatured, sonicated salmon sperm DNA at 42° C. for 12–20 hours; and washing in 30 mM NaCl, 3.0 mM sodium citrate, 0.5% SDS at 65° C.). It is expected that hybridization and wash conditions such as the highly stringent conditions set forth above would be adequate; if necessary, the stringency may be increased or decreased, without undue experimentation, using methods well known to those of ordinary skill in the art (see, e.g., Sambrook et al., Molecular Cloning: A Laboratory Manual, Cold Spring Harbor Laboratory, Cold Spring Harbor, N.Y., 1989). The stringency of washing is dependent on two factors primarily: temperature (the higher the more stringent) and SSC concentration (the lower the more stringent). The identity of the homolog is verified by its binding affinity for the pre-S domain of the appropriate hepadnavirus, e.g., the human HBV pre-S domain. Affinity can be determined by transfecting the cDNA into a cell line which normally does not bind the human HBV particle, labeling the cell with $^{35}$S methionine, and reacting the cell lysate with a GST fusion protein of the human HBV pre-S protein, as was shown above for the DHBV pre-S-p170 interaction.

Anti-hepadnavirus Receptor Antibodies

Cell receptor or receptor fragments of the invention may be used to generate antibodies by conventional methods well known to those skilled in the art, including those which generate polyclonal antibodies and those which generate monoclonal antibodies (see, e.g., Coligan et al., eds. *Current Protocols in Immunology*, Wiley & Sons, Inc., 1994). For example, the deduced amino acid sequence of the p170 receptor can be used to guide the selection of regions of the receptor protein which would be likely to be exposed on the cell surface, and thus would be presented to antibodies in vivo. A short peptide representing one or more of such regions may be synthesized (e.g., chemically or by recombinant DNA techniques) and used to immunize an animal (e.g., a rabbit or a mouse) to generate polyclonal or monoclonal antibodies. For example, certain of the peptides 1–4 shown in FIG. 14A can be chemically synthesized using standard techniques. Alternatively, the p170 amino acid sequence responsible for binding the pres domain should be virus neutralizing and thus would be a suitable peptide antigen. The peptides are used to generate polyclonal antibodies in rabbits by the following procedure:

A preparation of a given peptide emulsified with complete Freund's Adjuvant is injected intradermally into rabbits. Booster injections are emulsified in complete adjuvant and injected at monthly intervals.

Antibody titer is assessed using either of two methods. First, serial dilutions of the antiserum in 1% normal rabbit serum are incubated with $^{125}$I-labelled p170 receptor fragment by standard methods (e.g., see Segre et al., *J. Biol. Chem.* 254:6980, 1979) for 24 h at 4° C. The bound $^{125}$I-p170 receptor fragments are separated from unbound fragments by addition of 100 $\mu$l of second antibody (anti-rabbit IgG, Sigma) diluted 1:20 and 1 ml of 5% polyethylene glycol, followed by centrifugation at 2000 rpm for 30 min. at 4° C. The supernatant is removed and the pellet analyzed for radioactivity in a γ-counter. In the second method, cell lines expressing recombinant hepadnavirus receptor (COS cells or CHO cells transfected with a nucleic acid encoding a hepadnavirus-receptor) are incubated with serially diluted antibody at 4° C., 20° C. or 37° C. for 1–4 hours. The cells are rinsed with PES (×3) and incubated for 2 h at 4° C. with $^{125}$I-labelled (NEN, Dupont) or FITC-labelled (Sigma) second antibodies. After rinsing (×3 with PBS), the cells were either lysed with 0.1 M NaOH and counted in γ-counter (if $^{125}$I-labelled second antibody was used) or fixed with it paraformaldehyde and examined by fluorescent microscopy (if FITC-labelled second antibody was used).

Another method for producing antibodies utilizes as antigen the intact cell receptor protein of the invention expressed on the surface of cells (e.g., mammalian cells, such as COS cells, transfected with DNA encoding the receptor). Such cells are prepared by standard techniques, e.g., by the DEAE-dextran transfection method, using a vector encoding and capable of directing high-level expression of the cell receptor. Such cells may be used to generate polyclonal or monoclonal antibodies. For example, monoclonal antibodies specific for the hepadnavirus receptor can be produced by the following procedure:

Intact COS cells expressing high levels of hepadnavirus receptor on the cell surface are injected intraperitoneally (IP) into Balb-c mice (Charles River Laboratories, Wilmington, Mass.). The mice are boosted every 4 weeks by IP injection, and are hyperimmunized by an intravenous (IV) booster 3 days before fusion. Spleen cells from the mice are isolated and are fused by standard methods to myeloma cells. Those hybridomas which produce antibodies capable of binding to the hepadnavirus receptor are cultured and subcloned.

Mapping the pre-S binding site on the hepadnavirus receptor. Several experimental approaches can be envisaged for mapping the binding site on the receptor.

(1) The nucleic acid encoding the receptor is cloned into a transcription vector, transcribed, and translated in rabbit reticulocytes in the presence of radioactive tracer ($^{35}$S methionine). The labeled lysate is incubated with a GST-pre-S fusion protein. If binding is positive and specific, a series of deletion mutants of the receptor gene can be made, transcribed, translated, and reacted with GST-preS fusion protein.

(2) The nucleic acid encoding the receptor, or a fragment thereof, is cloned into the pGEX 2TK vector (Pharmacia) and expressed as a GST fusion protein. A hepadnavirus pre-S protein is expressed in eucaryotic cells by stable transfection-selection (as described above). The pre-S expressing cells are labeled and lysate is reacted with a GST fusion protein of the hepadnavirus receptor gene to determine the specificity of the interaction.

(3) The nucleic acid encoding the receptor gene is expressed in eucaryqtic cells and interacted with a GST pre-S fusion protein. This is the reciprocal of (2), above. This is the preferred approach if posttranslational modifications such as glycosylation or phosphorylation are essential for binding of the hepadnavirus receptor to pre-S protein.

Expression of Polypeptides

Polypeptides according to the invention may be produced by expression from a recombinant nucleic acid having a sequence encoding part or all of a cell receptor of the invention, using any appropriate expression system: e.g., transformation of a suitable host cell (either prokaryotic or eukaryotic) with the recombinant nucleic acid in a suitable expression vehicle (e.g., pcDNAI). The precise host cell used is not critical to the invention; however, the following host cells are preferred: COS cells, CHO cells, and human liver cells. Mammalian cell transfection methods are described, e.g., in Ausubel et al. (Current Protocols in Molecular Biology, John Wiley & Sons, New York, 1989); expression vehicles may be chosen from those discussed, e.g., in Cloning Vectors: A Laboratory Manual (P. H. Pouwels et al., 1985, Supp. 1987). Stably transfected cells are produced via integration of receptor DNA into the host cell chromosomes. Suitable DNAs are inserted into pcDNA, pcDNAI-Neo, or another suitable plasmid, and then cells are transfected with this plasmid with or without cotransfection with psV-2-Neo, or psV-2-DHFR by standard electroporation, calcium phosphate, and/or DEAE/Dextran techniques. Selection of transfected cells is performed using progressively increasing levels of G418 (Geneticin, GIBCO), and if necessary, methotrexate.

DNA sequences encoding the polypeptides of the invention can also be expressed in a prokaryotic host cell. DNA encoding a cell receptor or receptor fragment is carried on a vector operably linked to control signals capable of effecting expression in the prokaryotic host. If desired, the coding sequence may contain, at its 5' end, a sequence encoding any of the known signal sequences capable of effecting secretion of the expressed protein into the periplasmic space of the host cell, thereby facilitating recovery of the protein and subsequent purification.

Prokaryotes most frequently used are various strains of *E. coli*; however, other microbial strains may also be used. Plasmid vectors are used which contain replication origins, selectable markers, and control sequences derived from a species compatible with the microbial host. For example, *E. coli* may be transformed using derivatives of pBR322, a plasmid constructed by Bolivar et al. (Gene 2: 95, 1977) using fragments derived from three naturally-occurring plasmids, two isolated from species of Salmonella, and one isolated from *E. coli.* pBR322 contains genes from ampicillin and tetracycline resistance, and thus provides multiple selectable markers which can be either retained or destroyed in constructing the desired expression vector. Commonly used prokaryotic control sequences (also referred to as "regulatory elements") are defined herein to include promoters for transcription initiation, optionally with an operator, along with ribosome binding site sequences. Promoters commonly used to direct protein expression include the beta-lactamase (penicillinase), the lactose (lac) (Chang et al., Nature 198: 1056, 1977) and the tryptophan (Trp) promoter systems (Goeddel et al., Nucl. Acids Res. 8: 4057, 1980) as well as the lambda-derived $P_L$ promoter and N-gene ribosome binding site (Simatake et al., Nature 292:128, 1981).

The nature of the cell receptor proteins of the invention is such that, upon expression within a cell, it is moved to the cellular membrane and partially through the membrane, so that part of it remains embedded in the membrane, part extends outside the cell, and part remains within the cell. Transformed cells bearing such embedded cell receptors may themselves be employed in the methods of the invention, or the receptor protein may be extracted from the membranes and purified.

Expression of peptide fragments lacking the hydrophobic portions of the protein responsible for anchoring the intact protein in the cellular membrane would not be expected to become embedded in the membrane; whether they remain within the cell or are secreted into the extracellular medium depends upon whether or not a mechanism promoting secretion (e.g., a signal peptide) is included. If secreted, the polypeptide of the invention can be harvested from the medium; if not, the cells must be broken open and the desired polypeptide isolated from the entire contents of the cells.

The polypeptide of the invention can be readily purified using affinity chromatography. Antibodies to these polypeptides, or the receptor specific ligands (e.g., a preS polypeptide) may be covalently coupled to a solid phase support such as Sepharose 4 CNBr-activated sepharose (Pharmacia), and used to separate the polypeptide of the invention from any contaminating substances. Typically 1 mg of ligand or antibody will be incubated with CNBr-activated sepharose at 4° C. for 17–20 h (with shaking). The sepharose is rinsed with 1 M Tris HCL (pH8) to block excess active sites. The Sepharose™-p170, Sepharose™-pre-S, or Sepharose™-antibody is then incubated with the crude polypeptide in phosphate-buffered saline (pH 7.4) at 4° C. for 2 h (with shaking). The Sepharose™ is then typically packed in a column, thoroughly washed with PBS (typically 10 times the column volume), and eluted with dilute HCl in $H_2O$ (pH 1.85). The eluate may then be concentrated by lyophylization and its purity checked, for example, by reverse phase HPLC.

Screening for Hepadnavirus Receptor Antagonists and Agonists

Candidate antagonists and agonists may be screened for the ability to compete with or enhance binding of the pre-S domain to the hepadnavirus receptor using the assays described herein.

In one example, those antibodies that recognize the hepadnavirus receptor on the intact cells are screened for their ability to compete with a form of hepadnavirus envelope protein, e.g., a pre-S polypeptide, for binding to a hepadnavirus receptor. Cells expressing hepadnavirus receptor on the cell surface are incubated with the $^{125}$I-pre-S analog in the presence or absence of the polyclonal or monoclonal antibody to be tested for 4 h at 15° C. The antibody used may be from crude antiserum, cell medium, or ascites, or in purified form. After incubation, the cells are rinsed with binding buffer (e.g., physiological saline), lysed, and quantitatively analyzed for radioactivity using a gamma-counter. Antibodies that reduce binding of the pre-S analog to the hepadnavirus receptor are classified as competitive; those which do not are noncompetitive.

Therapeutic Use

Therapeutic administration of a mutant polypeptide can be accomplished using the polypeptide directly or by administering the polypeptide with gene therapy techniques. A nucleic acid that included a promoter operatively linked to a sequence encoding a polypeptide of the invention is used to generate high-level expression of the polypeptide in cells transfected with the nucleic acid. Gene transfer can be performed ex vivo or in vivo. To administer the nucleic acid ex vivo, cells can be removed from the body of the patient, transfected with the nucleic acid encoding the mutant polypeptide, and returned to the patient's body. Alternatively the nucleic acid can be administered in vivo, by transfecting the nucleic acid into target cells (e.g., hepatocytes) so that the mutant polypeptide is expressed in situ.

The nucleic acid molecule is contained within a non-replicating linear or circular DNA or RNA molecule, or within an autonomously replicating plasmid or viral vector, or may be integrated into the host genome. Any vector that can transfect a cell can be used in the methods of the invention. Preferred vectors are viral vectors, including those derived from replication-defective hepatitis virus (e.g., HBV and HCV), retrovirus (see, e.g., WO89/07136; Rosenberg et al., N. Eng. J. Med. 323(9):570–578, 1990; Miller et al., 1993 supra), adenovirus (see, e.g., Morsey et al., J. Cell. Biochem., Supp. 17E, 1993; Graham et al., in Murray, ed., *Methods in Molecular Biology: Gene Transfer and Expression Protocols.* Vol. 7, Clifton, N.J.: the Human Press 1991: 109–128), adeno-associated virus (Kotin et al., Proc. Natl. Acad. Sci. USA 87:2211–2215, 1990), replication defective herpes simplex virus (HSV; Lu et al., Abstract, page 66, Abstracts of the Meeting on Gene Therapy, Sep. 22–26, 1992, Cold Spring Harbor Laboratory, Cold Spring Harbor, N.Y.), and any modified versions of these vectors. Other preferred viral vectors include those modified to target a specific cell type (see, .e.g., Kan et al. WO 93/25234; Kasahara et al. Science, 266:1373–76, 1994; Dornburg et al. WO 94/12626; Russell et al. WO 94/06920). Methods for constructing expression vectors are well known in the art (see, e.g., Molecular Cloning: A Laboratory Manual, Sambrook et al., eds., Cold Spring Harbor Laboratory, 2nd Edition, Cold Spring Harbor, N.Y., 1989).

Appropriate regulatory sequences can be inserted into the vectors of the invention using methods known to those skilled in the art, e.g., by homologous recombination (Graham et al., *J. Gen. Virol.* 36:59–72, 1977), or by other appropriate methods (Sambrook et al., eds., supra). Promoters are inserted into the vectors so that they are operatively linked 5' to the nucleic acid sequence encoding the mutant polypeptide. Any promoter that is able to initiate transcription in a target cell can be used in the invention. For example, non-tissue specific promoters, such as the cytomegalovirus (DeBernardi et al., Proc. Natl. Acad. Sci. USA 88:9257–9261, 1991, and references-therein), mouse metallothionine I gene (Hammer, et al., J. Mol. Appl. Gen. 1:273–288, 1982), HSV thymidine kinase (McKnight, Cell, 31:355–365, 1982), and SV40 early (Benoist et al., Nature, 290:304–310, 1981) promoters may be used. Preferred promoters for use in the invention are hepatocyte-specific promoters, the use of which ensures that the mutant polypeptides are expressed primarily in hepatocytes. Preferred hepatocyte-specific promoters include, but are not limited to the albumin, alpha-fetoprotein, alpha-1-antitrypsin, retinol-binding protein, and asialoglycoprotein receptor promoters. Additional viral promoters and enhancers, such as those from herpes simplex virus (types I and II), hepatitis virus (Types A, B, and C), and Rous sarcoma virus (RSV; Fang et al., Hepatology 10:781–787, 1989), can also be used in the invention.

The mutant polypeptides of the invention, and the recombinant vectors containing nucleic acid sequences encoding them, may be used in therapeutic compositions for preventing or treating HBV infection. The therapeutic compositions of the invention may be used alone or in admixture, or in chemical combination, with one or more materials, including other mutant polypeptides or recombinant vectors, materials that increase the biological stability of the oligonucleotides or the recombinant vectors, or materials that increase the ability of the therapeutic compositions to penetrate hepatocytes selectively. The therapeutic compositions of the invention can be administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in *Remington's Pharmaceutical Sciences*, a standard reference text in this field.

The therapeutic compositions of the invention can be administered in dosages determined to be appropriate by one skilled in the art. An appropriate dosage is one which effects a reduction in a disease caused by HBV infection. It is expected that the dosages will vary, depending upon the pharmacokinetic and pharmacodynamic characteristics of the particular agent, and its mode and route of administration, as well as the age, weight, and health (including renal and hepatic function) of the recipient; the nature and extent of the disease; the frequency and duration of the treatment; the type of, if any, concurrent therapy; and the desired effect. It is expected that a useful dosage contains between about 0.1 to 100 mg of active ingredient per kilogram of body weight. Ordinarily a dosage of 0.5 to 50 mg, and preferably, 1 to 10 mg of active ingredient per kilogram of body weight per day given in divided doses, or in sustained release form, is appropriate.

The therapeutic compositions of the invention may be administered to a patient by any appropriate mode, e.g., parenterally, as determined by one skilled in the art. Alternatively, it may by necessary to administer the treatment surgically to the target tissue. The treatments of the invention may be repeated as needed, as determined by one skilled in the art.

The invention also includes any other methods which accomplish in vivo transfer of nucleic acids into target cells. For example, the nucleic acids may be packaged into liposomes, non-viral nucleic acid-based vectors, erythrocyte ghosts, or microspheres (microparticles; see, e.g., U.S. Pat. No. 4,789,734; U.S. Pat. No. 4,925,673; U.S. Pat. No. 3,625,214; Gregoriadis, Drug Carriers in Biology and Medicine, pp. 287–341 (Academic Press, 1979)). Further, delivery of mutant polypeptides be accomplished by direct injection of their nucleic acid coding sequences into target tissues, for example, in a calcium phosphate precipitate or coupled with lipids, or as "naked DNA".

Mutant core polypeptides and core-surface fusion proteins of the invention can be tested for their ability to inhibit hepadnavirus replication in an animal model. For example, candidate polypeptides can be injected into an animal that is infected with a hepadnavirus, e.g., a woodchuck, duck, or ground squirrel harboring its respective hepatitis B virus variants (see, e.g., Mason et al., *J. Virol.* 36:829, 1980; Schodel et al., in *Molecular Biology of hepatitis B virus*, CRC press, Boca Raton, p. 53–80, 1991; Summers et al., *Proc. Natl. Acad. Sci. USA,* 75:4533–4537, 1978). Candidate polypeptides can also be analyzed in transgenic animal strains developed for the purpose of studying hepadnaviral gene expression (see, e.g., Babinet et al., Science, 230:1160–63, 1985; Burk et al., J. Virol. 62:649–54, 1988; Chisari et al., Science 230:1157–60, 1985; Chisari, in *Current Topics in Microbiology and Immunology*, p. 85–101, 1991). Candidate polypeptides of the invention can also be tested in animals that are naturally infected with HBV, e.g., in chimpanzees, by administering the polypeptides, or the nucleic acids encoding them, to the animal by one of the methods discussed above, or by other standard methods.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions.

All publications cited herein are fully incorporated by reference herein in their entirety.

Other embodiments are within the claims set forth below.

---

What is claimed is:

1. A purified polypeptide encoded by the nucleic acid of SEQ ID NO:74.

2. A purified polypeptide comprising the amino acid sequence of SEQ ID NO:75.

* * * * *